US012807706B2

(12) United States Patent
Lim et al.

(10) Patent No.: US 12,807,706 B2
(45) **Date of Patent: *Nov. 24, 2026**

(54) USE OF BRAIN-SPECIFIC ANTIGENS TO HOME, BLOCK AND DELIVER CELL-BASED TREATMENTS TO THE BRAIN

(71) Applicant: The Regents of the University of California, Oakland, CA (US)

(72) Inventors: Wendell A. Lim, San Francisco, CA (US); Milos Simic, San Francisco, CA (US); Hideho Okada, San Francisco, CA (US); Joseph H. Choe, San Francisco, CA (US); Payal B. Watchmaker, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 1025 days.

This patent is subject to a terminal disclaimer.

(21) Appl. No.: 17/792,385

(22) PCT Filed: Nov. 6, 2020

(86) PCT No.: PCT/US2020/059368

§ 371 (c)(1), (2) Date: Jul. 12, 2022

(87) PCT Pub. No.: WO2021/173193

PCT Pub. Date: Sep. 2, 2021

(65) Prior Publication Data

US 2023/0055337 A1 Feb. 23, 2023

Related U.S. Application Data

(60) Provisional application No. 62/980,885, filed on Feb. 24, 2020.

(51) Int. Cl.

| | |
|---|---|
| ***A61P 25/00*** | (2006.01) |
| ***A61K 40/11*** | (2025.01) |
| ***A61K 40/31*** | (2025.01) |
| ***A61K 40/40*** | (2025.01) |
| ***A61K 40/42*** | (2025.01) |
| ***A61P 35/00*** | (2006.01) |
| ***C07K 14/705*** | (2006.01) |
| ***C07K 16/28*** | (2006.01) |
| ***C07K 16/40*** | (2006.01) |
| ***C12N 5/0783*** | (2010.01) |

(52) U.S. Cl.

CPC .......... *C07K 16/2803* (2013.01); *A61K 40/11* (2025.01); *A61K 40/31* (2025.01); *A61K 40/4204* (2025.01); *A61K 40/4217* (2025.01); *A61K 40/422* (2025.01); *A61P 25/00* (2018.01); *A61P 35/00* (2018.01); *C07K 14/7051* (2013.01); *C07K 16/28* (2013.01); *C07K 16/40* (2013.01); *C12N 5/0636* (2013.01); *A61K 2239/47* (2023.05); *C07K 2319/03* (2013.01); *C07K 2319/71* (2013.01)

(58) Field of Classification Search

CPC ...... C07K 16/2803; A61P 25/00; A61P 35/00; A61K 40/40; A61K 2239/47

See application file for complete search history.

(56) References Cited

U.S. PATENT DOCUMENTS

| | | | | |
|---|---|---|---|---|
| 9,493,568 | B2 | 11/2016 | Reilly et al. | |
| 12,090,170 | B2 * | 9/2024 | Lim et al. | A61K 35/17 |
| 12,144,826 | B2 | 11/2024 | Lim et al. | |
| 12,636,345 | B2 | 5/2026 | Lim et al. | |
| 2012/0252875 | A1 | 10/2012 | Feinstein et al. | |
| 2013/0323300 | A1 * | 12/2013 | Olin et al. | A61K 35/30 424/450 |
| 2016/0264665 | A1 | 9/2016 | Lim et al. | |
| 2017/0029512 | A1 | 2/2017 | Raum et al. | |
| 2017/0210811 | A1 | 7/2017 | Wong et al. | |
| 2017/0309025 | A1 | 10/2017 | O'Rourke et al. | |
| 2018/0079812 | A1 | 3/2018 | Lim et al. | |
| 2018/0085401 | A1 | 3/2018 | Wu et al. | |
| 2020/0032351 | A1 | 1/2020 | Ramos et al. | |
| 2021/0023136 | A1 | 1/2021 | Lim et al. | |
| 2021/0023138 | A1 | 1/2021 | Lim et al. | |

(Continued)

FOREIGN PATENT DOCUMENTS

| | | | |
|---|---|---|---|
| JP | 2010534464 | A | 11/2010 |
| JP | 2016047825 | A | 4/2016 |

(Continued)

OTHER PUBLICATIONS

Theruvath et al. (2017) "Immu-07. checkpoint molecule B7-H3 is highly expressed on medulloblastoma and proves to be a promising candidate for car T cell immunotherapy" Neuro-Oncology, 19(Suppl 4), iv28-iv29. (Year: 2017).*

(Continued)

*Primary Examiner* — James Joseph Graber

(74) *Attorney, Agent, or Firm* — James S. Keddie; Bozicevic, Field & Francis LLP

(57) ABSTRACT

Provided herein is a cell comprising a recombinant nucleic acid encoding a transmembrane protein that has an extracellular binding domain that specifically binds to a brain-selective extracellular antigen, e.g., MOG, CDH10, PTPRZ1 or NRCAM, wherein the cell does not comprise a nucleic acid encoding an antigen-specific therapeutic that binds to a killing antigen expressed by a glioblastoma.

9 Claims, 18 Drawing Sheets

(56) References Cited

U.S. PATENT DOCUMENTS

| | | | |
|---|---|---|---|
| 2021/0023139 | A1 | 1/2021 | Lim et al. |
| 2024/0325449 | A1 | 10/2024 | Lim et al. |
| 2024/0344025 | A1 | 10/2024 | Lim et al. |
| 2025/0034229 | A1 | 1/2025 | Lim et al. |

FOREIGN PATENT DOCUMENTS

| | | | | |
|---|---|---|---|---|
| JP | 2018506293 A | 3/2018 | | |
| WO | WO 2014/130657 | 8/2014 | | |
| WO | WO 2016/138034 | 9/2016 | | |
| WO | WO 2017/025038 | 2/2017 | | |
| WO | WO 2017/087723 A1 | 5/2017 | | |
| WO | WO 2017/193059 A1 | 11/2017 | | |
| WO | WO 2018/039247 | 3/2018 | | |
| WO | WO 2018/123979 A9 | 7/2018 | | |
| WO | WO 2019/068007 A1 | 4/2019 | | |
| WO | WO 2019/195576 | 10/2019 | | |
| WO | WO 2019/195586 | 10/2019 | | |
| WO | WO2019195596 A1 * | 10/2019 | ............ | A61K 35/17 |
| WO | WO 2021/096783 A1 | 5/2021 | | |
| WO | WO 2023/049760 A1 | 3/2023 | | |

OTHER PUBLICATIONS

Lakshmanachetty et al. (2025) "DMG-27. Brain-sensing synNotch-CAR T cells demonstrate robust anti-tumor activity against diffuse midline glioma" Neuro-Oncology Pediatrics, Supplement 1, p. i16, Abstract ID: WUAF001.057. (Year: 2025).*

Teng et al. (2024) "Programmable synthetic receptors: the next-generation of cell and gene therapies" Signal transduction and targeted therapy, 9:7, 25 pages. (Year: 2024).*

Choe et al., "SynNotch-CAR T cells overcome challenges of specificity, heterogeneity, and persistence in treating glioblastoma", Sci Transl Med., Apr. 28, 2021, 13(591): doi:10.1126/scitranslmed.abe7378, 32 pages.

Fransson et al., "CAR/FoxP3-engineered T regulatory cells target the CNS and suppress EAE upon intranasal delivery", Journal of Neuroinflammation, 2012, 9:112, 12 pages.

Inda et al., "Tumor heterogeneity is an active process maintained by a mutant EGFR-induced cytokine circuit in glioblastoma", Genes & Development, 2010, 24: 1731-1745.

Jeuken et al., "Robust Detection of EGFR Copy No. Changes and EGFR Variant III: Technical Aspects and Relevance for Glioma Diagnostics", Brain Pathology, 2009, 19: 661-671.

Simic et al., "Programming tissue-sensing T cells that deliver therapies to the brain", Science, Dec. 6, 2024, 386: 1109, eadl4237, 14 pages.

Cajal et al., "Beyond molecular tumor heterogeneity: protein synthesis takes control", Oncogene, 2018, 37(19): 2490-2501.

Ding et al., "Clonal evolution in relapsed acute myeloid leukemia revealed by whole genome sequencing", Nature, 2012, 481(7382): 506-510.

Gerlinger et al., "Genomic architecture and evolution of clear cell renal cell carcinomas defined by multiregion sequencing", Nat Genet., 2014, 46(3): 225-233.

Kortum et al., "Targeted sequencing of refractory myeloma reveals a high incidence of mutations in CRBN and Ras pathway genes", Blood, 2016, 128(9): 1226-1233.

Landau et al., "Evolution and Impact of Subclonal Mutations in Chronic Lymphocytic Leukemia", Cell, 2013, 152: 714-726.

Liang et al., "Complex roles of the stroma in the intrinsic resistance to gemcitabine in pancreatic cancer: where we are and where we are going", Experimental & Molecular Medicine, 2017, 49: e406.

Lim et al., "The Principles of Engineering Immune Cells to Treat Cancer", Cell, 2017, 168(4): 724-740.

Rathore et al., "Radiomic MRI signature reveals three distinct subtypes of glioblastoma with different clinical and molecular characteristics, offering prognostic value beyond IDH1", Scientific Reports, 2018, 8: 5087.

Roybal et al., "Synthetic Immunology: Hacking Immune Cells to Expand Their Therapeutic Capabilities", Annu Rev Immunol, 2017, 35: 229-253.

Wang et al., "Clonal Evolution in Breast Cancer Revealed by Single Nucleus Genome Sequencing", Nature, 2014, 512(7513): 155-160.

Akhavan et al., "CAR T cells for brain tumors: Lessons learned and road ahead", Immunol Rev. Jul. 2019, 290(1): 60-84.

Choi et al., "Engineering Chimeric Antigen Receptor T cells to Treat Glioblastoma", J Target Ther Cancer., 2017, Aug, 6(4): 22-25.

Dauth et al., "Extracellular Matrix Protein Expression Is Brain Region Dependent", The Journal of Comparative Neurology, 2016, 524:1309-1336.

Ferrerosa et al., "IMMU-14. Synnotch Chimeric Antigen Receptor (CAR) T-Cells as a Potential Treatment for Diffuse Intrinsic Pontine Glioma (DIPG)/Diffuse Midline Glioma (DMG)", Jun. 2022, 24(Suppl 1): i84, doi: 10.1093/neuonc/noac079.307.

Mao et al., "Updates On Chimeric Antigen Receptor-Mediated Glioblastoma Immunotherapy", Rhode Island Medical Journal, 2017, 100(6): 39-42.

Nakagawa et al., "Identification of glioblastoma-specific antigens expressed in patient-derived tumor cells as candidate targets for chimeric antigen receptor T cell therapy", Neuro-Oncology Advances, Nov. 15, 2022, 5(1): 1-9.

Nehama et al., "B7-H3-redirected chimeric antigen receptor T cells target glioblastoma and neurospheres", EBioMedicine, 2019, 47: 33-43.

Razpotnik et al., "Targeting Malignant Brain Tumors with Antibodies", Frontiers in Immunology, 2017, 8(1181), pp. 1-14.

Shraibman et al., "Identification of Tumor Antigens Among the HLA Peptidomes of Glioblastoma Tumors and Plasma", Molecular & Cellular Proteomics, Jun. 2019, 18(6): 1255-1268.

Szeto et al., "TCR Recognition of Peptide-MHC-I: Rule Makers and Breakers", International Journal of Molecular Sciences, Dec. 2020, 22(1):68, 26 pages.

Wang et al., "Identification of tumor-associated antigens and immune subtypes of lower-grade glioma and glioblastoma for mRNA vaccine development", Chinese Neurosurgical Journal, Oct. 28, 2022, 8:34, 14 pages.

Watchmaker et al., "EXTH-33. Priming of Synnotch CAR T Cells Via CNS-Specific Antigen Allows Spatial and Temporal Regulation of Car Expression, Effective Homing and Persistence of T Cells in the Cns", Neuro-Oncology, Nov. 2022, vol. 24, Issue Supplement_7, Nov. 2022, Page vii216, https://doi.org/10.1093/neuonc/noac209.831.

Wu et al., "Tumor antigens and immune subtypes of glioblastoma: the fundamentals of mRNA vaccine and individualized immunotherapy development", Journal of Big Data, Jul. 14, 2022, 9:92, 25 pages.

Yamada et al., "Molecular Cloning of Brevican, a Novel Brain Proteoglycanof the Aggrecadersican Family", The Journal of Biological Chemistry, 1994, 269(13): 10119-10126.

Yang et al., "Targeting EGFRvlll for glioblastoma multiforme", Cancer Letters, 2017, 403: 224-230.

Yang et al., "T cells expressing NKG2D chimeric antigen receptors efficiently eliminate glioblastoma and cancer stem cells", Journal for ImmunoTherapy of Cancer, 2019, 7:171, 13 pages.

Montano et al., "Expression of EGFRvlll in Glioblastoma: Prognostic Significance Revisited", Neoplasia, 2011, 13(12): 1113-1121.

Sattiraju et al., "IL13RA2 targeted alpha particle therapy against glioblastomas", Oncotarget, 2017, 8(26): 42997-43007.

Chow et al., "T Cells Redirected to EphA2 for the Immunotherapy of Glioblastoma", Molecular Therapy, 2013, 21(3): 629-637.

Migliorini et al. (2018) "CART-Cell Therapies in Glioblastoma: A First Look" Clinical Cancer Research, 24(3): 535-540.

O'Rourke et al. (2017) "A single dose of peripherally infused EGFRvlll-directed CART cells mediates antigen loss and induces adaptive resistance in patients with recurrent glioblastoma" Science Translational Medicine, 9(399):1-15.

Johnson et al., "Rational development and characterization of humanized anti-EGFR variant III chimeric antigen receptor T cells for glioblastoma", Science Translational Medicine, 2015, 7(275): 1-16.

(56) References Cited

OTHER PUBLICATIONS

Bielamowicz et al., "Trivalent CAR T cells overcome interpatient antigenic variability in glioblastoma", Neuro-Oncology, 2017, 20(4): 506-518.
Bielamowicz et al., "Trivalent CAR T cells overcome interpatient antigenic variability in glioblastoma", Neuro-Oncology, 2017, 20(4), Supplemental Tables 1-3.
Dutoit et al., "Exploiting the glioblastoma peptidome to discover novel tumour-associated antigens for immunotherapy", Brain, 2012, 135: 1042-1054.
Genbler et al., "Dual targeting of glioblastoma with chimeric antigen receptor-engineered natural killer cells overcomes heterogeneity of target antigen expression and enhances antitumor activity and survival", ONCOIMMUNOLOGY, 2016, 5(4): e1119354, 12 pages.
Hegde et al., "Combinational Targeting Offsets Antigen Escape and Enhances Effector Functions of Adoptively Transferred T Cells in Glioglastoma", Molecular Therapy, 2013, 21(11): 2087-2101.
Suryadevara et al., "Are BiTEs the "missing link" in cancer therapy?", OncoimmunologY, 2015, 4(6): e1008339, 10 pages.
Lohmueller et al., "Current modalities in cancer immunotherapy: immunomodulatory antibodies, CARs and vaccines", Pharmacol Ther., Oct. 2017, 178: 31-47.
Morello et al., "Mesothelin-Targeted CARs: Driving T cells to Solid Tumors", Cancer Discov., Feb. 2016, 6(2): 133-146.
Watanabe et al., "Expanding the Therapeutic Window for CAR T Cell Therapy in Solid Tumors: The Knowns and Unknowns of CAR T Cell Biology", Frontiers in Immunology, Oct. 2018, 9:2486.
Jarboe et al., "Expression of Interleukin-13 Receptor α2 in Glioblastoma Multiforme: Implications for Targeted Therapies", Cancer Res, Sep. 2007; 67(17): 7983-7986.
Roybal et al., "Precision Tumor Recognition by T Cells With Combinatorial Antigen-Sensing Circuits", Cell, Feb. 2016, 164: 770-779.
Wykosky et al., "Interleukin-13 Receptor a2, EphA2, and Fos-Related Antigen 1as Molecular Denominators of High-Grade Astrocytomas and Specific Targets for Combinatorial Therapy", Clin Cancer Res, Jan. 2008, 14(1): 199-208.
Allen et al., "Expression of epidermal-growth-factor receptor in the K562 cell line by transfection", Biochem. J., 1990, 271: 785-790.
Oh et al., "Targeting EGFR and uPAR on human rhabdomyosarcoma, osteosarcoma, and ovarian adenocarcinoma with a bispecific ligand-directed toxin", Clinical Pharmacology: Advances and Applications, 2018, 10: 113-121.
Hegde et al., "Tandem Car T cells targeting HER2 and IL13Ra2 mitigate tumor antigen escape", The Journal of Clinical Investigation, 2016, 126(8): 3036-3052.
Ferluga et al., "Simultaneous targeting of Eph receptors in glioblastoma", Oncotarget, Aug. 1, 2016, 7(37): 59860-59876.
Huang et al., "The CRISPR/Cas9 system targeting EGFR exon 17 abrogates NF-KB activation via epigenetic modulation of UBXN1 in EGFRwt/vlll glioma cells", Cancer Letters, 2017, 388: 269-280.
Lim et al.; U.S. Appl. No. 19/566,829, filed Mar. 13, 2026, "Methods of Treating Glioblastomas".
Bonavia et al., "EGFRvlll promotes glioma angiogenesis and growth through the NF-KB, interleukin-8 pathway", Oncogene. 2012, 31(36): 4054-4066.
Brown et al., "Regression of Glioblastoma after Chimeric Antigen Receptor T-Cell Therapy", The New England Journal of Medicine, 2016, 375(26): 2561-2569.
Cameron et al., "Identification of a Titin-derived HLA-A1-presented peptide as a cross-reactive target for engineered MAGE A3-directed T cells", Sci Transl Med, 2013, 5, 197ra103.
Choi et al., "CAR-T cells secreting BiTEs circumvent antigen escape without detectable toxicity", Nature Biotechnology, 2019, 37: 1049-1058.
Drumm et al., "Extensive brainstem infiltration, not mass effect, is a common feature of end-stage cerebral glioblastomas", Neuro-Oncology, Nov. 10, 2019, 22(4), 470-479.
Goldgur et al., "Generation and characterization of a single-chain anti-EphA2 antibody", Growth Factors, 2014, 32(6): 214-222.
Heimberger et al., "Prognostic effect of epidermal growth factor receptor and EGFRvlll in glioblastoma multiforme patients", Clinical Cancer Research, 2005, 11: 1462-1466.
Johnson et al., "Gene therapy with human and mouse T-cell receptors mediates cancer regression and targets normal tissues expressing cognate antigen", Blood, 2009, 114: 535-546.
June et al., "Chimeric Antigen Receptor Therapy", N Engl J Med, 2018, 379(1): 64-73.
Kahlon et al., "Specific recognition and killing of glioblastoma multiforme by interleukin 13-zetakine redirected cytolytic T cells", Cancer Research, 2004, 64: 9160-9166.
Krebs et al., "T cells redirected to IL13Ra2 with IL13 mutein-CARs have antiglioma activity but also recognize IL13Ra1", Cytotherapy, 2014, 16(8): 1121-1131.
Morgan et al., "Cancer regression and neurological toxicity following anti-MAGE-A3 TCR gene therapy", J Immunother, 2013, 36(2): 133-151.
Morgan et al., "Case Report of a Serious Adverse Event Following the Administration of T Cells Transduced With a Chimeric Antigen Receptor Recognizing ERBB2", Molecular Therapy, 2010, 18(4): 843-851.
Morsut et al., "Engineering Customized Cell Sensing and Response Behaviors Using Synthetic Notch Receptors", Cell, 2016, 164: 780-791.
Moscatello et al., "Frequent expression of a mutant epidermal growth factor receptor in multiple human tumors", Cancer Research, 1995, 55: 5536-5539.
Ohno et al., "Expression of miR-17-92 enhances anti-tumor activity of T-cells transduced with the anti-EGFRvlll chimeric antigen receptor in mice bearing human GBM xenografts", Journal for ImmunoTherapy of Cancer 2013, 1:21.
Parkhurst et al., "T cells targeting carcinoembryonic antigen can mediate regression of metastatic colorectal cancer but induce severe transient colitis", Mol Ther, 2011, 19(3): 620-626.
Roybal et al., "Engineering T Cells with Customized Therapeutic Response Programs Using Synthetic Notch Receptors", Cell, 2016, 167, 419-432.
Sampson et al., "Immunologic Escape After Prolonged Progression-Free Survival With Epidermal Growth Factor Receptor Variant III Peptide Vaccination in Patients With Newly Diagnosed Glioblastoma", Journal of Clinical Oncology, 2010, 28(31): 4722-4729.
Shahideh et al., "Systematic review of primary intracranial glioblastoma multiforme with symptomatic spinal metastases, with two illustrative patients", Journal of Clinical Neuroscience, 2012, 19: 1080-1086.
Thorne et al., "Epidermal growth factor receptor targeting and challenges in glioblastoma", Neuro-Oncology, 2016, 18(7): 914-918.
Wikstrand et al., "Cell surface localization and density of the tumor-associated variant of the epidermal growth factor receptor, EGFRvlll", Cancer Res, 1997, 57: 4130-4140.
Wykosky et al., "EphA2 as a novel molecular marker and target in glioblastoma multiforme", Mol Cancer Res, 2005, 3(10): 541-551.

* cited by examiner

USE OF BRAIN-SPECIFIC ANTIGENS TO HOME, BLOCK AND DELIVER CELL-BASED TREATMENTS TO THE BRAIN

CROSS-REFERENCING

This application is a § 371 national phase of International Application No. PCT/US2020/059368, filed on Nov. 6, 2020, which claims the benefit of U.S. provisional application Ser. No. 62/980,885, filed on Feb. 24, 2020, which applications are incorporated by reference herein.

STATEMENT REGARDING FEDERALLY SPONSORED RESEARCH

This invention was made with government support under grant nos. RO1 CA196277 awarded by the National Institutes of Health. The government has certain rights in the invention.

INTRODUCTION

Although some cell therapies have demonstrated remarkable therapeutic responses and benefits for patients with some disease, development of effective cell-based therapies for other disease remains a challenge, in large part due to the difficulty in delivering therapeutics only to a specific tissue. For example, some treatments for brain disorders may be detrimental to non-brain tissues. As such, administrating a therapy that targets diseased cells in one tissue can often cause side-effects in another. This issue is often particularly problematic for cell-based therapies because many of those therapies are very potent. The clinical use of such therapies is therefore often limited by the off-site affects, rather than the on-site effects.

In order to avoid off-site effects, it would be desirable to a deliver therapeutic payload (a cytokine, an antibody, or a chimeric antigen receptor, for example) to a particular tissue. This disclosure addresses this issue, particularly for the brain.

SUMMARY

Provided herein is a cell comprising a recombinant nucleic acid encoding a transmembrane protein that has an extracellular binding domain that specifically binds to a brain-selective extracellular antigen, e.g., MOG, CDH10, PTPRZ1 or NRCAM, wherein the cell does not comprise a nucleic acid encoding an antigen-specific therapeutic that binds to a killing antigen expressed by a glioblastoma. MOG, CDH10, PTPRZ1 or NRCAM are brain-selective and, as such, binding to any of these antigens limits or concentrates the cell's effect to the brain. For example, in some embodiments, the transmembrane protein may cause therapeutic cells to localize the brain, thereby limiting migration of the therapeutic cells from the brain into other tissues. In other embodiments, the transmembrane protein may be a receptor, including but not limited to binding-triggered transcriptional switches, as exemplified by synNotch receptors. In these embodiments, the cell may further comprise a nucleic acid comprising: (i) a coding sequence encoding a therapeutic protein and (ii) a regulatory sequence, wherein the regulatory sequence is operably linked to the coding sequence and is responsive to activation of the binding-triggered transcriptional switch. In these embodiments, the therapeutic protein is expressed or delivered to brain tissue and not other tissues because the binding-triggered transcription switch is preferentially activated in the brain.

(a) Limitations of standard CAR T cell in heterogeneous tumors. One of the main challenges in identifying ideal CAR antigen for glioblastoma is targeting CAR T cells to antigen that is both highly specific and homogeneously expressed. If CAR T cell is targeted against a tumor-specific antigen (e.g. EGFRvIII), but expression of the antigen is heterogeneous (not in all tumor cells), then non-antigen expressing tumor cells can escape treatment. On the other hand, if the CAR T cell is targeted against a tumor antigen that is homogeneously expressed in tumor, but has imperfect specificity (also expressed in some normal cells), this will lead to on-target, off-tumor toxicity. The dual challenges of heterogeneity and specificity inherently limit the therapeutic window for CAR T cells.

(b) T cell circuits could be designed to combine recognition of two imperfect but complementary antigens: one specific and one homogeneous. Our approach is to engineering T cells that use a sequential, prime-and-kill mechanism: the T cells are first primed by antigen A (either a highly specific antigen or tissue-specific antigen) in order to induce the expression of CAR targeting antigen B, which is homogeneous but not necessary absolutely tumor specific. By applying a specificity pre-filter over a less constrained killing mechanism, these combinatorial antigen recognition circuits may enable the engineered T cells to overcome tumor antigen heterogeneity while also eliminating on-target, off-tumor toxicity.

Figure 6:
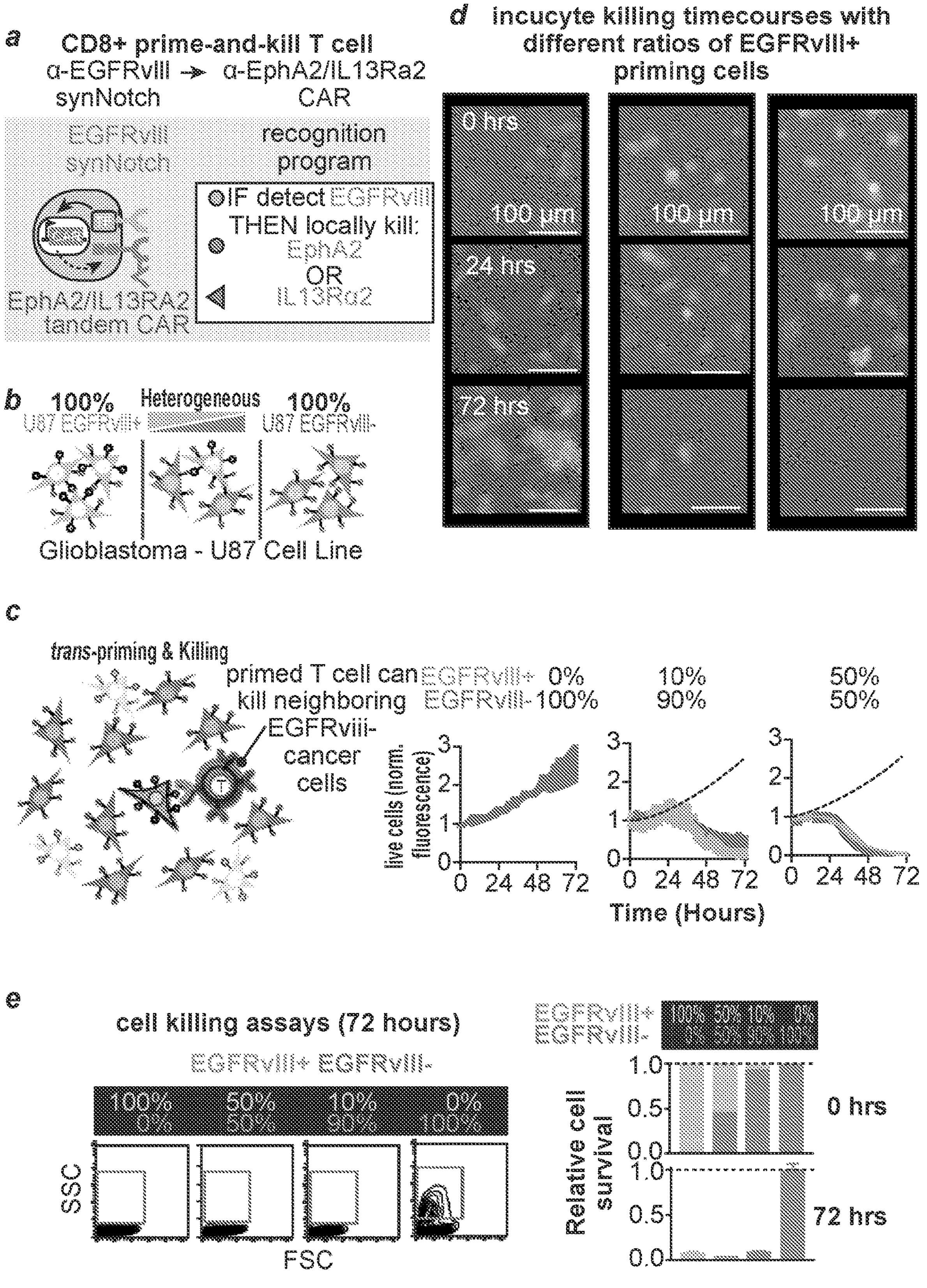

FIG. 6 shows that CD8+ T cells with α-EGFRvIII synNotch→α-EphA2/IL13α2 CAR prime-and-kill circuit can effectively kill U87 GBM populations with heterogeneous EGFRvIII expression in vitro.

Figure 11:
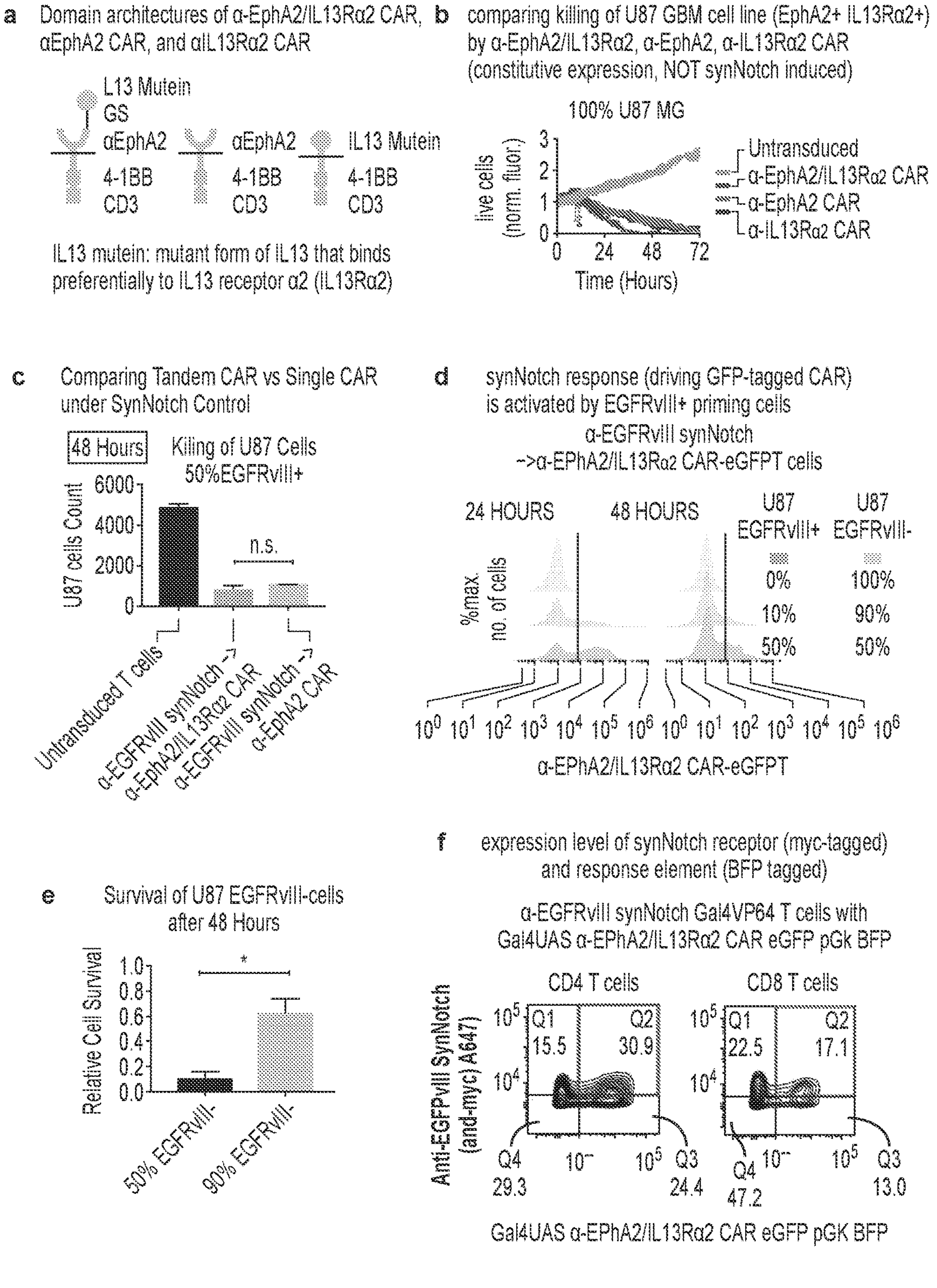

(a) Primary human CD8+ T cells were engineered with the α-EGFRvIII synNotch receptor and the corresponding response elements controlling expression of α-EphA2/IL13α2 4-1BBζ CAR expression ("EphA2/IL13 mutein CAR", FIG. 11 *a*). IL13 mutein is a mutant form of IL13 (E13K, K105R) that preferentially binds to IL13Rα2 (Krebs et al., 2014). The primary T cells must first recognize EGFRvIII via their synNotch receptor in order to initiate CAR expression. The prime-and-kill CAR T cells should only activate to kill EphA2+ or IL13Rα2+ target cells when exposed to EGFRvIII-positive cells.

(b) We mimic the heterogeneity observed in GBM using engineered U87 GBM cell lines. U87 cells naturally express the two target antigens EphA2 and IL13Rα2, but not EGFRvIII (U87-EGFRvIII-negative cells—here also referred to as "target" cells). We engineered U87 cells that also express the EGFRvIII priming antigen (U87-EGFRvIII-positive cells—here also referred to as "priming" cells). We can systematically generate different levels of heterogeneity by mixing these U87 cells in different ratios. Tumor cells were labelled with different fluorescencent proteins to allow tracking of cell survival for each individual cell type.

(c) The "prime-and-kill" T cell circuit can overcome tumor heterogeneity. The prime-and-kill circuit utilizes a synNotch receptor to recognize a priming antigen (gold), which in turn induces the expression of a CAR that recognizes a different killing antigen (blue). We hypothesize that local priming of the T cells in the tumor may allow for killing of neighboring tumor cells that lack the priming antigen (blue). Thus, a specific but heterogeneously expressed antigen could serve as a good priming antigen, while a homogeneous but not absolutely tumor-specific antigen could serve as a good killing antigen. In this model, other normal tissues that express the killing antigen would be spared, as long as the priming antigen was not expressed.

(d) Time-lapse analysis of killing different heterogeneous tumor cell ratios. Primary CD8+ human T cells with the α-EGFRvIII synNotch→α-EphA2/IL13α2 CAR were cultured with the indicated U87 cell mixtures at an E:T ratio of 5:1 and imaged over 3 days using an IncuCyte system. EGFRvIII-positive priming cells are colored in yellow, while EGFRvIII-negative target cells are colored in blue (T cells are unlabeled). Dotted black line shows the growth of 100% target cells only as a reference. Data from these experiments (cell survival measured by fluorescence) is quantitatively analyzed in the time course plots below (n=3, error bars are SEM).

(e) Cytotoxicity assays using primary CD8+ prime-and-kill CAR T cells. Primary CD8+ prime-and-kill CAR T cells described in FIG. 6 *a* were co-cultured with U87 cells described in FIG. 6 *b*. Forward and side scatter flow cytometry plots (at the 72-hr timepoint) are shown. The live U87 cells fall within the red gate. The prime-and-kill CAR T cells only kill the U87 population when the priming cells are found within the population, shown by the reduction of cells in the U87 gate (representative of three experiments). Quantification of prime-and-kill CAR T cell killing as a function of priming/target cell ratio (n=3, error bars are SEM).

Figure 7:
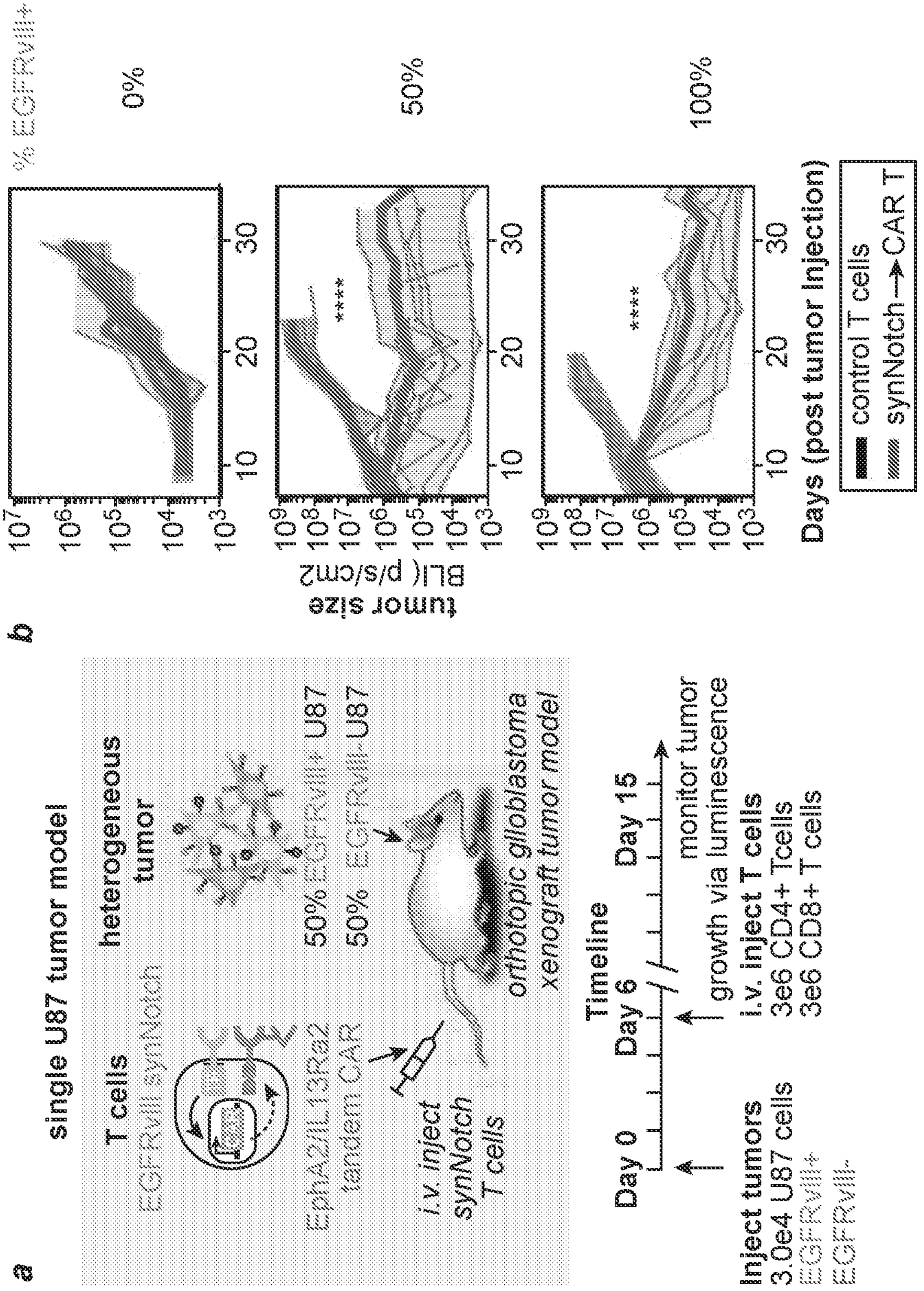
Figure 7:
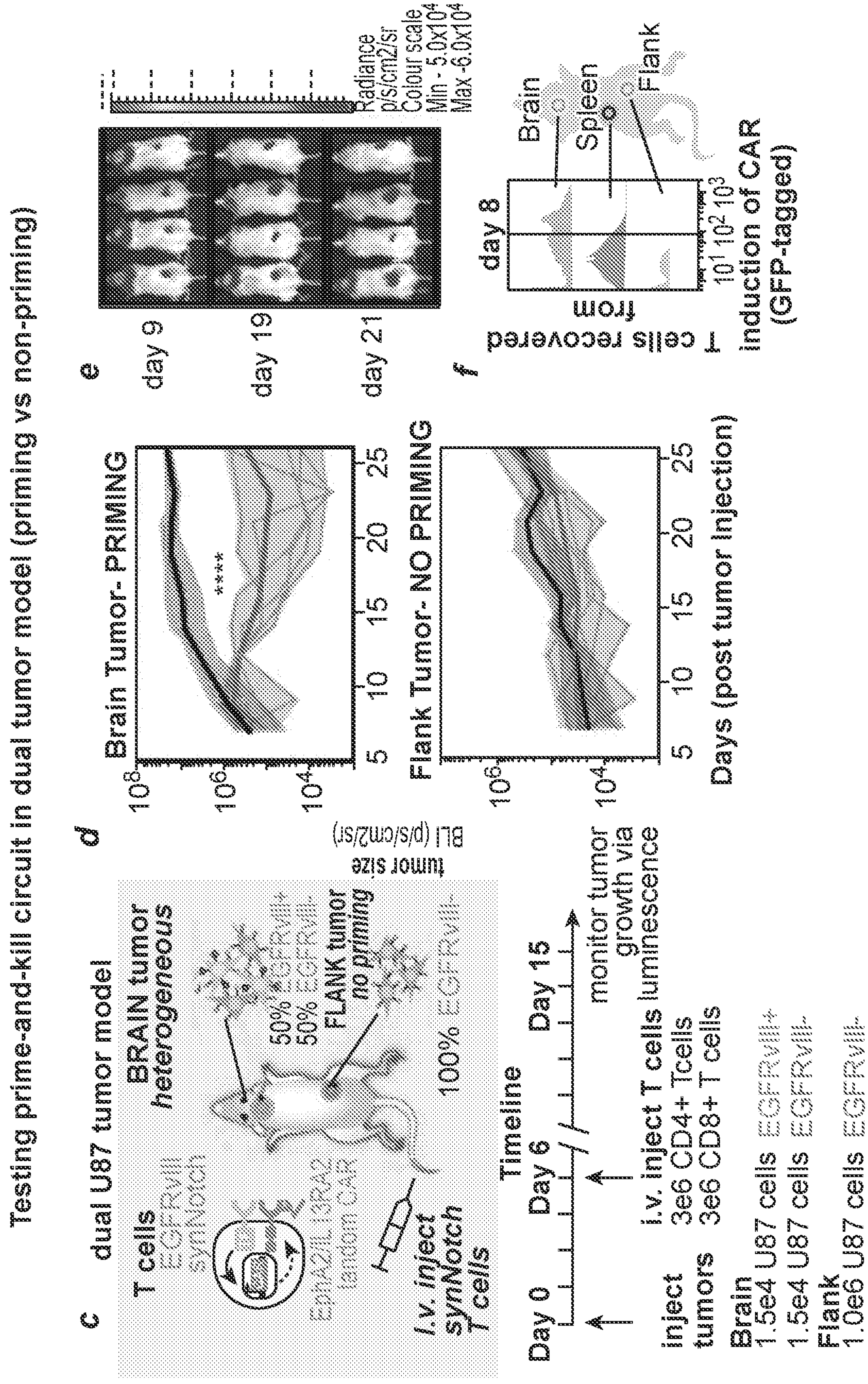

FIG. 7 shows that T cells with α-EGFRvIII synNotch→α-EphA2/IL13α2 prime-and-kill circuit mediate effective and localized anti-tumor response against U87 GBM that heterogeneously express EGFRvIII in the brain.

(a) Immunodeficient NCG mice were orthotopically implanted in the brain with U87 GBM xenograft. Tumors contained one of the following three priming/target cell ratios: i) 100% U87 (EGFRvIII-negative) target tumor cells, ii) 50%/50% of U87-EGFRvIII-positive (priming) and EGFRvIII-negative (target) tumor cells, and iii) 100% U87-EGFRvIII-positive (priming) cells. Tumor cells were engineered to express luciferase to allow for tracking of tumor size. Six days following tumor implantation, the mice were infused intravenously with 3 million each of CD4+ and CD8+T cells. T cells expressed either: i) no construct (non-transduced control) or ii) α-EGFRvIII synNotch→α-EphA2/IL13α2 CAR circuit.

(b) Tumor size was determined by longitudinal bioluminescence imaging. Individual traces for each animal are shown with thin lines, while average is shown with the thick line. Negative control treatment with non-transduced T cells is shown in black, prime-and-kill CAR T cell treatment is shown in pink. Prime-and-kill CAR T cells have no impact on tumors that lack EGFRvIII priming (left panels, n=5), but show significant improvement in reducing tumor size (**** $p<0.0001$, t test).

(c) NCG mice were simultaneously implanted with two tumors: i) heterogeneous tumor comprising EGFRvIII-positive U87 and EGFRvIII-negative U87 cells in 1:1 ratio in the brain, ii) subcutaneous EGFRvIII-negative U87 tumor cells in the flank. Thus, both tumors express the killing antigens (EphA2 and IL13Rα2) but differ in expression of the EGFRvIII priming antigen. Mice were treated one time (6 days after tumor implantation) with intravenous infusion of non-transduced (n=6), or prime-and-kill CAR T cells (n=6).

(d) Tumor size was measured by luciferase luminescence. Prime-and-kill CAR T cells are shown in pink while the non-transduced control T cells are shown in gray. Significant suppression in the size of brain tumor was observed in prime-and-kill CAR T cell treated mice (**** $p<0.00001$; t test) while the flank tumor grew at the same rate as in the mice treated with non-transduced T cells.

(e) Bioluminescence imaging over time for mice with heterogeneous U87 (1:1 mix of EGFRvIII-positive and EGFRvIII-negative) tumor cells, treated with prime-and-kill CAR T cells. Each column represents one mouse; each row represents time point of imaging.

(f) Tumor-bearing mice were euthanized two days after prime-and-kill CAR T cell infusion. Flow cytometry was performed on T cells isolated from intracranial heterogeneous tumor, spleen and control flank tumor. Engineered T cells that have been primed by EGFRvIII antigen will be positive for GFP (CAR is fused to GFP). Upregulation of GFP expression in T cells (CD3+) was only observed in the brain xenograft and not in T cells isolated from the flank tumor and spleen.

Figure 8:
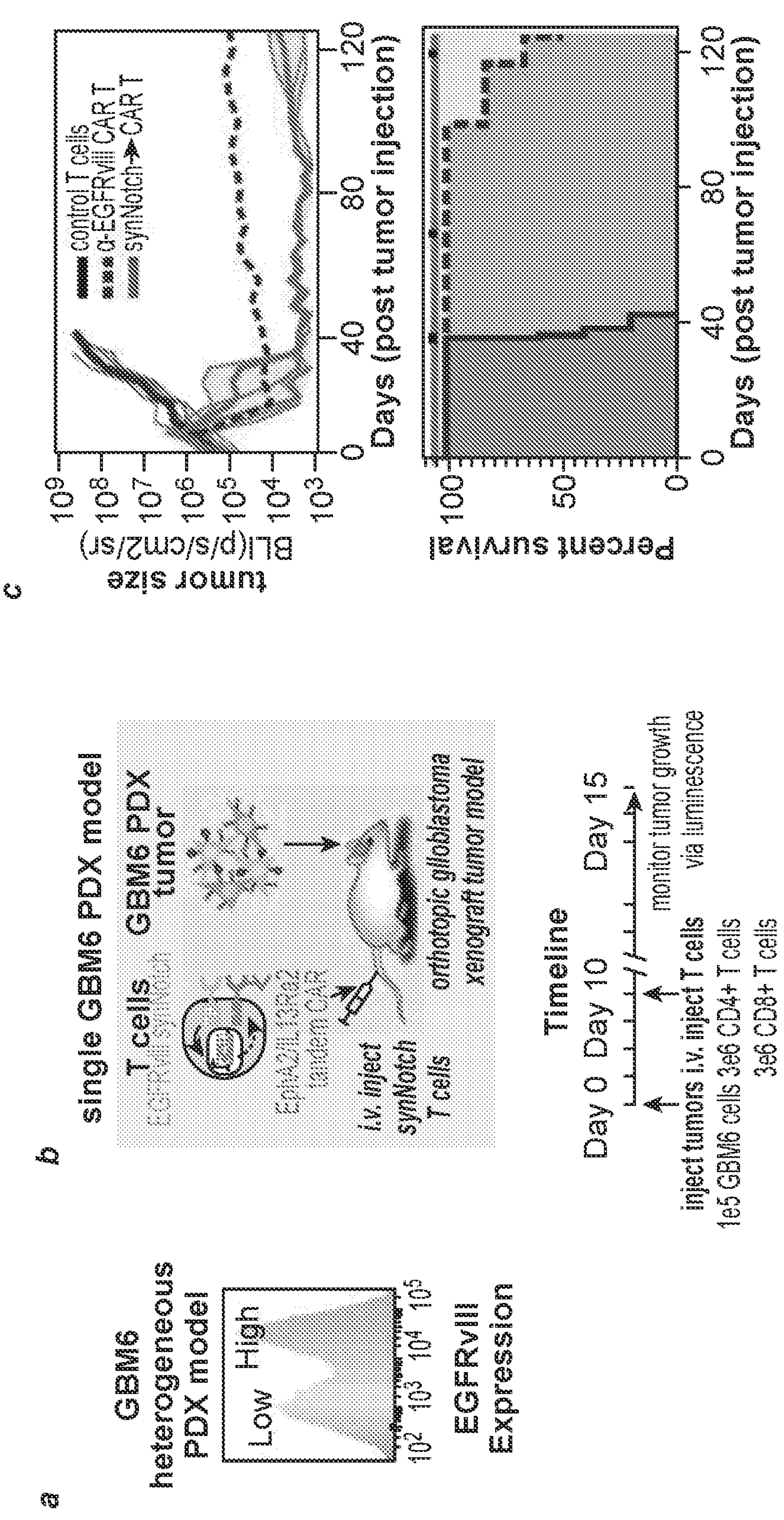
Figure 8:
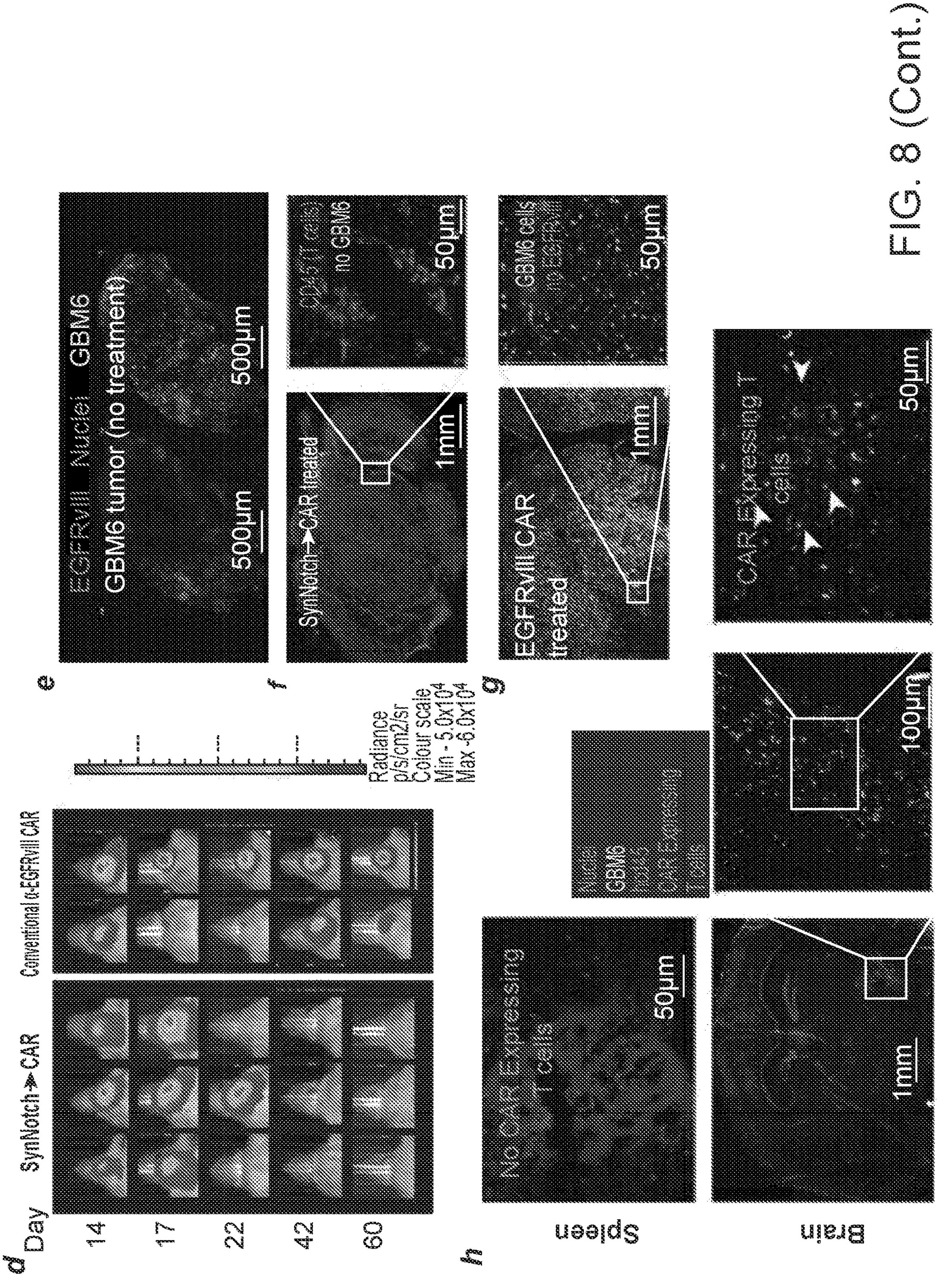

FIG. 8 shows that T cells with α-EGFRvIII synNotch→α-EphA2/IL13α2 CAR prime-and-kill circuit durably clear patient-derived GBM6 xenograft tumors in mice despite heterogeneous EGFRvIII expression.

(a) Endogenous expression of EGFRvIII in patient-derived xenograft GBM6 cells is heterogeneous.

(b) Immunodeficient NCG mice were orthotopically implanted in the brain with GBM6 patient-derived xenograft cells. Tumor cells were engineered to express mCherry and luciferase to allow for tracking of tumor size. EGFRvIII expression on GBM6 cells is heterogeneous. Ten days following tumor implantation, the mice were infused intravenously with 3 million each of CD4+ and CD8+T cells. T cells expressed either: i) no construct (non-transduced control) (n=5), ii) α-EG- FRvIII synNotch→α-EphA2/IL13α2 CAR circuit (n=7), or iii) constitutively expressed α-EGFRvIII CAR (n=6).

Figure 13:
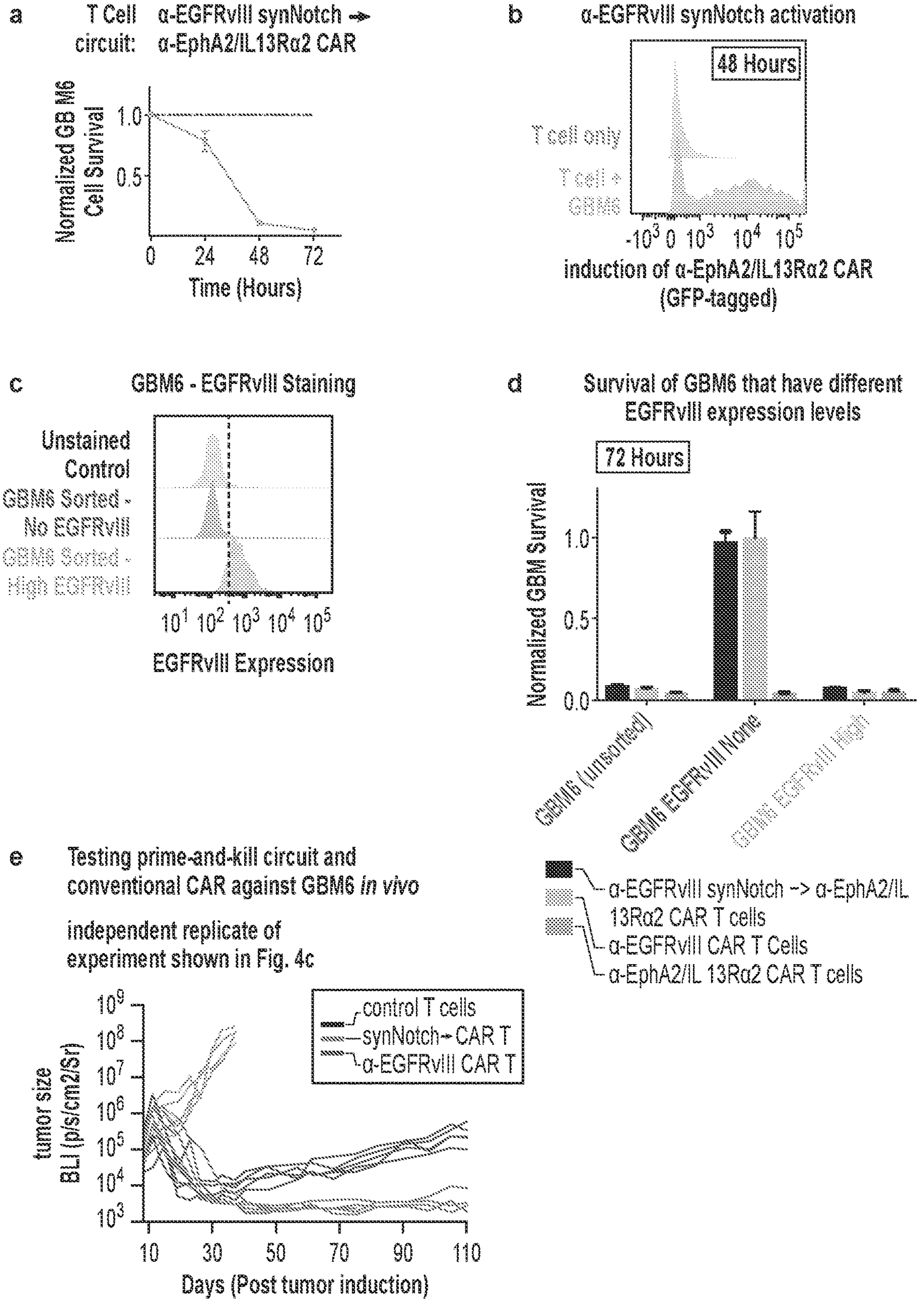

(c) Tumor size (top row) and survival (bottom row) over time. Tumor size was determined by longitudinal bioluminescence imaging. Individual traces for each animal are shown with thin lines, while average is shown with the thick line. Negative control treatment with non-transduced T cells is shown in black, prime-and-kill CAR circuit treatment is shown in pink, and conventional α-EGFRvIII CAR treatment (average only for clarity) is shown in purple dotted line. Treatment with conventional α-EGFRvIII CAR T cells resulted in early tumor regression followed by recurrence in all mice (n=6) with tumor-induced death of 2 mice by day 117. In contrast, all mice treated with the prime-and-kill CAR T cells showed complete clearance of tumor ($p<0.0001$ t-test untransduced vs prime-and-kill CAR T cells). These mice survived for more than 125 days, except for two mice that were euthanized because of unrelated infection. An independent replicate of this experiment is shown in FIG. 13 *e*.

(d) Longitudinal bioluminescence imaging for GBM6 bearing mice treated with prime-and-kill CAR T cells and conventional α-EGFRvIII CAR T cells. Each column represents one mouse; each row represents time point of imaging.

(e) Representative fluorescence microscopy of GBM6 xenograft shows heterogeneous expression of EGFRvIII (red) 10 days post tumor inoculation (mCherry tumor).

(f) Fluorescent microscopy reveals clearance of engrafted GBM6 xenograft (lack of mCherry tumor cells) following systemic administration of synNotch-CAR T cells. Retention of prime-and-kill CAR T cells (stained for CD45, in red) in the brain parenchyma and meninges.

(g) Representative image of tumor recurrence (mCherry positive tumor cells) and loss of EGFRvIII expression (in red) for conventional α-EGFRvIII CAR T cell treated xenograft.

(h) Representative confocal fluorescent microscopy of prime-and-kill CAR T cell treated GBM6 xenograft reveal primed GFP+ T cells (colocalized with hCD45 stain in red, indicated by white arrow) in the tumor bed (yellow). Prime-and-kill CAR T cells express GFP upon priming. Right panel. Prime-and-kill CAR T cells (red) in the spleen do not express GFP.

Figure 9:
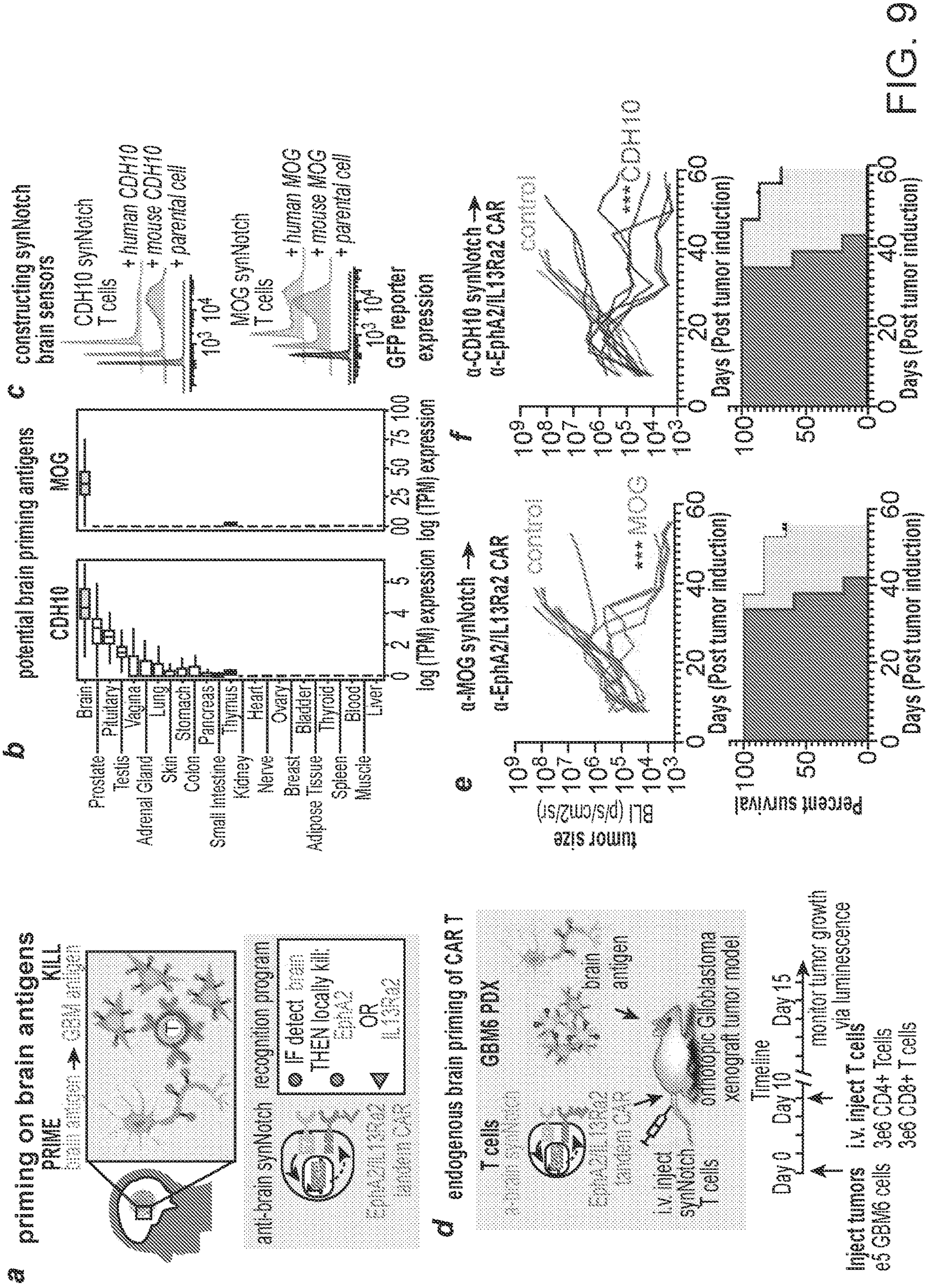
Figure 9:
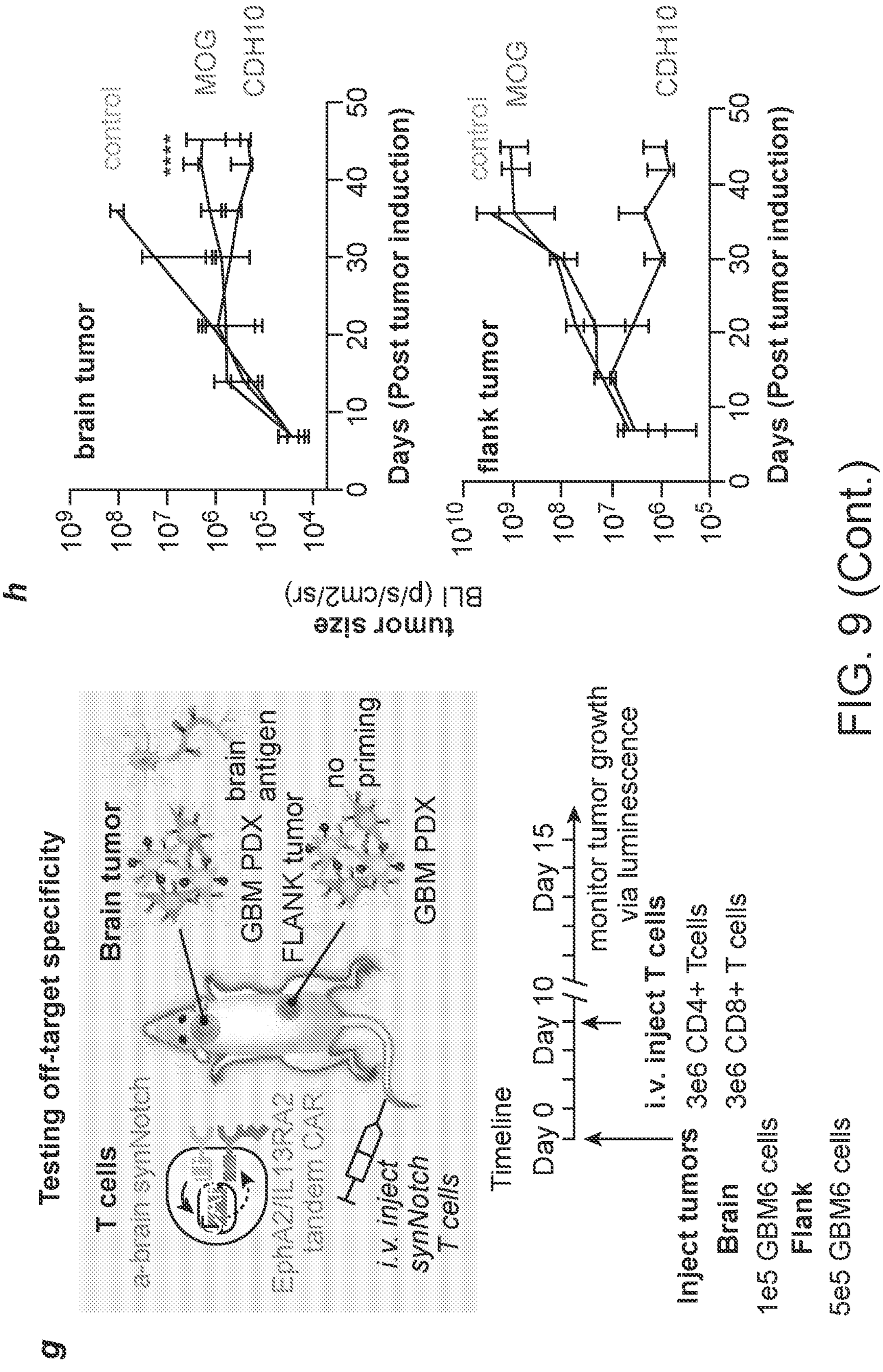

FIG. 9 shows that local brain-specific prime-and-kill CAR T cells mediate effective anti-GBM responses.

(a) Primary human CD8+ T cells were engineered with the anti-brain antigen synNotch receptor and the corresponding response elements controlling expression of α-EphA2/IL13α2 4-1BBζ CAR expression ("EphA2/IL13 mutein CAR", FIG. 11 *a*). The primary T cells must first recognize the brain antigen via their synNotch receptor in order to initiate CAR expression. The prime-and-kill circuit should only activate to kill EphA2+ or IL13Ra2+ target cells only when it is exposed to brain.

(b) Box and whisker plots showing tissue specific expression of CDH10 and MOG across a subset of tissue samples in GTEx v7. Units shown are log scaled normalized RNAseq counts (Transcripts Per Million) taken from GTEx portal v7.

(c) Primary CD8+α-CDH10 or α-MOG synNotch→GFP PGK BFP T cells were co-cultured with either parental K562 or K562 transduced to express mouse CDH10 or MOG or human CDH10 or MOG. T cell priming after 48-hour exposure was measured by induction of GFP reporter. FACS histograms show induction of GFP reporter only in the presence of mouse CDH10+ or MOG+ or human CDH10+ or MOG+K562 and not K562 parental cells (representative of 3 experiments).

(d) Immunodeficient NCG mice were orthotopically implanted in the brain with GBM6 patient-derived xenograft cells. Tumor cells were engineered to express mCherry and luciferase to allow for tracking of tumor size. Ten days following tumor implantation, the mice were infused intravenously with 3 million each of CD4+ and CD8+T cells. T cells expressed either: i) no construct (non-transduced control), ii) α-MOG synNotch→α-EphA2/IL13α2 CAR circuit (n=6), or iii) α-CDH10 synNotch→α-EphA2/IL13α2 CAR circuit (n=7).

(e) Tumor size (top row) and survival (bottom row) over time. Tumor size was determined by longitudinal bioluminescence imaging. Negative control treatment with non-transduced T cells is shown in grey, prime-and-kill CAR circuit treatment is shown in pink. Compared to non-transduced treatment group, mice treated with the α-MOG-prime-and-kill CAR T cells (4 out of 6 mice) showed strong anti-tumor response ($p<0.001$ by t test with Holm-Sidak correction for multiple comparisons) and survived for 60 days ($p=0.05$ Log-rank (Mantel-Cox) test).

(f) Tumor size (top row) and survival (bottom row) over time. Tumor size was determined by longitudinal bioluminescence imaging. Negative control treatment with non-transduced T cells is shown in grey, prime-and-kill CAR circuit treatment is shown in purple. Compared to non-transduced treatment group, mice treated with the α-CDH10-prime-and-kill CAR T cells (5 out of 7 mice) showed sustained anti-tumor response ($p<0.001$ by t test with Holm-Sidak correction for multiple comparisons) ($p<0.0001$ Log-rank (Mantel-Cox) test.

(g) GBM6 PDX tumor cells were implanted in the brain and flank of NCG mice. Both tumors express the killing antigens (EphA2 and IL13Rα2) however the expression of priming antigen MOG/CDH10 is restricted to the brain. Mice were treated one time (10 days after tumor implantation) with intravenous infusion of non-transduced (n=5), or α-MOG-prime-and-kill CAR T cells (n=6), or (iii) α-CDH10-prime-and-kill CAR T cells (n=5).

(h) Tumor size was measured by luciferase luminescence. α-MOG-prime-and-kill CAR T cells are shown in pink, α-CDH10-prime-and-kill CAR T cells are shown in purple while the non-transduced control T cells are shown in gray. Significant suppression in the size of brain tumor was observed in prime-and-kill CAR T cell treated mice (**** $p<0.0001$; t test) while the flank tumor grew at the same rate as in the mice treated with non-transduced T cells.

Figure 10:
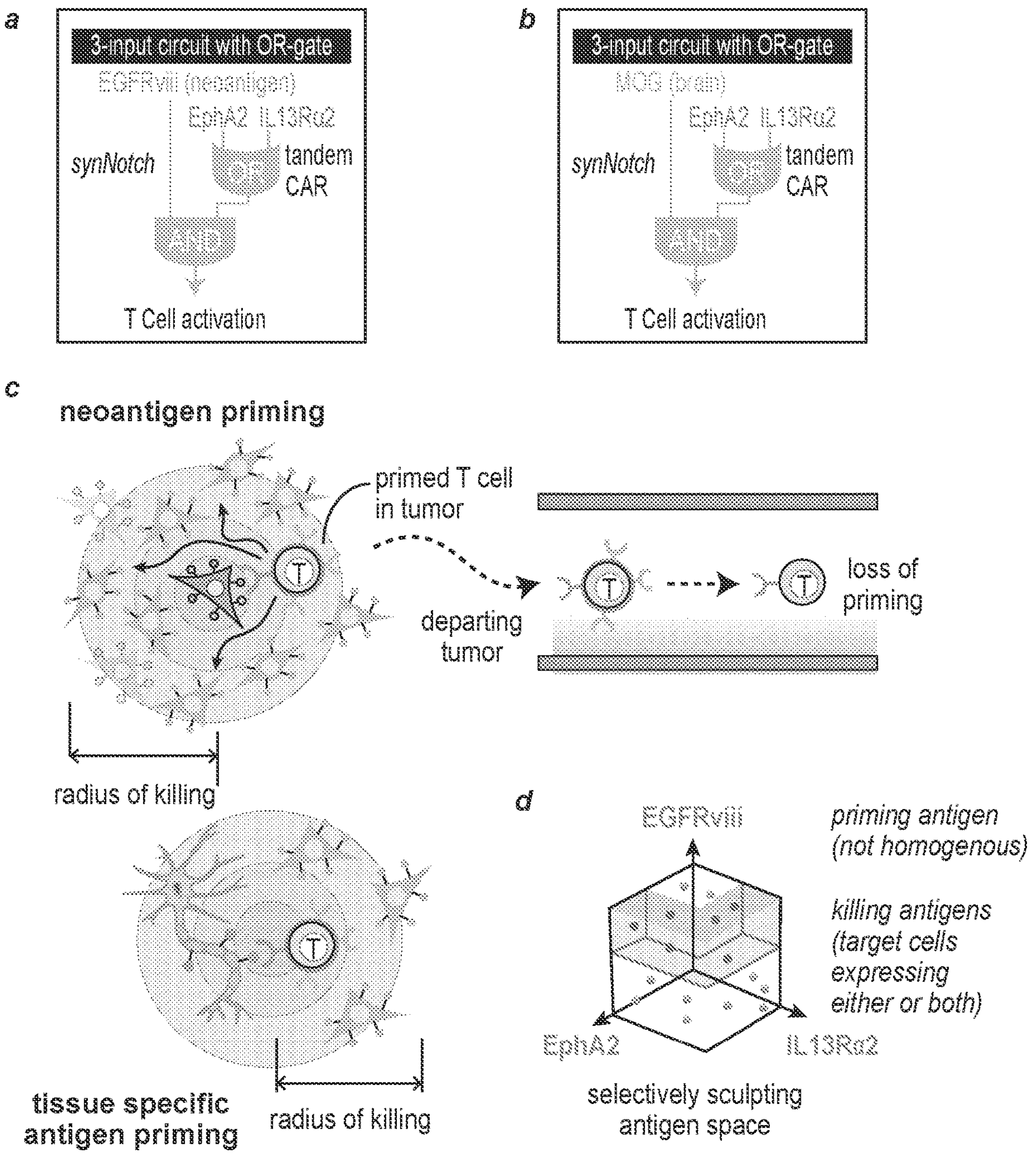

FIG. 10 shows that multi-antigen T cell circuits can be used to flexibly sculpt tumor recognition.

(a) and (b). The prime-and-kill circuit deployed here represents a 3 input AND-OR gate: killing activity will be induced when the T cells encounter the priming antigen EGFRvIII (a) or MOG (b) and either of the killing antigens (EphA2 or IL13Rα2).

(c). The prime-and-kill circuit is hypothesized to allow killing of target cells in a "killing radius" around priming cells (here EGFRvIII-positive cells). Once the T cells leave the tumor, and no longer receive continuous priming signals, the CAR expression decays over the course of a few hours, preventing a sustained killing response in other tissues (Roybal et al., 2016a; Roybal et al., 2016b).

(d). The prime-and-kill CAR circuit surgically carves antigen space to optimize capturing all tumor cells, while avoiding cross-reactivity. Here antigen space is represented in 3 dimensions, with 3 axes representing EGFRvIII or MOG as the priming antigen, EphA2 and IL13R$\alpha$2 as the killing antigens. The prime-and-kill CAR circuit selects for tumors that lie within the shade pink volume: the engineered T cells have to encounter EGFRvIII or MOG expressed in the brain tumor environment, and either EphA2 or IL13R$\alpha$2 expression on GBM cells.

FIG. 11 shows the design and testing of $\alpha$-EGFRvIII synNotch$\rightarrow$$\alpha$-EphA2/IL13R$\alpha$2 CAR T cells against U87 GBM.

(a) Domain architecture of $\alpha$-EphA2/IL13$\alpha$2 CAR, $\alpha$-EphA2 CAR, and $\alpha$-IL13R$\alpha$2 CAR. IL13 mutein is a mutant form of IL13 (E13K, K105R) that preferentially binds to IL13R$\alpha$2 (Krebs et al., 2014).

(b) Comparing killing of U87 wild-type cells (EphA2+ IL13R$\alpha$2+) by the new $\alpha$-EphA2/IL13$\alpha$2 CAR versus T cells expressing either an $\alpha$-EphA2 CAR or an $\alpha$-IL13R$\alpha$2 CAR. Killing was measured using fluorescently labelled U87 cells in an IncuCyte killing assay measuring total fluorescence (live cells) over time (n=3, error bars are SEM). The tandem CAR kills more rapidly and effectively than either individual target CAR at timepoints 24, 48, and 72 hours ($p \leq 0.0164$; Tukey's multiple comparisons test).

(c) The $\alpha$-EGFRvIII synNotch$\rightarrow$$\alpha$-EphA2/IL13R$\alpha$2 CAR is effective in killing 50/50% EGFRvIII-positive/EGFRvIII-negative co-cultures of U87 cells. The $\alpha$-EphA2/IL13$\alpha$2 CAR kills as effectively as T cells with similar circuit inducing $\alpha$-EphA2 CAR after 48 hours (n=3, error bars are SEM, p=not significant; t test).

(d) Primary CD8+ synNotch CAR T cells described in FIG. 7 *a* were co-cultured with U87 cells described in FIG. 7 *b*. T cell priming after 24-hour and 48-hour exposure was measured by tracking induction of $\alpha$-EphA2/IL13$\alpha$2 CAR fused with a GFP reporter. FACS histograms show no induction in the absence of priming cells, and significant induction with as low as 10% priming cells (EGFRvIII-positive) (representative of at least 3 independent experiments).

(e) Comparing relative cell survival of U87-EGFRvIII-negative 50% population and U87-EGFRvIII-negative 90% population co-cultured with $\alpha$-EGFRvIII synNotch$\rightarrow$$\alpha$-EphA2/IL13R$\alpha$2 CAR after 48-hour exposure. Survival was measured using fluorescently labeled U87 cells in an IncuCyte assay measuring total fluorescence (live cells) over time (n=3, error bars are SEM). The U87-EGFRvIII-negative 90% population had higher relative cell survival compared to the U87-EGFRvIII-negative 50% population (p=0.0149; t test).

(f) Representative contour plots showing expression of the $\alpha$-EGFRvIII synNotch Gal4VP64 receptor and the corresponding response elements regulating $\alpha$-EphA2/IL13R$\alpha$2 CAR 4-1BB$\zeta$ CAR GFP pGK BFP in primary CD4+ and CD8+ T cells. T cells positive for the synNotch receptor was stained through the myc-tag present on the synNotch receptor and the response element was selected based on BFP expression. The T cells in the red-boxed quadrant were sorted were sorted for in vitro and in vivo experiments.

Figure 12:
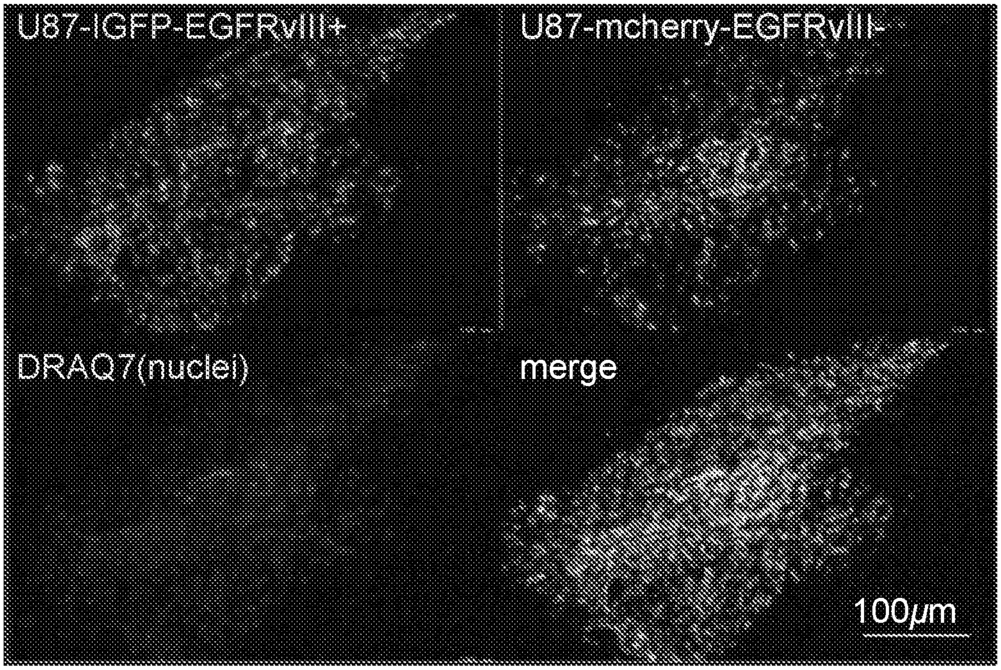

FIG. 12 shows representative immunofluorescent images of the 50/50% EGFRvIII-positive/EGFRvIII-negative U87 xenograft on day 6 following tumor cell inoculation. U87-EGFRvIII-positive and U87-EGFRvIII-negative cells are tagged with GFP and mCherry, respectively, and nuclei are stained with DRAQ7. Scale bar, 100 um. See methods for cell line generation.

FIG. 13 shows the results of testing $\alpha$-EGFRvIII synNotch$\rightarrow$$\alpha$-EphA2/IL13R$\alpha$2 CAR T cells against GBM6.

(a) Killing assays with primary CD8+$\alpha$-EGFRvIII synNotch$\rightarrow$$\alpha$-EphA2/IL13R$\alpha$2 CAR T cells with the circuit were co-cultured with GBM6 cells at 1:1 ET ratio. Relative cell survival over 72 hours was quantified and showed cytotoxicity capacity of synNotch CAR T cells to overcome GBM6 cell populations (n=3, error bars are SEM).

(b) Primary CD8+$\alpha$-EGFRvIII synNotch$\rightarrow$$\alpha$-EphA2/IL13R$\alpha$2 CAR T cells were co-cultured with or without GBM6 cells at 1:1 ET ratio. T cell priming after 48-hour exposure was measured by tracking induction of $\alpha$-EphA2/IL13R$\alpha$2 CAR fused with a GFP reporter. FACS histograms show no induction in the absence of GBM6 cells, and significant induction with GBM6 cells (representative of at least 3 independent experiments).

(c) GBM6 cell were sorted for varying level of EGFRvIII expression and evaluated by flow cytometry post-sort. Gray represents unstained control.

(d) Killing assays with primary CD8+$\alpha$-EGFRvIII synNotch$\rightarrow$$\alpha$-EphA2/IL13R$\alpha$2 CAR T cells, $\alpha$-EGFRvIII CAR T cells, or $\alpha$-EphA2/IL13R$\alpha$2 CAR T cells co-cultured with either none, high, or unsorted expression of EGFRvIII. Relative cell survival over 72 hours was quantified and showed inability of $\alpha$-EGFRvIII synNotch$\rightarrow$$\alpha$-EphA2/IL13R$\alpha$2 CAR T cells and $\alpha$-EGFRvIII CAR T cells to kill GBM6 cell population that did not express any EGFRvIII antigen (n=3, error bars are SEM).

(e) Independent replicate of mouse experiment (GBM6 PDX tumor treatment with different T cell circuits) shown in FIG. 8 *c*.

Figure 14:
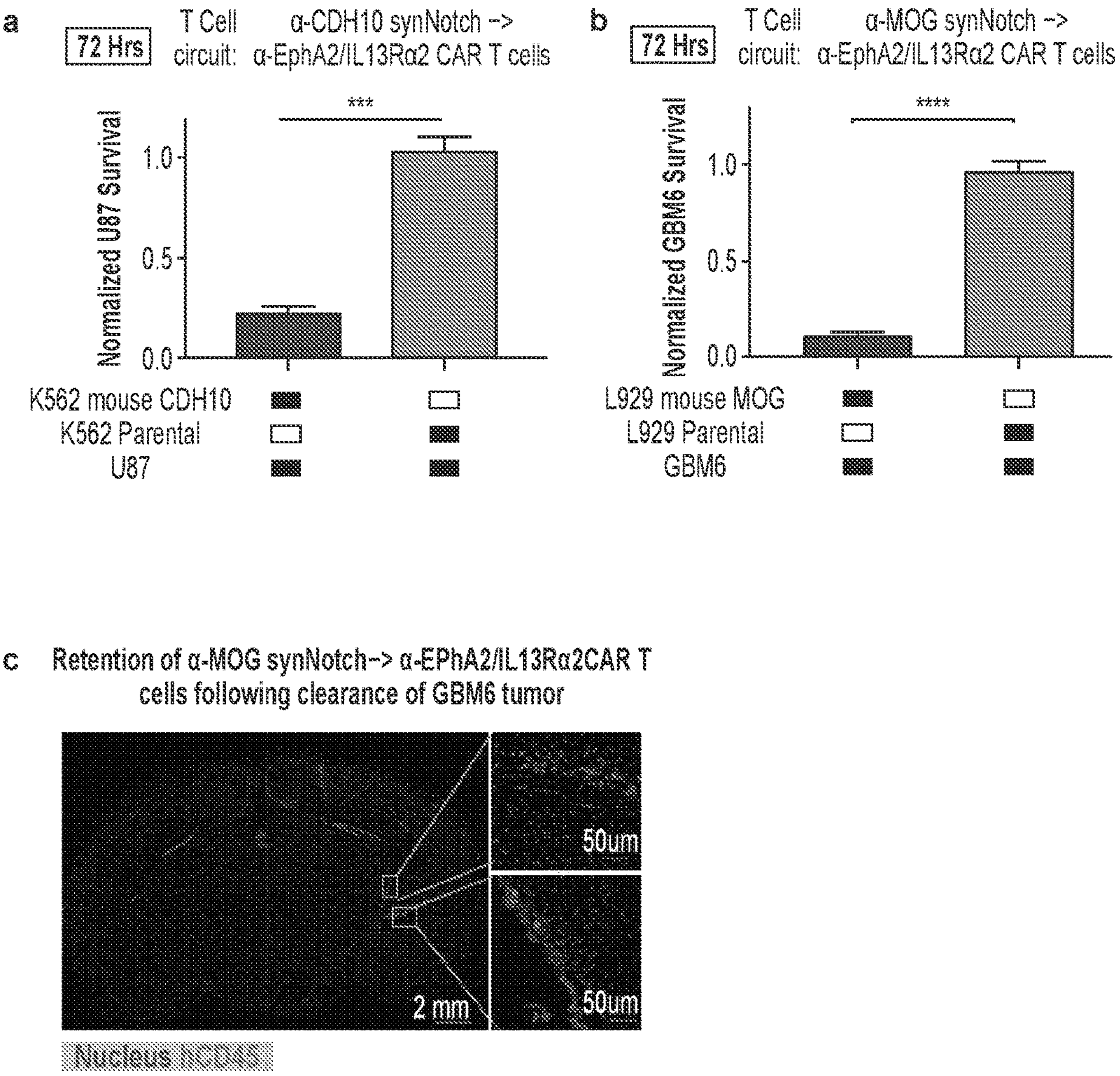

FIG. 14 shows the results of testing $\alpha$-CDH10 synNotch$\rightarrow$$\alpha$-EphA2/IL13R$\alpha$2 CAR and $\alpha$-MOG synNotch$\rightarrow$$\alpha$-EphA2/IL13R$\alpha$2 CAR T cells against GBM6.

(a) Primary CD8+$\alpha$-CDH10 synNotch$\rightarrow$$\alpha$-EphA2/IL13R$\alpha$2 CAR T cells were co-cultured with U87 cells and K562 expressing or not expressing mouse CDH10. Relative cell survival over 72 hours was quantified and showed cytotoxicity capacity of $\alpha$-CDH10 synNotch$\rightarrow$$\alpha$-EphA2/IL13R$\alpha$2 CAR T cells to kill U87 cells only when priming cells are expressing mouse CDH10 (n=3, error bars are SD). Cell population ratio: 1:1:1, 10K cell each.

(b) Primary CD8+$\alpha$-MOG synNotch$\rightarrow$$\alpha$-EphA2/IL13R$\alpha$2 CAR T cells were co-cultured with GBM6 cells and L929 cells expressing or not expressing mouse MOG. Relative cell survival over 72 hours was quantified and showed cytotoxicity capacity of $\alpha$-MOG synNotch$\rightarrow$$\alpha$-EphA2/IL13$\alpha$2 CAR T cells to kill GBM6 cells only when priming cells are expressing mouse MOG (n=3, error bars are SD). Cell population ratio: 1:1:1, 10K cell each.

(c) Representative fluorescent microscopy image reveals clearance of engrafted GBM6 xenograft (lack of mCherry tumor cells) following systemic administration of α-MOG synNotch-CAR T cells. Retention of prime-and-kill CAR T cells (stained for CD45) in the meninges.

DEFINITIONS

As used herein, the terms "treatment," "treating," "treat" and the like, refer to obtaining a desired pharmacologic and/or physiologic effect and/or a response related to the treatment. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

A "therapeutically effective amount" or "efficacious amount" refers to the amount of an agent (including biologic agents, such as cells), or combined amounts of two agents, that, when administered to a mammal or other subject for treating a disease, is sufficient to effect such treatment for the disease. The "therapeutically effective amount" will vary depending on the agent(s), the disease and its severity and the age, weight, etc., of the subject to be treated.

The terms "individual," "subject," "host," and "patient," used interchangeably herein, refer to a mammal, including, but not limited to, murines (e.g., rats, mice), non-human primates, humans, canines, felines, ungulates (e.g., equines, bovines, ovines, porcines, caprines), lagomorphs, etc. In some cases, the individual is a human. In some cases, the individual is a non-human primate. In some cases, the individual is a rodent, e.g., a rat or a mouse. In some cases, the individual is a lagomorph, e.g., a rabbit.

The term "refractory", used herein, refers to a disease or condition that does not respond to treatment. With regard to cancer, "refractory cancer", as used herein, refers to cancer that does not respond to treatment. A refractory cancer may be resistant at the beginning of treatment or it may become resistant during treatment. Refractory cancer may also called resistant cancer.

The term "histology" and "histological" as used herein generally refers to microscopic analysis of the cellular anatomy and/or morphology of cells obtained from a multicellular organism including but not limited to plants and animals.

The term "cytology" and "cytological" as used herein generally refers to a subclass of histology that includes the microscopic analysis of individual cells, dissociated cells, loose cells, clusters of cells, etc. Cells of a cytological sample may be cells in or obtained from one or more bodily fluids or cells obtained from a tissue that have been dissociated into a liquid cellular sample.

The terms "chimeric antigen receptor" and "CAR", used interchangeably herein, refer to artificial multi-module molecules capable of triggering or inhibiting the activation of an immune cell which generally but not exclusively comprise an extracellular domain (e.g., a ligand/antigen binding domain), a transmembrane domain and one or more intracellular signaling domains. The term CAR is not limited specifically to CAR molecules but also includes CAR variants. CAR variants include split CARs wherein the extracellular portion (e.g., the ligand binding portion) and the intracellular portion (e.g., the intracellular signaling portion) of a CAR are present on two separate molecules. CAR variants also include ON-switch CARs which are conditionally activatable CARs, e.g., comprising a split CAR wherein conditional heterodimerization of the two portions of the split CAR is pharmacologically controlled (e.g., as described in PCT publication no. WO 2014/127261 A1 and US Patent Application No. 2015/0368342 A1, the disclosures of which are incorporated herein by reference in their entirety). CAR variants also include bispecific CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. CAR molecules and derivatives thereof (i.e., CAR variants) are described, e.g., in PCT Application No. US2014/016527; Fedorov et al. Sci Transl Med (2013); 5(215):215ra172; Glienke et al. Front Pharmacol (2015) 6:21; Kakarla & Gottschalk 52 Cancer J (2014) 20(2):151-5; Riddell et al. Cancer J (2014) 20(2):141-4; Pegram et al. Cancer J (2014) 20(2):127-33; Cheadle et al. Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety. Useful CARs also include the anti-CD19-4-1BB-CD3ζ CAR expressed by lentivirus loaded CTL019 (Tisagenlecleucel-T) CAR-T cells as commercialized by Novartis (Basel, Switzerland).

The terms "T cell receptor" and "TCR" are used interchangeably and will generally refer to a molecule found on the surface of T cells, or T lymphocytes, that is responsible for recognizing fragments of antigen as peptides bound to major histocompatibility complex (MHC) molecules. The TCR complex is a disulfide-linked membrane-anchored heterodimeric protein normally consisting of the highly variable alpha (α) and beta (β) chains expressed as part of a complex with CD3 chain molecules. Many native TCRs exist in heterodimeric αβ or γδ forms. The complete endogenous TCR complex in heterodimeric αβ form includes eight chains, namely an alpha chain (referred to herein as TCRα or TCR alpha), beta chain (referred to herein as TCRβ or TCR beta), delta chain, gamma chain, two epsilon chains and two zeta chains. In some instance, a TCR is generally referred to by reference to only the TCRα and TCRβ chains, however, as the assembled TCR complex may associate with endogenous delta, gamma, epsilon and/or zeta chains an ordinary skilled artisan will readily understand that reference to a TCR as present in a cell membrane may include reference to the fully or partially assembled TCR complex as appropriate.

Recombinant or engineered individual TCR chains and TCR complexes have been developed. References to the use of a TCR in a therapeutic context may refer to individual recombinant TCR chains. As such, engineered TCRs may include individual modified TCRα or modified TCRβ chains as well as single chain TCRs that include modified and/or unmodified TCRα and TCRβ chains that are joined into a single polypeptide by way of a linking polypeptide.

As used herein, the term "binding-triggered transcriptional switch" or "BTTS" refers to any polypeptide or complex of the same that is capably of transducing a specific binding event on the outside of the cell (e.g. binding of an extracellular domain of the BTTS) to activation of a recombinant promoter within the nucleus of the cell. Many BTTSs work by releasing a transcription factor that activates the promoter. In these embodiments, the BTTS is made up of one or more polypeptides that undergo proteolytic cleavage upon binding to the antigen to release a gene expression regulator that activates the recombinant promoter. For example, a BTTS may comprise (i) an extracellular domain comprising the antigen binding region of a antigen-specific antibody; (ii) a proteolytically cleavable sequence comprising one or more proteolytic cleavage sites; and (iii) an intracellular domain, wherein binding of the antigen binding region to the antigen induces cleavage of the sequence at the one or more proteolytic cleavage sites, thereby releasing the intracellular domain and wherein the intracellular domain activates transcription of an expression cassette. A BTTS can be based on synNotch, A2, MESA, or force receptor, for example, although others are known or could be constructed.

As used herein, by "chimeric bispecific binding member" is meant a chimeric polypeptide having dual specificity to two different binding partners (e.g., two different antigens). Non-limiting examples of chimeric bispecific binding members include bispecific antibodies, bispecific conjugated monoclonal antibodies $(mab)_2$, bispecific antibody fragments (e.g., $F(ab)_2$, bispecific scFv, bispecific diabodies, single chain bispecific diabodies, etc.), bispecific T cell engagers (BiTE), bispecific conjugated single domain antibodies, micabodies and mutants thereof, and the like. Non-limiting examples of chimeric bispecific binding members also include those chimeric bispecific agents described in Kontermann. *MAbs*. (2012) 4(2): 182-197; Stamova et al. *Antibodies* 2012, 1(2), 172-198; Farhadfar et al. *Leuk Res*. (2016) 49:13-21; Benjamin et al. *Ther Adv Hematol*. (2016) 7(3):142-56; Kiefer et al. *Immunol Rev*. (2016) 270(1):178-92; Fan et al. *J Hematol Oncol*. (2015) 8:130; May et al. *Am J Health Syst Pharm*. (2016) 73(1):e6-e13; the disclosures of which are incorporated herein by reference in their entirety.

A "biological sample" encompasses a variety of sample types obtained from an individual or a population of individuals and can be used in various ways, including e.g., the isolation of cells or biological molecules, diagnostic assays, etc. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by mixing or pooling of individual samples, treatment with reagents, solubilization, or enrichment for certain components, such as cells, polynucleotides, polypeptides, etc. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples (e.g., biopsy samples), and cellular samples. Accordingly, biological samples may be cellular samples or acellular samples.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, nanobodies, single-domain antibodies, and fusion proteins comprising an antigen-binding portion of an antibody and a non-antibody protein.

"Antibody fragments" comprise a portion of an intact antibody, for example, the antigen binding or variable region of the intact antibody. Examples of antibody fragments include Fab, Fab', F(ab')2, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Single-chain Fv" or "sFv" antibody fragments comprise the VH and VL domains of antibody, wherein these domains are present in a single polypeptide chain. In some embodiments, the Fv polypeptide further comprises a polypeptide linker between the VH and VL domains, which enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994).

The term "nanobody" (Nb), as used herein, refers to the smallest antigen binding fragment or single variable domain ($V_{HH}$) derived from naturally occurring heavy chain antibody and is known to the person skilled in the art. They are derived from heavy chain only antibodies, seen in camelids (Hamers-Casterman et al. (1993) *Nature* 363:446; Desmyter et al. (2015) *Curr. Opin. Struct. Biol.* 32:1). In the family of "camelids" immunoglobulins devoid of light polypeptide chains are found. "Camelids" comprise old world camelids (*Camelus bactrianus* and *Camelus dromedarius*) and new world camelids (for example, *Llama paccos, Llama glama, Llama guanicoe* and *Llama vicugna*). A single variable domain heavy chain antibody is referred to herein as a nanobody or a $V_{HH}$ antibody.

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

A "orthogonal" or "orthogonalized" member or members of a binding pair are modified from their original or wild-type forms such that the orthogonal pair specifically bind one another but do not specifically or substantially bind the non-modified or wild-type components of the pair. Any binding partner/specific binding pair may be orthogonalized, including but not limited to e.g., those binding partner/specific binding pairs described herein.

The terms "domain" and "motif", used interchangeably herein, refer to both structured domains having one or more particular functions and unstructured segments of a polypeptide that, although unstructured, retain one or more particular functions. For example, a structured domain may encompass but is not limited to a continuous or discontinuous plurality of amino acids, or portions thereof, in a folded polypeptide that comprise a three-dimensional structure which contributes to a particular function of the polypeptide. In other instances, a domain may include an unstructured segment of a polypeptide comprising a plurality of two or more amino acids, or portions thereof, that maintains a particular function of the polypeptide unfolded or disordered. Also encompassed within this definition are domains that may be disordered or unstructured but become structured or ordered upon association with a target or binding partner. Non-limiting examples of intrinsically unstructured domains and domains of intrinsically unstructured proteins are described, e.g., in Dyson & Wright. *Nature Reviews Molecular Cell Biology* 6:197-208.

The terms "synthetic", "chimeric" and "engineered" as used herein generally refer to artificially derived polypeptides or polypeptide encoding nucleic acids that are not naturally occurring. Synthetic polypeptides and/or nucleic acids may be assembled de novo from basic subunits including, e.g., single amino acids, single nucleotides, etc., or may be derived from pre-existing polypeptides or polynucleotides, whether naturally or artificially derived, e.g., as through recombinant methods. Chimeric and engineered polypeptides or polypeptide encoding nucleic acids will generally be constructed by the combination, joining or fusing of two or more different polypeptides or polypeptide encoding nucleic acids or polypeptide domains or polypeptide domain encoding nucleic acids. Chimeric and engineered polypeptides or polypeptide encoding nucleic acids include where two or more polypeptide or nucleic acid "parts" that are joined are derived from different proteins (or nucleic acids that encode different proteins) as well as where the joined parts include different regions of the same protein (or nucleic acid encoding a protein) but the parts are joined in a way that does not occur naturally.

The term "recombinant", as used herein describes a nucleic acid molecule, e.g., a polynucleotide of genomic, cDNA, viral, semisynthetic, and/or synthetic origin, which, by virtue of its origin or manipulation, is not associated with all or a portion of the polynucleotide sequences with which it is associated in nature. The term recombinant as used with respect to a protein or polypeptide means a polypeptide produced by expression from a recombinant polynucleotide. The term recombinant as used with respect to a host cell or a virus means a host cell or virus into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "operably linked" refers to a juxtaposition wherein the components so described are in a relationship permitting them to function in their intended manner. For instance, a promoter is operably linked to a coding sequence if the promoter affects its transcription or expression. Operably linked nucleic acid sequences may but need not necessarily be adjacent. For example, in some instances a coding sequence operably linked to a promoter may be adjacent to the promoter. In some instances, a coding sequence operably linked to a promoter may be separated by one or more intervening sequences, including coding and non-coding sequences. Also, in some instances, more than two sequences may be operably linked including but not limited to e.g., where two or more coding sequences are operably linked to a single promoter.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

A "vector" or "expression vector" is a replicon, such as plasmid, phage, virus, or cosmid, to which another DNA segment, i.e. an "insert", may be attached so as to bring about the replication of the attached segment in a cell.

The term "Heterologous", as used herein, means a nucleotide or polypeptide sequence that is not found in the native (e.g., naturally-occurring) nucleic acid or protein, respectively. Heterologous nucleic acids or polypeptide may be derived from a different species as the organism or cell within which the nucleic acid or polypeptide is present or is expressed. Accordingly, a heterologous nucleic acids or polypeptide is generally of unlike evolutionary origin as compared to the cell or organism in which it resides.

The term "brain-selective extracellular antigen", as used herein, refers to an extracellular antigen (i.e., an antigen that is expressed on the outer surface of cells) that is selectively expressed in brain cells, where the term "selectively expressed" means that the antigen or mRNA encoding the same (as measured by RNA-seq, RT-PCR or arrays) is expressed in brain cells more than any other non-central nervous system tissue tested, where the other tissues can be selected from those shown in FIG. 9 *b*. MOG, CDH10, PTPRZ1 and NRCAM are examples of brain-selective extracellular antigens. Brain-specific extracellular antigens are extracellular antigens that are expressed at least 5-fold higher, at least 10-fold higher, at least 20-fold higher or at least 50-fold higher in brain than the non-central nervous system tissue with the next highest expression, where the tissues can be selected from those shown in FIG. 9 *b*. As shown in FIG. 9 *b*, MOG is a brain-specific antigen, although others could be identified. The expression of brain-selective and brain-specific antigens may be restricted to neurons (including motor neurons, sensory neurons and interneurons) or glial cells (including oligodendrocytes, microglia, and/or astrocytes).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a cell" includes a plurality of such cells and reference to "the cell" includes reference to one or more cells and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

As summarized above, the present disclosure provides a cell comprising a recombinant nucleic acid encoding a transmembrane protein that has an extracellular binding domain that specifically binds to brain-selective extracellular antigen, e.g., MOG, CDH10, PTPRZ1 or NRCAM, wherein the cell does not comprise a nucleic acid encoding an antigen-specific therapeutic that binds to a killing antigen expressed by a glioblastoma. For example, the cell does not comprise a nucleic acid encoding an antigen-specific therapeutic that binds to Ephrin type-A receptor 2 (EphA2), Ephrin type-A receptor 3 (EphA3), Interleukin-13 receptor subunit alpha-1 (IL13RA1), Interleukin-13 receptor subunit alpha-2 (IL13RA2), Epidermal growth factor receptor (EGFR) or erb-b2 receptor tyrosine kinase 2 (ERBB2). In some embodiments, the extracellular binding domain is the variable domain of an antibody (e.g., a nanobody or a single-chain Fv) that specifically binds to the brain-selective extracellular antigen, e.g., MOG, CDH10, PTPRZ1 or NRCAM.

The transmembrane protein can have a variety of structures. In some cases, the transmembrane protein may be composed of an extracellular binding domain, a transmembrane domain and no intracellular signaling domain. In these embodiments, the transmembrane protein may function to tether the cell to a brain cell, thereby preventing the cell from migrating to another tissue.

In other embodiments, the transmembrane protein may be capable of signaling that the extracellular binding domain has bound to its cognate antigen (i.e., MOG, CDH10, PTPRZ1 or NRCAM) to the inside of the cell. In these embodiments, the transmembrane protein may comprise an extracellular binding domain, a transmembrane domain and an intracellular signaling domain. For example, in these embodiments the transmembrane protein may be a chimeric antigen receptor (or a T cell receptor) or a binding-triggered transcriptional switch. In some embodiments, the transmembrane protein may be an inhibitory immune cell receptor (iICR) such as an inhibitory chimeric antigen receptor (iCAR), wherein binding of the iICR to the brain-selective extracellular antigen, MOG, CDH10, PTPRZ1 or NRCAM inhibits activation of the immune cell on which the iICR is expressed. Such iICR proteins are described in e.g., WO2017087723, Fedorov et al. (Sci. Transl. Med. 2013 5: 215ra17) and other references cited above, which are incorporated by reference for that description and examples of the same. In some embodiments such an inhibitory immunoreceptor may comprise an intracellular immunoreceptor tyrosine-based inhibition motif (ITIM), an immunoreceptor tyrosine-based switch motif (ITSM), an NpxY motif, or a YXXΦ motif. Exemplary intracellular domains for such molecules may be found in PD1, CTLA4, BTLA, CD160, KRLG-1, 2B4, Lag-3, Tim-3 and other immune checkpoints, for example. See, e.g., Odorizzi and Wherry (2012) J. Immunol. 188:2957; and Baitsch et al. (2012) PLoSOne 7: e30852.

In some embodiments, the transmembrane protein may be part of a molecular circuit that confines the expression of a target protein, e.g., a therapeutic protein, to the brain. As will be explained below, the therapeutic protein may be antigen-specific in some cases. In these embodiments, the transmembrane protein may be a binding-triggered transcriptional switch, as described in further detail below. In these embodiments, the cell may further comprise a nucleic acid comprising: (i) a coding sequence encoding a therapeutic protein and (ii) a regulatory sequence, wherein the regulatory sequence is operably linked to the coding sequence and is responsive to activation of the binding-triggered transcriptional switch. In some embodiments, the binding-triggered transcriptional switch may a SynNotch polypeptide, e.g., a polypeptide that comprises: (i) an extracellular domain comprising the antigen binding region of a brain-selective extracellular antigen- (e.g., MOG-, CDH10-, PTPRZ1- or NRCAM-) specific antibody; (ii) a proteolytically cleavable Notch receptor polypeptide comprising one or more proteolytic cleavage sites; and (iii) an intracellular domain. In these embodiments, binding of the extracellular domain of (i) to the brain-selective extracellular antigen, e.g., MOG, CDH10, PTPRZ1 or NRCAM on the surface of a brain cell induces cleavage of the synNotch polypeptide at the one or more proteolytic cleavage sites to release the intracellular domain. In these embodiments, the released intracellular domain induces expression of the therapeutic protein of via the regulatory sequence that is operably linked to its coding sequence.

In these embodiments, the therapeutic protein, when expressed, may secreted by the cell or may be on the surface of the cell. In embodiments in which the therapeutic protein is secreted, the therapeutic protein may be, for example, an antibody (e.g., an antibody that binds to PD1, PD-L1, PD-L2, CTLA4, TIM3 or LAG3 or another immune checkpoint, for example), an enzyme (e.g., a superoxide dismutase for removing reactive oxygen species or a protease that can unmask a probody) or a bioactive peptide such as a cytokine (e.g., Il-1ra, IL-4, IL-6, IL-10, IL-11, IL-13, or TGF-β, among many others).

In embodiments in which the therapeutic protein is localized on the surface of the cell, the therapeutic protein may be, for example, signaling protein that comprises an extracellular binding domain (e.g., the variable domain of an antibody), a transmembrane domain, and an intracellular signaling domain, where the protein transmits a signal generated by binding of the binding domain to an antigen on the outside of the cell, to the inside of the cell. For example, the therapeutic protein may be a protein that, when expressed on the surface of an immune cell and it binds to an antigen, activates the immune cell or inhibits activation of the immune cell. For example, the therapeutic protein may be an immune cell receptor (e.g., a chimeric antigen receptor (CAR) or a T cell receptor (TCR)). In these embodiments, binding of the transmembrane protein to the brain-selective extracellular antigen, e.g., MOG, CDH10, PTPRZ1 or NRCAM, via its extracellular binding domain releases the intracellular domain from the transmembrane protein which, in turn, induces expression of the immune cell receptor. In these embodiments, the immune cell receptor does not have an extracellular binding domain that binds to a cancer-specific antigen that expressed by a glioblastoma. Instead, the immune cell receptor may have an extracellular binding domain that binds to a disease-specific antigen on diseased cells that are not glioblastoma cells. Binding of the immune cell to such an antigen should activate the immune cell, thereby killing the diseased cell.

In some embodiments, the therapeutic protein delivered by the activation of the binding-triggered transcriptional switch may prevent therapies from being delivered to the brain. For example, in some embodiments, the therapeutic may be an inhibitory immune cell receptor (iICR) (which may also be referred to as an "inhibitory immunoreceptor") such as an inhibitory chimeric antigen receptor (iCAR). In these embodiments, binding of the transmembrane protein to the brain-selective extracellular antigen (e.g., MOG, CDH10, PTPRZ1 or NRCAM) releases the intracellular domain from the transmembrane protein which, in turn, induces expression of the iICR. In these embodiments, the iICR may have an extracellular binding domain that binds to an antigen that is present on non-diseased cells for example. Binding of the immune cell to such an antigen should inhibit activation of the immune cell, thereby providing a way to prevent cell therapies from being activated in non-diseased areas of the brain. Such iICR proteins are described in e.g., WO2017087723, Fedorov et al. (Sci. Transl. Med. 2013 5: 215ra17) and other references cited above.

In embodiments in which the transmembrane protein is a binding-triggered transcriptional switch that activates expression of a CAR when the binding-triggered transcriptional switch binds to the brain-selective extracellular antigen (MOG, CDH10, PTPRZ1 or NRCAM), the CAR itself may be activated by binding to a killing antigen (i.e., a disease-specific antigen that may be additionally expressed in other, normal, cells that are outside of the brain) associated with one or more non-glioblastoma cancers of the brain. For example, in these embodiments the CAR may be activated by binding of its extracellular binding region to a cancer-specific antigen associated with one or more child brain tumors (e.g., medulloblastoma, diffuse midline glioma (previously called DIPG), ependymoma, craniopharyngiom, embryonal tumor (previously known as PNET), pineoblastoma, brainstem glioma, choroid plexus carcinoma or germ cell tumor, or one or more adult brain tumors, e.g., pituitary adenoma, acoustic neuroma (also known as vestibular schwannoma), meningioma, oligodendroglioma, haemangioblastoma, CNS lymphoma, non-GBM (or low grade) astrocytoma, or a tumor with unknown cells (i.e., an unspecified glioma). Cancer-specific antigens associated with many of such tumors are known or may become known.

In embodiments in which the transmembrane protein is a binding-triggered transcriptional switch that activates expression of a secreted protein when the binding-triggered transcriptional switch binds to the brain-selective extracellular antigen is (e.g., MOG, CDH10, PTPRZ1 or NRCAM), the secreted protein may be specific for the treatment of any of a variety of diseases and conditions that include, but are not limited to, Alzheimer's disease, stroke, brain and spinal cord injury, brain cancer, HIV infection in the brain, ataxia-producing disorders, amyotrophic lateral sclerosis (ALS), Huntington disease, childhood inborn genetic errors affecting the brain, Parkinson's disease, multiple sclerosis, and brain cancer (including non-glioblastoma multiforme and the other brain cancers listed above). Many treatments for such disease and conditions are known or may become known.

In some embodiments, a circuit may comprise at least two BTTSs (e.g., two, three or four BTTSs) and the antigen-specific therapeutic, where the BTTSs can be linked in series (where one BTTS activates another BTTS) or in parallel, where one of the BTTSs binds to the brain selective antigen and at least one of the other BTTSs binds to another antigen, e.g., another brain-specific antigen. Use of more than one BTTS may make the therapy more specific and have less side effects.

The present circuit may integrate the expression of the brain-selective extracellular antigen (e.g., MOG, CDH10, PTPRZ1 or NRCAM) (which may be referred to as the "priming antigen" herein) on a brain cell (which may be diseased or normal) and at least a second antigen expressed on a second, diseased, cell in the brain to produce a desired outcome with respect to the second cell. In some instances, the present circuit may integrate the expression of brain-selective extracellular antigen is in normal brain cells and at least a second antigen expressed on a second, diseased, cell to produce a desired outcome with respect to the second cell. The integration of two antigens expressed by different cells of a heterogeneous cell population to result in a desired targeting event may be referred to herein as "trans-targeting".

In some embodiments, the brain-selective extracellular antigen (e.g., MOG, CDH10, PTPRZ1 or NRCAM) may be expressed on a first brain cell (which may be normal) and the therapeutic protein produced by the cell may have a therapeutic effect on a second cell. In other embodiments, the brain-selective extracellular antigen may be expressed on a diseased brain cell and the therapeutic protein produced by the cell may have a therapeutic effect on the same cell.

For comparison, in this context cis-targeting refers to integrating two antigens to target a single cell which expresses both a priming antigen (e.g., MOG, CDH10, PTPRZ1 or NRCAM) and a targeting antigen (e.g., a disease-specific marker) to produce a desired outcome with respect to the single cell. Thus, in cis-targeting, the targeted cell expresses both the priming antigen and the targeting antigen such that the two antigens are expressed in cis with respect to the cell. In trans-targeting, the targeted cell expresses only the targeting antigen and not the priming antigen such that the two antigens are expressed in trans with respect to the two cells. As such, trans targeting may be employed to target a cell that does not express a priming antigen. In some instances, a circuit of the present disclosure may employ both trans-targeting and cis-targeting, i.e., cis- and trans-targeting may be combined in a single circuit. In some instances, a circuit of the present disclosure may employ only trans-targeting and may e.g., exclude cis-targeting.

In some embodiments, the therapeutic cell may express a binding-triggered transcriptional switch that is responsive to a priming antigen selected from brain-selective extracellular antigens (e.g., MOG, CDH10, PTPRZ1 or NRCAM). The binding-triggered transcriptional switch may be expressed in the plasma membrane of the cell. Binding of the binding-triggered transcriptional switch to the priming antigen may induce expression of a protein in the binding-triggered transcriptional switch expressing cell. In some embodiments, the induced protein may be a heterologous antigen-specific protein, such as a second binding-triggered transcriptional switch or a heterologous antigen-specific therapeutic, examples of which are described above and below. In the context of cis-targeting, binding of the binding-triggered transcriptional switch to the priming antigen induces expression of an antigen specific protein that is specific for a targeting antigen that is also expressed by the priming cell, i.e., the priming cell and the targeted cell are the cell). In the context of trans-targeting, binding of the binding-triggered transcriptional switch to the priming antigen expressed on a cell induces expression of an antigen specific protein that is specific for a targeting antigen that is expressed on a different cell that does not express the priming antigen.

In this manner, trans-targeting allows for targeting of cells by a therapeutic protein, such as an antigen-specific therapeutic, only in the presence of a brain cell that expresses the brain-selective extracellular antigen. Correspondingly, trans-targeting allows for targeting of brain cells with an antigen specific protein, such as an antigen-specific therapeutic, in a heterogeneous cell population, such as a heterogeneous cancer, where the targeted cells do not express the brain-selective extracellular antigen is. Accordingly, such targeted priming antigen (−) cells may be spatially associated with priming-antigen-positive ("priming-antigen (+)"), i.e., cells that that do express priming antigen.

Methods

As summarized above, some embodiments of the present disclosure provide a method of treating diseased cells in the brain. In some embodiments, the diseased cells may be targeted in trans. Such methods may include administering, to a subject in need thereof, a therapeutic cell comprising a recombinant nucleic acid encoding a transmembrane protein that has an extracellular binding domain that specifically binds to a brain-selective extracellular antigen (e.g., MOG, CDH10, PTPRZ1 or NRCAM), wherein the cell does not comprise a nucleic acid encoding an antigen-specific therapeutic that binds to a killing antigen expressed by a glioblastoma. As noted above, the transmembrane protein may have a number of different architectures and, in some embodiments, the transmembrane protein may be a binding-triggered transcriptional switch that drives the expression of a therapeutic protein.

Methods of Treatment

As summarized above, the methods of the present disclosure find use in treating a subject for a disease or disorder of the brain, including, but not limited to medulloblastoma, diffuse midline glioma (previously called DIPG), ependymoma, craniopharyngiom, embryonal tumor (previously known as PNET), pineoblastoma, brainstem glioma, choroid plexus carcinoma or germ cell tumor, or one or more adult brain tumors, e.g., pituitary adenoma, acoustic neuroma (also known as vestibular schwannoma), meningioma, oligodendroglioma, haemangioblastoma, CNS lymphoma, non-GBM (or low grade) astrocytoma, a tumor with unknown cells (i.e., an unspecified glioma), Alzheimer's disease, stroke, brain and spinal cord injury, brain cancer, HIV infection in the brain, ataxia-producing disorders, amyotrophic lateral sclerosis (ALS), Huntington disease, childhood inborn genetic errors affecting the brain, Parkinson's disease, and multiple sclerosis. Such treatments may include obtaining a desired effect with respect to at least one disease cell type (or subpopulation thereof) in the brain.

In some embodiments, the disease may be a cancer from a non-brain or CNS tissue that has metastasized to the brain. Brain metastases can develop from any type of cancer. The most common types of cancer that spread to the brain are breast cancer, lung cancer, kidney cancer, melanoma, colon cancer, and thyroid cancer.

The subject methods may include introducing into a subject in need thereof, a population of the cells described above. The introduced cells may be immune cells, including e.g., myeloid cells or lymphoid cells. In other cases, the introduced cells are not immune cells.

In some instances, the present method may include contacting a cell with one or more nucleic acids, wherein such contacting is sufficient to introduce the nucleic acid(s) into the cell. Any convenient method of introducing nucleic acids into a cell may find use herein including but not limited viral transfection, electroporation, lipofection, bombardment, chemical transformation, use of a transducible carrier (e.g., a transducible carrier protein), and the like. Nucleic acids may be introduced into cells maintained or cultured in vitro or ex vivo. Nucleic acids may also be introduced into a cell in a living subject in vivo, e.g., through the use of one or more vectors (e.g., viral vectors) that deliver the nucleic acids into the cell without the need to isolate, culture or maintain the cells outside of the subject.

Introduced nucleic acids may be maintained within the cell or transiently present. As such, in some instance, an introduced nucleic acid may be maintained within the cell, e.g., integrated into the genome. Any convenient method of nucleic acid integration may find use in the subject methods, including but not limited to e.g., viral-based integration, transposon-based integration, homologous recombination-based integration, and the like. In some instance, an introduced nucleic acid may be transiently present, e.g., extrachromosomally present within the cell. Transiently present nucleic acids may persist, e.g., as part of any convenient transiently transfected vector.

An introduced nucleic acid encoding a circuit may be introduced in such a manner as to be operably linked to a regulatory sequence, such as a promoter, that drives the expression of one or more components of the circuit. The source of such regulatory sequences may vary and may include e.g., where the regulatory sequence is introduced with the nucleic acid, e.g., as part of an expression construct or where the regulatory sequence is present in the cell prior to introducing the nucleic acid or introduced after the nucleic acid. As described in more detail herein, useful regulatory sequence can include e.g., endogenous promoters and heterologous promoters. For example, in some instances, a nucleic acid may be introduced as part of an expression construct containing a heterologous promoter operably linked to a nucleic acid sequence. In some instances, a nucleic acid may be introduced as part of an expression construct containing a copy of a promoter that is endogenous to the cell into which the nucleic acid is introduced. In some instances, a nucleic acid may be introduced without a regulatory sequence and, upon integration into the genome of the cell, the nucleic acid may be operably linked to an endogenous regulatory sequence already present in the cell. Depending on the confirmation and/or the regulatory sequence utilized, expression of each component of the circuit from the nucleic acid may be configured to be constitutive, inducible, tissue-specific, cell-type specific, etc., including combinations thereof.

Any convenient method of delivering the circuit encoding components may find use in the subject methods. In some instances, the subject circuit may be delivered by administering to the subject a cell expressing the circuit. In some instances, the subject circuit may be delivered by administering to the subject a nucleic acid comprising one or more nucleotide sequences encoding the circuit. Administering to a subject a nucleic acid encoding the circuit may include administering to the subject a cell containing the nucleic acid where the nucleic acid may or may not yet be expressed. In some instances, administering to a subject a nucleic acid encoding the circuit may include administering to the subject a vector designed to deliver the nucleic acid to a cell.

Accordingly, in the subject methods of treatment, nucleic acids encoding a circuit or components thereof may be administered in vitro, ex vivo or in vivo. In some instances, cells may be collected from a subject and transfected with nucleic acid and the transfected cells may be administered to the subject, with or without further manipulation including but not limited to e.g., in vitro expansion. In some instances, the nucleic acid, e.g., with or without a delivery vector, may be administered directly to the subject.

Priming cells and targeted cells of a subject circuit will generally differ in at least the expression of priming antigen and targeting antigen. In some instances, priming cells and targeted cells may differ in the expression of at least one surface expressed epitope, e.g., a surfaced expressed protein, an antigen presented in the context of MHC, etc., including e.g., where the surface expressed epitope is a molecule other than the priming antigen and/or the targeting antigen. In some instances, two different targeted cells may differ in the expression of at least one surface expressed epitope, e.g., a surfaced expressed protein, an antigen presented in the context of MHC, etc.

Differential expression between two cells or two cell types may vary. For example, in some instances, a cell expresses one surface epitope not expressed by the other. In some instances, a cell expresses one surface epitope more highly than the surface epitope is expressed by the other cell. Where cells differ in the level, e.g., as compared to the presence/absence, of expression of a surface epitope the difference in level may vary but will generally be substantially different, e.g., sufficiently different to allow for practical targeting of one cell versus the other. Differences in expression between cells may range from less than one order of magnitude of expression to ten orders of magnitude of expression or more, including but not limited to e.g., 1 order of magnitude, 2 orders of magnitude, 3 orders of magnitude, 4 orders of magnitude, 5 orders of magnitude, 6 orders of magnitude, 7 orders of magnitude, 8 orders of magnitude, 9 orders of magnitude, 10 orders of magnitude, etc. In some instances, two cell types differing in level of expression of a particular epitope may be said to be "high" and "low" for the epitope, respectively, where high versus low expression may be differentiated using conventional methods known to the relevant artisan.

In some instances, the method of the present disclosure may be employed to target, treat or clear a subject for minimal residual disease (MRD) remaining after a prior therapy. Targeting, treating and/or clearance of MRD may be pursued using the instant methods whether or not the MRD is or has been determined to be refractory to the prior treatment. In some instances, a method of the present disclosure may be employed to target, treat and/or clear a subject of MRD following a determination that the MRD is refractory to a prior treatment or one or more available treatment options other than those employing the herein described circuits.

In some instances, the instant methods may be employed prophylactically for surveillance. For example, a subject in need thereof may be administered a treatment involving one or more of the herein described circuits when the subject does not have detectable disease but is at risk of developing a disease. In some instances, a prophylactic approach may be employed when a subject is at particularly high risk of developing a disease. In some instances, a prophylactic approach may be employed when a subject has been previously treated for a the disease and is at risk of reoccurrence. Essentially any combination of priming antigen and targeting antigen may be employed in prophylactic treatments, including those described herein.

The methods of treating described herein may, in some instances, be performed in a subject that has previously undergone one or more conventional treatments. For example, in the case of oncology, the methods described herein may, in some instances, be performed following a conventional cancer therapy including but not limited to e.g., conventional chemotherapy, conventional radiation therapy, conventional immunotherapy, surgery, etc. In some instances, the methods described herein may be used when a subject has not responded to or is refractory to a conventional therapy.

With respect to the disease as a whole, desired effects of the described treatments may result in a reduction in the number of diseased cells, a reduction in the size of the diseased cells, a reduction in one or more symptoms, etc.

Immune cell activation, as a result of some embodiments of the methods described herein, may be measured in a variety of ways, including but not limited to e.g., measuring the expression level of one or more markers of immune cell activation. Useful markers of immune cell activation include but are not limited to e.g., CD25, CD38, CD40L (CD154), CD69, CD71, CD95, HLA-DR, CD137 and the like. For example, in some instances, upon antigen binding by an immune cell receptor an immune cell may become activated and may express a marker of immune cell activation (e.g., CD69) at an elevated level (e.g., a level higher than a corresponding cell not bound to antigen). Levels of elevated expression of activated immune cells of the present disclosure will vary and may include an increase, such as a 1-fold or greater increase in marker expression as compared to un-activated control, including but not limited to e.g., a 1-fold increase, a 2-fold increase, a 3-fold increase, a 4-fold increase, etc.

In some instances, an immune cell modified to encode a circuit of the present disclosure, when bound to a targeted antigen, may have increased cytotoxic activity, e.g., as compared to an un-activated control cell. In some instances, activated immune cells encoding a subject circuit may show 10% or greater cell killing of antigen expressing target cells as compared to un-activated control cells. In some instances, the level of elevated cell killing of activated immune cells will vary and may range from 10% or greater, including but not limited to e.g., 20% or greater, 30% or greater, 40% or greater, 50% or greater, 60% or greater, 70% or greater, 80% or greater, 90% or greater, etc., as compared to an appropriate control.

In some instances, treatment may involve modulation, including induction, of the expression and/or secretion of a cytokine by an immune cell containing nucleic acid sequences encoding a circuit as described herein. Non-limiting examples of cytokines, the expression/secretion of which may be modulated, include but are not limited to e.g., Interleukins and related (e.g., IL-1-like, IL-1α, IL-1β, IL-1RA, IL-18, IL-2, IL-4, IL-7, IL-9, IL-13, IL-15, IL-3, IL-5, GM-CSF, IL-6-like, IL-6, IL-11, G-CSF, IL-12, LIF, OSM, IL-10-like, IL-10, IL-20, IL-14, IL-16, IL-17, etc.), Interferons (e.g., IFN-α, IFN-β, IFN-γ, etc.), TNF family (e.g., CD154, LT-β, TNF-α, TNF-β, 4-1BBL, APRIL, CD70, CD153, CD178, GITRL, LIGHT, OX40L, TALL-1, TRAIL, TWEAK, TRANCE, etc.), TGF-β family (e.g., TGF-β1, TGF-β2, TGF-β3, etc.) and the like.

In some instances, activation of an immune cell through a circuit of the present disclosure may induce an increase in cytokine expression and/or secretion relative to that of a comparable cell where the circuit is not present or otherwise inactive. The amount of the increase may vary and may range from a 10% or greater increase, including but not limited to e.g., 10% or greater, 25% or greater, 50% or greater, 75% or greater, 100% or greater, 150% or greater, 200% or greater, 250% or greater, 300% or greater, 350% or greater 400% or greater, etc.

Conventional Treatments and Combination Therapy

As will be readily understood, the methods of treating described herein may, in some instances, be combined with one or more conventional treatments. For example, the method described herein may, in some instances, be combined with a conventional therapy including but not limited to e.g., a treatment with a drug, conventional chemotherapy, conventional radiation therapy, conventional immunotherapy, surgery, etc.

In some instances, the methods described herein may be used before or after a conventional therapy. For example, the methods described herein may be used as an adjuvant therapy, e.g., after a subject has seen improvement from a conventional therapy, or may be used when a subject has not responded to a conventional therapy. In some instances, the methods described herein may be used prior to an additional therapy, e.g., to prepare a subject for an additional therapy, e.g., a conventional therapy as described herein.

Antigen-Specific Therapeutics

As summarized above, in some embodiments the present method a binding triggered transcriptional switch (BTTS) responsive to a priming antigen may induce the expression of an antigen-specific therapeutic responsive to one or more targeting antigens. Useful antigen-specific therapeutics will vary and may include surfaced expressed and secreted antigen-specific therapeutics. For example, in some instances, an antigen-specific therapeutic used in the methods of the present disclosure may be expressed, in response to the activation of a BTTS, on the surface of an immune cell, i.e., the immune cell genetically modified to encode a priming/targeting circuit as described herein. In some instances, an antigen-specific therapeutic used in the methods of the present disclosure may be secreted, in response to the activation of a BTTS, from an immune cell, i.e., the immune cell genetically modified to encode a priming/targeting circuit as described herein.

In general, except where described otherwise, the antigen-specific therapeutic of a herein described circuit will not be expressed in the absence of the activation of the BTTS that induces its expression. Also, except where described otherwise, an antigen-specific therapeutic of a herein described circuit will not be active in the absence of the antigen to which it binds, i.e., without binding the antigen to which the antigen-specific therapeutic is specific. Binding of its respective antigen, or antigens in the case of multi- or bispecific agents, results in activation of the antigen-specific therapeutic. When expressed by, or otherwise engaged with, an immune cell and bound to antigen(s) the antigen-specific therapeutic may activate the immune cell. Activated immune cells may mediate one or more beneficial effects with respect to a diseased cell in the brain of a subject, including those described herein such as but not limited to e.g., cancer cell killing, cytokine release, and the like.

The term "antigen", with respect to the herein described antigen-specific binding domains, is used in a broad sense to refer to essentially any specific binding partner to which the antigen-specific therapeutic binds. As such, any convenient specific binding pair, i.e., specific binding member and specific binding partner pair, may find use in the antigen-specific therapeutics of the instant methods including but not limited to e.g., antigen-antibody pairs, ligand receptor pairs, scaffold protein pairs, etc. In some instances, the specific binding member may be an antibody and its binding partner may be an antigen to which the antibody specifically binds. In some instances, the specific binding member may be a receptor and its binding partner may be a ligand to which the receptor specifically binds. In some instances, the specific binding member may be a ligand and its binding partner may be a receptor to which the ligand specifically binds.

In some instances, useful ligand-receptor specific binding pairs may include where the specific binding member is a mutein of a ligand having at least one mutation relative to the wild-type ligand, including but not limited to e.g., one or more mutations, two or more mutations, three or more mutations, four or more mutations, five or more mutations, etc. In some instances, useful muteins will have at least 90% sequence identity with the relevant wild-type amino acid sequence, including but not limited to e.g., at least 95%, at least 96%, at least 97%, at least 98%, at least 99%, etc., sequence identity with the relevant wild-type amino acid sequence. In some instances, a mutein employed in the subject polypeptide may have higher affinity for the receptor as compared to the affinity between the receptor and the wild-type ligand.

Antigen-specific therapeutics useful in the methods of the present disclosure will vary and may include but are not limited to e.g., chimeric antigen receptors (CARs), T cell receptors (TCRs), chimeric bispecific binding members, and the like.

Useful CARs include essentially any CAR useful in the treatment of cancer, including single-chain and multi-chain CARs, directed to one or more targeting antigens. A CAR used in the instant methods will generally include, at a minimum, an antigen binding domain, a transmembrane domain and an intracellular signaling domain. An employed CAR may further include one or more costimulatory domains.

Non-limiting examples of CARs that may be employed include those used in commercialized CAR T cell (CART) therapies that are directed to one or more appropriate targeting antigens or have been modified to be directed to one or more appropriate targeting antigens. In general a CAR employed herein does not target glioblastoma antigens including but not limited to e.g., EphA2, EphA3, IL13R (e.g., IL13RA1 or IL13RA2), EGFR, and ERBB2.

Useful CARs, e.g., that may be modified to be directed to an appropriate targeting antigen, or useful domains thereof, e.g., that may be employed in a CAR directed to an appropriate targeting antigens, in some instances may include those described in U.S. Pat. Nos. 9,914,909; 9,821,012; 9,815,901; 9,777,061; 9,662,405; 9,657,105; 9,629,877; 9,624,276; 9,598,489; 9,587,020; 9,574,014; 9,573,988; 9,499,629; 9,446,105; 9,394,368; 9,328,156; 9,233,125; 9,175,308 and 8,822,647; the disclosures of which are incorporated herein by reference in their entirety. In some instances, useful CARs may include or exclude heterodimeric, also referred to as dimerizable or switchable, CARs and/or include or exclude one or more of the domains thereof. Useful heterodimeric CARs and/or useful domains thereof may, in some instances, include those described in U.S. Pat. Nos. 9,587,020 and 9,821,012 as well as U.S. Pub. Nos. US20170081411A1, US20160311901A1, US20160311907A1, US20150266973A1 and PCT Pub. Nos. WO2014127261A1, WO2015142661A1, WO2015090229A1 and WO2015017214A1; the disclosures of which are incorporated herein by reference in their entirety.

As summarized above, in some instances, the antigen binding domain of a CAR, such but not limited to e.g., those described in any one of the documents referenced above, may be substituted or amended with an alternative or additional antigen binding domain directed to a different antigen, such as but not limited to one or more of the antigens described herein, for use in the herein described methods. In such instances, the intracellular portions (i.e., the intracellular signaling domain or the one or more costimulatory domains) of the antigen-domain-substituted CAR may or may not be modified.

Useful CARs and/or useful domains thereof may, in some instances, include those that have been or are currently being investigated in one or more clinical trials, including but not limited to the CARs directed to the following antigens (listed with an exemplary corresponding clinical trial number, further information pertaining to which may be retrieved by visiting www(dot)clinicaltrials(dot)gov): AFP, e.g., in NCT03349255; BCMA, e.g., in NCT03288493; CD10, e.g., in NCT03291444; CD117, e.g., in NCT03291444; CD123, e.g., in NCT03114670; CD133, e.g., in NCT02541370; CD138, e.g., in NCT01886976; CD171, e.g., in NCT02311621; CD19, e.g., in NCT02813252; CD20, e.g., in NCT03277729; CD22, e.g., in NCT03244306; CD30, e.g., in NCT02917083; CD33, e.g., in NCT03126864; CD34, e.g., in NCT03291444; CD38, e.g., in NCT03291444; CD5, e.g., in NCT03081910; CD56, e.g., in NCT03291444; CD7, e.g., in NCT02742727; CD70, e.g., in NCT02830724; CD80, e.g., in NCT03356808; CD86, e.g., in NCT03356808; CEA, e.g., in NCT02850536; CLD18, e.g., in NCT03159819; CLL-1, e.g., in NCT03312205; cMet, e.g., in NCT01837602; EGFR, e.g., in NCT03182816; EGFRvIII, e.g., in NCT02664363; EpCAM, e.g., in NCT03013712; EphA2, e.g., in NCT02575261; GD-2, e.g., in NCT01822652; Glypican 3, e.g., in NCT02905188; GPC3, e.g., in NCT02723942; HER-2, e.g., in NCT02547961; kappa immunoglobulin, e.g., in NCT00881920; LeY, e.g., in NCT02958384; LMP1, e.g., in NCT02980315; mesothelin, e.g., in NCT02930993; MG7, e.g., in NCT02862704; MUC1, e.g., in NCT02587689; NKG2D-ligands, e.g., in NCT02203825; PD-L1, e.g., in NCT03330834; PSCA, e.g., in NCT02744287; PSMA, e.g., in NCT03356795; ROR1, e.g., in NCT02706392; ROR1R, e.g., in NCT02194374; TACI, e.g., in NCT03287804; and VEGFR2, e.g., in NCT01218867.

Useful TCRs include essentially any TCR useful in the treatment of cancer, including single-chain and multi-chain TCRs, directed to a targeting antigen. A TCR used in the instant methods will generally include, at a minimum, an antigen binding domain and a modified or unmodified TCR chain, or portion thereof, including but not limited to e.g., a modified or unmodified α-chain, a modified or unmodified β-chain, etc. An employed TCR may further include one or more costimulatory domains. In some instances, a TCR employed herein will include an alpha chain and a beta chain and recognize antigen when presented by a major histocompatibility complex.

Essentially any TCR can be induced by a BTTS using a method of the present disclosure including e.g., TCRs that are specific for any of a variety of epitopes, including, e.g., an epitope expressed on the surface of a cancer cell, a peptide-MHC complex on the surface of cancer cell, and the like. In some cases, the TCR is an engineered TCR.

Non-limiting examples of engineered TCRs, including those having immune cell activation function and that may be modified to include an antigen-binding domain specific for a suitable targeting antigen, useful in the methods described herein include, e.g., antigen-specific TCRs, Monoclonal TCRs (MTCRs), Single chain MTCRs, High Affinity CDR2 Mutant TCRs, CD1-binding MTCRs, High Affinity NY-ESO TCRs, VYG HLA-A24 Telomerase TCRs, including e.g., those described in PCT Pub Nos. WO 2003/020763, WO 2004/033685, WO 2004/044004, WO 2005/114215, WO 2006/000830, WO 2008/038002, WO 2008/039818, WO 2004/074322, WO 2005/113595, WO 2006/125962; Strommes et al. Immunol Rev. 2014; 257(1):145-64; Schmitt et al. Blood. 2013; 122(3):348-56; Chapuls et al. Sci Transl Med. 2013; 5(174):174ra27; Thaxton et al. Hum Vaccin Immunother. 2014; 10(11):3313-21 (PMID:25483644); Gschweng et al. Immunol Rev. 2014; 257(1):237-49 (PMID:24329801); Hinrichs et al. Immunol Rev. 2014; 257(1):56-71 (PMID:24329789); Zoete et al. Front Immunol. 2013; 4:268 (PMID:24062738); Man et al. Clin Exp Immunol. 2012; 167(2):216-25 (PMID:22235997); Zhang et al. Adv Drug Deliv Rev. 2012; 64(8):756-62 (PMID:22178904); Chhabra et al. Scientific World Journal. 2011; 11:121-9 (PMID:21218269); Boulter et al. Clin Exp Immunol. 2005; 142(3):454-60 (PMID:16297157); Sami et al. Protein Eng Des Sel. 2007; 20(8):397-403; Boulter et al. Protein Eng. 2003; 16(9):707-11; Ashfield et al. IDrugs.

2006; 9(8):554-9; Li et al. Nat Biotechnol. 2005; 23(3):349-54; Dunn et al. Protein Sci. 2006; 15(4):710-21; Liddy et al. Mol Biotechnol. 2010; 45(2); Liddy et al. Nat Med. 2012; 18(6):980-7; Oates, et al. Oncoimmunology. 2013; 2(2): e22891; McCormack, et al. Cancer Immunol Immunother. 2013 April; 62(4):773-85; Bossi et al. Cancer Immunol Immunother. 2014; 63(5):437-48 and Oates, et al. Mol Immunol. 2015 October; 67(2 Pt A):67-74; the disclosures of which are incorporated herein by reference in their entirety.

Useful TCRs include those having wild-type affinity for their respective antigen as well as those having enhanced affinity for their respective antigen. TCRs having enhanced affinity for their respective antigen may be referred to as "affinity enhanced" or "enhanced affinity" TCRs. The affinity of a TCR may be enhanced by any convenient means, including but not limited to binding-site engineering (i.e., rational design), screening (e.g., TCR display), or the like. Non-limiting examples of affinity enhanced TCRs and methods of generating enhanced affinity TCRs include but are not limited to e.g., those described in PCT Pub. Nos. 20150118208, 2013256159, 20160083449; 20140349855, 20100113300, 20140371085, 20060127377, 20080292549, 20160280756, 20140065111, 20130058908, 20110038842, 20110014169, 2003276403 and the like; the disclosures of which are incorporated herein by reference in their entirety. Further engineered TCRs, modified to be directed to an appropriate targeting antigen, that may be expressed in response to release of an intracellular domain of a BTTS of the present disclosure include e.g., those described in PCT Application No. US2017/048040; the disclosure of which is incorporated herein by reference in its entirety.

Useful TCRs, which may be modified to be directed to an appropriate targeting antigen, may, in some instances, also include those described in U.S. Pat. Nos. 9,889,161; 9,889,160; 9,868,765; 9,862,755; 9,717,758; 9,676,867; 9,409,969; 9,115,372; 8,951,510; 8,906,383; 8,889,141; 8,722,048; 8,697,854; 8,603,810; 8,383,401; 8,361,794; 8,283,446; 8,143,376; 8,003,770; 7,998,926; 7,666,604; 7,456,263; 7,446,191; 7,446,179; 7,329,731; 7,265,209; and 6,770,749; the disclosures of which are incorporated herein by reference in their entirety.

As described above, in some instances, the antigen binding domain of a TCR, such as but not limited to e.g., those described or referenced above, may be substituted or amended with an alternative or additional antigen binding domain directed to a different antigen, such as but not limited to one or more of the antigens described herein, for use in the herein described methods. In such instances, the other portions (i.e., the transmembrane domain, any intracellular signaling domains, etc.) of the antigen-domain-substituted TCR may or may not be modified.

As summarized above, in some instances, useful antigen-specific therapeutics may include those that, upon induction by an activated BTTS, are expressed and secreted from the producing cell, including e.g., where the secreting cell is an immune cell. For example, upon binding of a BTTS expressed by an immune cell, the BTTS may induce expression and secretion of an encoded antigen-specific therapeutic specific for a targeting antigen. The secreted antigen-specific therapeutic may target a target antigen expressing cancer cell in trans, thereby mediating killing of the target cell. As described herein, in some instances, a secreted antigen-specific therapeutic may increase the zone of targeting or the zone of killing of a subject circuit as compared to a similar circuit encoding a non-secreted (e.g., membrane expressed) antigen-specific therapeutic.

Useful secreted antigen-specific therapeutics will vary and in some instances may include but are not limited to e.g., chimeric bispecific binding members. In some instances, useful chimeric bispecific binding members may include those that target a protein expressed on the surface of an immune cell, including but not limited to e.g., a component of the T cell receptor (TCR), e.g., one or more T cell co-receptors. Chimeric bispecific binding members that bind to a component of the TCR may be referred to herein as a TCR-targeted bispecific binding agent. Chimeric bispecific binding members useful in the instant methods will generally be specific for a targeting antigen and may, in some instances, be specific for a targeting antigen and a protein expressed on the surface of an immune cell (e.g., a component of a TCR such as e.g., a CD3 co-receptor).

In some instances, useful chimeric bispecific binding members may include a bispecific T cell engager (BiTE). A BiTE is generally made by fusing a specific binding member (e.g., a scFv) that binds an immune cell antigen to a specific binding member (e.g., a scFv) that binds a cancer antigen (e.g., a tumor associated antigen, a tumor specific antigen, etc.). For example, an exemplary BiTE includes an anti-CD3 scFv fused to an anti-tumor associated antigen (e.g., EpCAM, CD19, etc.) scFv via a short peptide linker (e.g., a five amino acid linker, e.g., GGGGS).

As summarized above, in some instances, the antigen binding domain of a chimeric bispecific binding member, such as but not limited to e.g., those described or referenced above, may be substituted or amended with an alternative or additional antigen binding domain directed to a different antigen, such as but not limited to one or more of the antigens described herein, for use in the herein described methods. In such instances, the other portions (i.e., linker domain, any immune cell targeting domains, etc.) of the antigen-domain-substituted chimeric bispecific binding member may or may not be modified.

In some instances, a payload induced by binding of a BTTS to its respective priming antigen in a herein described method may include a secreted bio-orthogonal adapter molecule. Such bio-orthogonal adapter molecules may, in some instances, be configured to target and bind a targeting antigen and also bind or be bound by a heterologous polypeptide expressed by an immune cell.

For example, in some instances, a subject circuit employed in the herein described methods may encode, within an immune cell: a BTTS responsive to a priming antigen; a bio-orthogonal adapter molecule specific for a targeting antigen; and a therapeutic, or portion thereof, which binds the bio-orthogonal adapter molecule. In such a circuit, expression and secretion of the bio-orthogonal adapter molecule is induced upon binding of the BTTS to the priming antigen. Then, in the presence of both (1) a cancer cell expressing the targeting antigen and (2) the therapeutic that binds the bio-orthogonal adapter molecule, the therapeutic binds the bio-orthogonal adapter molecule which then binds the targeting antigen, thereby activating the therapeutic. The activated therapeutic may then mediate a therapeutic effect (e.g., a cytotoxic effect) on the diseased cell expressing the targeting antigen, including where the targeting antigen is expressed in trans with respect to the priming antigen. As described herein, in some instances, a secreted bio-orthogonal adapter molecule may increase the zone of targeting or the zone of killing of a subject circuit as compared to a similar circuit encoding a non-secreted (e.g., membrane expressed) antigen-specific therapeutic.

Bio-orthogonal adapter molecules may be employed in various contexts within the herein described methods. For example, in some instances, a bio-orthogonal adapter molecule may be employed that includes a diffusible antigen binding portion of an antigen-specific therapeutic, such as e.g., a diffusible antigen binding portion of a CAR, a diffusible antigen binding portion of a TCR, or the like. In some instances, such diffusible antigen binding portion of antigen-specific therapeutics may be referred to a "diffusible head", including e.g., a "diffusible CAR head", a "diffusible TCR head", and the like.

In some instances, the therapeutic may bind directly to the bio-orthogonal adapter molecule. Strategies for direct binding of the therapeutic to the bio-orthogonal adapter molecule may vary. For example, in some instances, the therapeutic may include a binding domain (e.g., such as an orthogonal antibody or fragment thereof) that binds a binding moiety (e.g., an orthogonal epitope to which an antibody may be directed) covalently attached to the bio-orthogonal adapter. As a non-limiting example, a therapeutic may include a binding domain to a non-naturally occurring epitope, e.g., an anti-fluorescein antibody or a fragment thereof, and the bio-orthogonal adapter molecule may include the epitope, e.g., a fluorescein, covalently attached thereto. In some instances, the configuration of the bio-orthogonal adapter molecule and therapeutic interaction may be reversed as compared to that previously described, including e.g., where the therapeutic includes a covalently attached epitope and the bio-orthogonal adapter molecule includes a binding domain to the epitope. Useful epitopes will vary and may include but are not limited to e.g., small molecule-based epitopes, peptide-based epitopes (e.g., peptide neo-epitopes), oligonucleotide-based epitopes, and the like. The epitope-binding domains will vary correspondingly and may include but are not limited to e.g., small molecule binding domains, peptide binding domains, oligonucleotide binding domains, and the like.

Non-limiting examples of useful bio-orthogonal adapter molecules, and the domains that bind thereto, include but are not limited to e.g., the peptide neo-epitopes and the antibody binding domains that bind thereto as used in switchable CAR (sCAR) T cells, including but not limited to e.g., those described in Rodgers et al. Proc Natl Acad Sci USA. (2016) 113(4):E459-68 and Cao et al., Angew Chem Int Ed Engl. 2016 Jun. 20; 55(26):7520-4 as well as PCT Pub. No. WO2016168773; the disclosures of which are incorporated herein by reference in their entirety.

In some instances, the therapeutic may bind indirectly to the bio-orthogonal adapter molecule, including e.g., where binding is mediated by a diffusible dimerizing agent. Non-limiting examples of suitable dimerizing agents, and the dimerizing domains that bind thereto, include protein dimerizers.

Protein dimerizers generally include polypeptide pairs that dimerize, e.g., in the presence of or when exposed to a dimerizing agent. The dimerizing polypeptide pairs of a protein dimerizer may homo-dimerize or hetero-dimerize (i.e., the dimerizing polypeptide pairs may include two of the same polypeptide that form a homodimer or two different polypeptides that form a heterodimer). Non-limiting pairs of protein dimerizers (with the relevant dimerizing agent in parentheses) include but are not limited to e.g., FK506 binding protein (FKBP) and FKBP (rapamycin); FKBP and calcineurin catalytic subunit A (CnA) (rapamycin); FKBP and cyclophilin (rapamycin); FKBP and FKBP-rapamycin associated protein (FRB) (rapamycin); gyrase B (GyrB) and GyrB (coumermycin); dihydrofolate reductase (DHFR) and DHFR (methotrexate); DmrB and DmrB (AP20187); PYL and ABI (abscisic acid); Cry2 and CIB1 (blue light); GAI and GID1 (gibberellin); and the like. Further description, including the amino acid sequences, of such protein dimerizers is provided in U.S. Patent Application Publication No. US 2015-0368342 A1; the disclosure of which is incorporated herein by reference in its entirety.

Useful protein dimerizers also include those nuclear hormone receptor derived protein dimerizers that dimerize in the presence of a dimerizing agent described in PCT Pub. No. WO 2017/120546 and U.S. Patent Pub. No. US 2017/0306303 A1; the disclosures of which are incorporated by reference herein in their entirety, and the like. Such nuclear hormone receptor derived dimerizers will generally include a first member of the dimerization pair that is a co-regulator of a nuclear hormone receptor and a second member of the dimerization pair comprises an LBD of the nuclear hormone receptor.

Where a bio-orthogonal adapter molecule is employed in a subject circuit, the expression of the therapeutic, which binds the bio-orthogonal adapter molecule to mediate targeting antigen recognition, may or may not be controlled by the circuit. Put another way, the expression of the therapeutic may or may not be tied to the activation of the BTTS (e.g., the binding of the BTTS to priming antigen or another antigen) of the circuit. In some instances, the circuit may be configured such that binding of a BTTS to its antigen induces expression of a therapeutic which binds a bio-orthogonal adapter molecule. In some instances, the BTTS that induces expression of the therapeutic is the same BTTS that induces expression of the bio-orthogonal adapter molecule. In some instance, the therapeutic is induced by a BTTS that is different (i.e., separate) from the BTTS that induces expression of the bio-orthogonal adapter molecule.

In some instances, expression of a therapeutic which binds a bio-orthogonal adapter molecule may not be induced by a BTTS. For example, in some instances, rather than being induced by a BTTS, such a therapeutic is expressed under the control of a separate regulatory element or sequence, including but not limited to e.g., where the expression of the therapeutic is constitutive, inducible, conditional, tissue specific, cell type specific, or the like. In some instances, for example, independent expression (e.g., constitutive expression, inducible expression, etc.) of the therapeutic by introduced immune cells allows for a diffusible bio-orthogonal adapter molecule to mediate the activation of the therapeutic in immune cells that are distant from the site of priming.

In some instances, expression of a bio-orthogonal adapter molecule, bound by a therapeutic, may not be induced by a BTTS, including where the corresponding therapeutic is induced by a BTTS. For example, in some instances, rather than being induced by a BTTS, such a bio-orthogonal adapter molecule is expressed under the control of a separate regulatory element or sequence, including but not limited to e.g., where the expression of the bio-orthogonal adapter molecule is constitutive, inducible, conditional, tissue specific, cell type specific, or the like. In some instances, the bio-orthogonal adapter molecule may be externally provided.

In some instances, an antigen-specific therapeutic may have an extracellular domain that includes a first member of a specific binding pair that binds a second member of the specific binding pair, wherein the extracellular domain does not include any additional first or second member of a second specific binding pair. For example, in some instances, an antigen-specific therapeutic may have an extracellular domain that includes a first antigen-binding domain that binds an antigen, wherein the extracellular domain does not include any additional antigen-binding domains and does not bind any other antigens. A subject antigen-specific therapeutic may, in some instances, include only a single extracellular domain. Accordingly, an employed antigen-specific therapeutic may be specific for a single antigen and only specific for the single antigen. Such, antigen-specific therapeutics may be referred to as a "single antigen antigen-specific therapeutic".

In some instances, an antigen-specific therapeutic may have an extracellular domain that includes the first or second members of two or more specific binding pairs. For example, in some instances, an antigen-specific therapeutic may have an extracellular domain that includes a first antigen-binding domain and a second antigen-binding domain that are different such that the extracellular domain is specific for two different antigens. In some instances, an antigen-specific therapeutic may have two or more extra-cellular domains that each includes the first or second members of two different specific binding pairs. For example, in some instances, an antigen-specific therapeutic may have a first extracellular domain that includes a first antigen-binding domain and a second extracellular domain that includes a second antigen-binding domain where the two different antigen binding domains are each specific for a different antigen. As such, the antigen-specific therapeutic may be specific for two different antigens.

An antigen-specific therapeutic specific for two or more different antigens, containing either two extracellular domains or one extracellular domain specific for two different antigens, may be configured such that the binding of either antigen to the antigen-specific therapeutic is sufficient to active the antigen-specific therapeutic. Such an antigen-specific therapeutic, capable of being activated by any of two or more antigens, may find use in the described circuits as a component of a logic gate containing OR functionality. In some instances, an antigen-specific therapeutic specific for two different antigens may be referred to as a "two-headed antigen-specific therapeutic". Antigen-specific therapeutics specific for multiple antigens will not be limited to only two antigens and may, e.g., be specific for and/or activated by more than two antigens, including e.g., three or more, four or more, five or more, etc.

An example of an antigen-specific therapeutic specific for two or more different antigens is a tandem CAR (also referred to as "tan CAR" or "tanCAR"). A "tandem CAR" is a bispecific CAR that includes two or more non-identical antigen recognition domains. Non-limiting examples of tandem CARs include those described in U.S. Pat. Nos. 9,447,194; 10,155,038; 10,189,903; and 10,239,948; U.S. Patent Application Pub. No. 20130280220 and PCT Application Pub. No. WO/2013/123061; the disclosures of which are incorporated herein by reference in their entirety. Tandem CARs may be configured to bind a variety of different antigens, including but not limited to e.g., two or more or the antigens described herein and/or two or more of the antigens described in U.S. Pat. Nos. 9,447,194; 10,155,038; 10,189,903; and 10,239,948; U.S. Patent Application Pub. No. 20130280220 and PCT Application Pub. No. WO/2013/123061.

Binding Triggered Transcriptional Switches (BTTS)

The method of the present disclosure may include the use of circuits employing a BTTS to induce expression of an encoded antigen-specific therapeutic. As used herein, a "binding-triggered transcriptional switch" or BTTS generally refers to a synthetic modular polypeptide or system of interacting polypeptides having an extracellular domain that includes a first member of a specific binding pair, a binding-transducer and an intracellular domain. Upon binding of the second member of the specific binding pair to the BTTS the binding signal is transduced to the intracellular domain such that the intracellular domain becomes activated and performs some function within the cell that it does not perform in the absence of the binding signal. Binding triggered transcriptional switches are described in e.g., PCT Pub. No. WO 2016/138034 as well as U.S. Pat. Nos. 9,670,281 and 9,834,608; the disclosures of which are incorporated herein by reference in their entirety.

The specific binding member of the extracellular domain generally determines the specificity of the BTTS. In some instances, a BTTS may be referred according to its specificity as determined based on its specific binding member. For example, a specific binding member having binding partner "X" may be referred to as an X-BTTS or an anti-X BTTS.

Any convenient specific binding pair, i.e., specific binding member and specific binding partner pair, may find use in the BTTS of the instant methods including but not limited to e.g., antigen-antibody pairs, ligand receptor pairs, scaffold protein pairs, etc. In some instances, the specific binding member may be an antibody and its binding partner may be an antigen to which the antibody specifically binds. In some instances, the specific binding member may be a receptor and its binding partner may be a ligand to which the receptor specifically binds. In some instances, the specific binding member may be a scaffold protein and its binding partner may be a protein to which the scaffold protein specifically binds. Useful specific binding pairs include those specific for priming antigen and/or one or more targeting/killing antigens, including those described herein.

In some cases, the specific binding member is an antibody. The antibody can be any antigen-binding antibody-based polypeptide, a wide variety of which are known in the art. In some instances, the specific binding member is or includes a monoclonal antibody, a single chain Fv (scFv), a Fab, etc. Other antibody based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use. In some instances, T-cell receptor (TCR) based recognition domains such as single chain TCR (scTv, single chain two-domain TCR containing VαVβ) are also suitable for use.

Where the specific binding member of a BTTS is an antibody-based binding member, the BTTS can be activated in the presence of a binding partner to the antibody-based binding member, including e.g., an antigen specifically bound by the antibody-based binding member. In some instances, antibody-based binding member may be defined, as is commonly done in the relevant art, based on the antigen bound by the antibody-based binding member, including e.g., where the antibody-based binding member is described as an "anti-" antigen antibody, e.g., an anti-priming antigen antibody (e.g., an anti-IL13RA2 antibody, anti-IL13RA1 antibody, anti-Neuroligin antibody, anti-NRXN1 antibody, anti-PTPRZ1 antibody, anti-NRCAM antibody, anti-CDH10 antibody, anti-PCDHGC5 antibody, anti-CD70 antibody anti-CSPG5 antibody, anti-BCAN antibody, anti-GRM3 antibody, anti-CRB1 antibody, anti-GAP43 antibody, anti-ATP1B2 antibody, anti-PTPRZ1-MET fusion antibody, etc.). Accordingly, antibody-based binding members suitable for inclusion in a BTTS or an antigen-specific therapeutic of the present methods can have a variety of antigen-binding specificities.

The components of BTTSs, employed in the described methods, and the arrangement of the components of the switch relative to one another will vary depending on many factors including but not limited to e.g., the desired binding trigger, the activity of the intracellular domain, the overall function of the BTTS, the broader arrangement of a molecular circuit comprising the BTTS, etc. The first binding member may include but is not limited to e.g., those agents that bind an antigen described herein. The intracellular domain may include but is not limited e.g., those intracellular domains that activate or repress transcription at a regulatory sequence, e.g., to induce or inhibit expression of a downstream component of a particular circuit.

The binding transducer of BTTSs will also vary depending on the desired method of transduction of the binding signal. Generally, binding transducers may include those polypeptides and/or domains of polypeptides that transduce an extracellular signal to intracellular signaling e.g., as performed by the receptors of various signal transduction pathways. Transduction of a binding signal may be achieved through various mechanisms including but not limited to e.g., binding-induced proteolytic cleavage, binding-induced phosphorylation, binding-induced conformational change, etc. In some instances, a binding-transducer may contain a ligand-inducible proteolytic cleavage site such that upon binding the binding-signal is transduced by cleavage of the BTTS, e.g., to liberate an intracellular domain. For example, in some instances, a BTTS may include a Notch derived cleavable binding transducer, such as, e.g., a chimeric notch receptor polypeptide as described herein.

In other instances, the binding signal may be transduced in the absence of inducible proteolytic cleavage. Any signal transduction component or components of a signaling transduction pathway may find use in a BTTS whether or not proteolytic cleavage is necessary for signal propagation. For example, in some instances, a phosphorylation-based binding transducer, including but not limited to e.g., one or more signal transduction components of the Jak-Stat pathway, may find use in a non-proteolytic BTTS.

For simplicity, BTTSs, including but not limited to chimeric notch receptor polypeptides, are described primarily as single polypeptide chains. However, BTTSs, including chimeric notch receptor polypeptides, may be divided or split across two or more separate polypeptide chains where the joining of the two or more polypeptide chains to form a functional BTTS, e.g., a chimeric notch receptor polypeptide, may be constitutive or conditionally controlled. For example, constitutive joining of two portions of a split BTTS may be achieved by inserting a constitutive heterodimerization domain between the first and second portions of the split polypeptide such that upon heterodimerization the split portions are functionally joined.

Useful BTTSs that may be employed in the subject methods include, but are not limited to modular extracellular sensor architecture (MESA) polypeptides. A MESA polypeptide comprises: a) a ligand binding domain; b) a transmembrane domain; c) a protease cleavage site; and d) a functional domain. The functional domain can be a transcription regulator (e.g., a transcription activator, a transcription repressor). In some cases, a MESA receptor comprises two polypeptide chains. In some cases, a MESA receptor comprises a single polypeptide chain. Non-limiting examples of MESA polypeptides are described in, e.g., U.S. Patent Publication No. 2014/0234851; the disclosure of which is incorporated herein by reference in its entirety.

Useful BTTSs that may be employed in the subject methods include, but are not limited to polypeptides employed in the TANGO assay. The subject TANGO assay employs a TANGO polypeptide that is a heterodimer in which a first polypeptide comprises a tobacco etch virus (Tev) protease and a second polypeptide comprises a Tev proteolytic cleavage site (PCS) fused to a transcription factor. When the two polypeptides are in proximity to one another, which proximity is mediated by a native protein-protein interaction, Tev cleaves the PCS to release the transcription factor. Non-limiting examples of TANGO polypeptides are described in, e.g., Barnea et al. (Proc Natl Acad Sci USA. 2008 Jan. 8; 105(1):64-9); the disclosure of which is incorporated herein by reference in its entirety.

Useful BTTSs that may be employed in the subject methods include, but are not limited to von Willebrand Factor (vWF) cleavage domain-based BTTSs, such as but not limited to e.g., those containing a unmodified or modified vWF A2 domain. A subject vWF cleavage domain-based BTTS will generally include: an extracellular domain comprising a first member of a binding pair; a von Willebrand Factor (vWF) cleavage domain comprising a proteolytic cleavage site; a cleavable transmembrane domain and an intracellular domain. Non-limiting examples of vWF cleavage domains and vWF cleavage domain-based BTTSs are described in Langridge & Struhl (Cell (2017) 171(6): 1383-1396); the disclosure of which is incorporated herein by reference in its entirety.

Useful BTTSs that may be employed in the subject methods include, but are not limited to chimeric Notch receptor polypeptides, such as but not limited to e.g., synNotch polypeptides, non-limiting examples of which are described in PCT Pub. No. WO 2016/138034, U.S. Pat. Nos. 9,670,281, 9,834,608, Roybal et al. Cell (2016) 167(2):419-432, Roybal et al. Cell (2016) 164(4):770-9, and Morsut et al. Cell (2016) 164(4):780-91; the disclosures of which are incorporated herein by reference in their entirety.

SynNotch polypeptides are generally proteolytically cleavable chimeric polypeptides that generally include: a) an extracellular domain comprising a specific binding member; b) a proteolytically cleavable Notch receptor polypeptide comprising one or more proteolytic cleavage sites; and c) an intracellular domain. Binding of the specific binding member by its binding partner generally induces cleavage of the synNotch at the one or more proteolytic cleavage sites, thereby releasing the intracellular domain. In some instances, the instant methods may include where release of the intracellular domain triggers (i.e., induces) the production of an encoded payload, the encoding nucleic acid sequence of which is contained within the cell. Depending on the particular context, the produced payload is then generally expressed on the cell surface or secreted. SynNotch polypeptides generally include at least one sequence that is heterologous to the Notch receptor polypeptide (i.e., is not derived from a Notch receptor), including e.g., where the extracellular domain is heterologous, where the intracellular domain is heterologous, where both the extracellular domain and the intracellular domain are heterologous to the Notch receptor, etc.

Useful synNotch BTTSs will vary in the domains employed and the architecture of such domains. SynNotch polypeptides will generally include a Notch receptor polypeptide that includes one or more ligand-inducible proteolytic cleavage sites. The length of Notch receptor polypeptides will vary and may range in length from about 50 amino acids or less to about 1000 amino acids or more.

In some cases, the Notch receptor polypeptide present in a synNotch polypeptide has a length of from 50 amino acids (aa) to 1000 aa, e.g., from 50 aa to 75 aa, from 75 aa to 100 aa, from 100 aa to 150 aa, from 150 aa to 200 aa, from 200 aa to 250 aa, from 250 a to 300 aa, from 300 aa to 350 aa, from 350 aa to 400 aa, from 400 aa to 450 aa, from 450 aa to 500 aa, from 500 aa to 550 aa, from 550 aa to 600 aa, from 600 aa to 650 aa, from 650 aa to 700 aa, from 700 aa to 750 aa, from 750 aa to 800 aa, from 800 aa to 850 aa, from 850 aa to 900 aa, from 900 aa to 950 aa, or from 950 aa to 1000 aa. In some cases, the Notch receptor polypeptide present in a synNotch polypeptide has a length of from 300 aa to 400 aa, from 300 aa to 350 aa, from 300 aa to 325 aa, from 350 aa to 400 aa, from 750 aa to 850 aa, from 50 aa to 75 aa. In some cases, the Notch receptor polypeptide has a length of from 310 aa to 320 aa, e.g., 310 aa, 311 aa, 312 aa, 313 aa, 314 aa, 315 aa, 316 aa, 317 aa, 318 aa, 319 aa, or 320 aa. In some cases, the Notch receptor polypeptide has a length of 315 aa. In some cases, the Notch receptor polypeptide has a length of from 360 aa to 370 aa, e.g., 360 aa, 361 aa, 362 aa, 363 aa 364 aa, 365 aa, 366 aa, 367 aa, 368 aa, 369 aa, or 370 aa. In some cases, the Notch receptor polypeptide has a length of 367 aa.

In some cases, a Notch receptor polypeptide comprises an amino acid sequence having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a Notch receptor. In some instances, the Notch regulatory region of a Notch receptor polypeptide is a mammalian Notch regulatory region, including but not limited to e.g., a mouse Notch (e.g., mouse Notch1, mouse Notch2, mouse Notch3 or mouse Notch4) regulatory region, a rat Notch regulatory region (e.g., rat Notch1, rat Notch2 or rat Notch3), a human Notch regulatory region (e.g., human Notch1, human Notch2, human Notch3 or human Notch4), and the like or a Notch regulatory region derived from a mammalian Notch regulatory region and having at least 50%, at least 55%, at least 60%, at least 65%, at least 70%, at least 75%, at least 80%, at least 85%, at least 90%, at least 95%, at least 98%, at least 99%, or 100%, amino acid sequence identity to the amino acid sequence of a mammalian Notch regulatory region of a mammalian Notch receptor amino acid sequence.

Subject Notch regulatory regions may include or exclude various components (e.g., domains, cleavage sites, etc.) thereof. Examples of such components of Notch regulatory regions that may be present or absent in whole or in part, as appropriate, include e.g., one or more EGF-like repeat domains, one or more Lin12/Notch repeat domains, one or more heterodimerization domains (e.g., HD-N or HD-C), a transmembrane domain, one or more proteolytic cleavage sites (e.g., a furin-like protease site (e.g., an 51 site), an ADAM-family protease site (e.g., an S2 site) and/or a gamma-secretase protease site (e.g., an S3 site)), and the like. Notch receptor polypeptides may, in some instances, exclude all or a portion of one or more Notch extracellular domains, including e.g., Notch-ligand binding domains such as Delta-binding domains. Notch receptor polypeptides may, in some instances, include one or more non-functional versions of one or more Notch extracellular domains, including e.g., Notch-ligand binding domains such as Delta-binding domains. Notch receptor polypeptides may, in some instances, exclude all or a portion of one or more Notch intracellular domains, including e.g., Notch Rbp-associated molecule domains (i.e., RAM domains), Notch Ankyrin repeat domains, Notch transactivation domains, Notch PEST domains, and the like. Notch receptor polypeptides may, in some instances, include one or more non-functional versions of one or more Notch intracellular domains, including e.g., non-functional Notch Rbp-associated molecule domains (i.e., RAM domains), non-functional Notch Ankyrin repeat domains, non-functional Notch transactivation domains, non-functional Notch PEST domains, and the like.

Non-limiting examples of particular synNotch BTTSs, the domains thereof, and suitable domain arrangements are described in PCT Pub. Nos. WO 2016/138034, WO 2017/193059, WO 2018/039247 and U.S. Pat. Nos. 9,670,281 and 9,834,608; the disclosures of which are incorporated herein by reference in their entirety.

Domains of a useful BTTS, e.g., the extracellular domain, the binding-transducer domain, the intracellular domain, etc., may be joined directly, i.e., with no intervening amino acid residues or may include a peptide linker that joins two domains. Peptide linkers may be synthetic or naturally derived including e.g., a fragment of a naturally occurring polypeptide.

A peptide linker can vary in length of from about 3 amino acids (aa) or less to about 200 aa or more, including but not limited to e.g., from 3 aa to 10 aa, from 5 aa to 15 aa, from 10 aa to 25 aa, from 25 aa to 50 aa, from 50 aa to 75 aa, from 75 aa to 100 aa, from 100 aa to 125 aa, from 125 aa to 150 aa, from 150 aa to 175 aa, or from 175 aa to 200 aa. A peptide linker can have a length of from 3 aa to 30 aa, e.g., 3, 4, 5, 6, 7, 8, 9, 10, 11, 12, 13, 14, 15, 16, 17, 18, 19, 20, 21, 22, 23, 24, 25, 26, 27, 28, 29, or 30 aa. A peptide linker can have a length of from 5 aa to 50 aa, e.g., from 5 aa to 40 aa, from 5 aa to 35 aa, from 5 aa to 30 aa, from 5 aa to 25 aa, from 5 aa to 20 aa, from 5 aa to 15 aa or from 5 aa to 10 aa.

In some instances, a BTTS may have an extracellular domain that includes a first member of a specific binding pair that binds a second member of the specific binding pair, wherein the extracellular domain does not include any additional first or second member of a second specific binding pair. For example, in some instances, a BTTS may have an extracellular domain that includes a first antigen-binding domain that binds an antigen, wherein the extracellular domain does not include any additional antigen-binding domains and does not bind any other antigens. A subject BTTS may, in some instances, include only a single extracellular domain. Accordingly, an employed BTTS may be specific for a single antigen and only specific for the single antigen. Such, BTTSs may be referred to as a "single antigen BTTS". In some instances, a "dual antigen BTTS" may be employed.

In some instances, a BTTS may have an extracellular domain that includes the first or second members of two or more specific binding pairs. For example, in some instances, a BTTS may have an extracellular domain that includes a first antigen-binding domain and a second antigen-binding domain that are different such that the extracellular domain is specific for two different antigens. In some instances, a BTTS may have two or more extracellular domains that each includes the first or second members of two different specific binding pairs. For example, in some instances, a BTTS may have a first extracellular domain that includes a first antigen-binding domain and a second extracellular domain that includes a second antigen-binding domain where the two different antigen binding domains are each specific for a different antigen. As such, the BTTS may be specific for two different antigens.

A BTTS specific for two or more different antigens, containing either two extracellular domains or one extracellular domain specific for two different antigens, may be configured such that the binding of either antigen to the BTTS is sufficient to trigger activation of the BTTS, e.g., proteolytic cleavage of a cleavage domain of the BTTS, e.g., releasing an intracellular domain of the BTTS. Such a BTTS, capable of being triggered by any of two or more antigens, may find use in the described circuits as a component of a logic gate containing OR functionality. In some instances, a BTTS specific for two different antigens may be referred to as a "two-headed BTTS" or a tandem BTTS (or tanBTTS). For example, in some instances, a synNotch BTTS configured to bind two or more different antigens may be referred to as a tandem SynNotch or tanSynNotch. BTTS specific for multiple antigens will not be limited to only two antigens and may, e.g., be specific for and/or triggered by more than two antigens, including e.g., three or more, four or more, five or more, etc.

Methods of Making

The present disclosure further includes methods of making the nucleic acids, circuits, and cells employed in the herein described methods. In making the subject nucleic acids and circuits, and components thereof, any convenient methods of nucleic acid manipulation, modification and amplification (e.g., collectively referred to as "cloning") may be employed. In making the subject cells, containing the nucleic acids encoding the described circuits, convenient methods of transfection, transduction, culture, etc., may be employed.

A nucleotide sequence encoding all or a portion of the components of a circuit of the present disclosure can be present in an expression vector and/or a cloning vector. Where a subject circuit or component thereof is split between two or more separate polypeptides, nucleotide sequences encoding the two or more polypeptides can be cloned in the same or separate vectors. An expression vector can include a selectable marker, an origin of replication, and other features that provide for replication and/or maintenance of the vector. Suitable expression vectors include, e.g., plasmids, viral vectors, and the like.

Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, in some embodiments, a nucleic acid comprising a nucleotide sequence encoding a circuit or component thereof of the present disclosure will in some embodiments be DNA or RNA, e.g., in vitro synthesized DNA, recombinant DNA, in vitro synthesized RNA, recombinant RNA, etc. Methods for in vitro synthesis of DNA/RNA are known in the art; any known method can be used to synthesize DNA/RNA comprising a desired sequence. Methods for introducing DNA/RNA into a host cell are known in the art. Introducing DNA/RNA into a host cell can be carried out in vitro or ex vivo or in vivo. For example, a host cell (e.g., an NK cell, a cytotoxic T lymphocyte, etc.) can be transduced, transfected or electroporated in vitro or ex vivo with DNA/RNA comprising a nucleotide sequence encoding all or a portion of a circuit of the present disclosure.

Methods of the instant disclosure may further include culturing a cell genetically modified to encode a circuit of the instant disclosure including but not limited to e.g., culturing the cell prior to administration, culturing the cell in vitro or ex vivo (e.g., the presence or absence of one or more antigens), etc. Any convenient method of cell culture may be employed whereas such methods will vary based on various factors including but not limited to e.g., the type of cell being cultured, the intended use of the cell (e.g., whether the cell is cultured for research or therapeutic purposes), etc. In some instances, methods of the instant disclosure may further include common processes of cell culture including but not limited to e.g., seeding cell cultures, feeding cell cultures, passaging cell cultures, splitting cell cultures, analyzing cell cultures, treating cell cultures with a drug, harvesting cell cultures, etc.

Methods of the instant disclosure may, in some instances, further include receiving and/or collecting cells that are used in the subject methods. In some instances, cells are collected from a subject. Collecting cells from a subject may include obtaining a tissue sample from the subject and enriching, isolating and/or propagating the cells from the tissue sample. Isolation and/or enrichment of cells may be performed using any convenient method including e.g., isolation/enrichment by culture (e.g., adherent culture, suspension culture, etc.), cell sorting (e.g., FACS, microfluidics, etc.), and the like. Cells may be collected from any convenient cellular tissue sample including but not limited to e.g., blood (including e.g., peripheral blood, cord blood, etc.), bone marrow, a biopsy, a skin sample, a cheek swab, etc. In some instances, cells are received from a source including e.g., a blood bank, tissue bank, etc. Received cells may have been previously isolated or may be received as part of a tissue sample thus isolation/enrichment may be performed after receiving the cells and prior to use. In certain instances, received cells may be non-primary cells including e.g., cells of a cultured cell line. Suitable cells for use in the herein described methods are further detailed herein.

Nucleic Acids

As summarized above, the present disclosure provides nucleic acids encoding a circuit for treating a subject for a brain disease or disorder.

Such nucleic acids may be configured such that the sequence encoding the targeting antigen-specific therapeutic is operably linked to a regulatory sequence responsive to activation of the BTTS. Provided are nucleic acids encoding essentially any circuit employing trans-targeting utilizing recognition of a priming antigen expressed on a first brain cell that also expresses a targeting antigen, including but not limited to those circuits specifically described herein. Encompassed are isolated nucleic acids encoding the subject circuits as well as various configurations containing such nucleic acids, such as vectors, e.g., expression cassettes, recombinant expression vectors, viral vectors, and the like.

Recombinant expression vectors of the present disclosure include those comprising one or more of the described nucleic acids. A nucleic acid comprising a nucleotide sequence encoding all or a portion of the components of a circuit of the present disclosure will in some embodiments be DNA, including, e.g., a recombinant expression vector. A nucleic acid comprising a nucleotide sequence encoding all or a portion of the components of a circuit of the present disclosure will in some embodiments be RNA, e.g., in vitro synthesized RNA.

As summarized above, in some instances, the subject circuits may make use of an encoding nucleic acid (e.g., a nucleic acid encoding a BTTS or an antigen-specific therapeutic) that is operably linked to a regulatory sequence such as a transcriptional control element (e.g., a promoter; an enhancer; etc.). In some cases, the transcriptional control element is inducible. In some cases, the transcriptional control element is constitutive. In some cases, the promoters are functional in eukaryotic cells. In some cases, the promoters are cell type-specific promoters. In some cases, the promoters are tissue-specific promoters.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) *Methods in Enzymology,* 153:516-544).

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

In some instances, a transcriptional control element of a herein described nucleic acid may include a cis-acting regulatory sequence. Any suitable cis-acting regulatory sequence may find use in the herein described nucleic acids. For example, in some instances a cis-acting regulatory sequence may be or include an upstream activating sequence or upstream activation sequence (UAS). In some instances, a UAS of a herein described nucleic acid may be a Gal4 responsive UAS.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is an immune cell promoter such as a CD8 cell-specific promoter, a CD4 cell-specific promoter, a neutrophil-specific promoter, or an NK-specific promoter. For example, a CD4 gene promoter can be used; see, e.g., Salmon et al. (1993) *Proc. Natl. Acad. Sci. USA* 90: 7739; and Marodon et al. (2003) *Blood* 101:3416. As another example, a CD8 gene promoter can be used. NK cell-specific expression can be achieved by use of an Ncr1 (p46) promoter; see, e.g., Eckelhart et al. (2011) *Blood* 117:1565.

In some instances, an immune cell specific promoter of a nucleic acid of the present disclosure may be a promoter of a B29 gene promoter, a CD14 gene promoter, a CD43 gene promoter, a CD45 gene promoter, a CD68 gene promoter, a IFN-β gene promoter, a WASP gene promoter, a T-cell receptor β-chain gene promoter, a V9 γ (TRGV9) gene promoter, a V2 δ (TRDV2) gene promoter, and the like.

In some cases, a nucleic acid comprising a nucleotide sequence encoding a circuit of the present disclosure, or one or more components thereof, is a recombinant expression vector or is included in a recombinant expression vector. In some embodiments, the recombinant expression vector is a viral construct, e.g., a recombinant adeno-associated virus (AAV) construct, a recombinant adenoviral construct, a recombinant lentiviral construct, a recombinant retroviral construct, etc. In some cases, a nucleic acid comprising a nucleotide sequence encoding a circuit of the present disclosure, or one or more components thereof, is a recombinant lentivirus vector. In some cases, a nucleic acid comprising a nucleotide sequence encoding a circuit of the present disclosure, or one or more components thereof, is a recombinant AAV vector.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., Hum Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, the vector is a lentivirus vector. Also suitable are transposon-mediated vectors, such as piggyback and sleeping beauty vectors.

In some instances, nucleic acids of the present disclosure may have a single sequence encoding two or more polypeptides where expression of the two or more polypeptides is made possible by the presence of a sequence element between the individual coding regions that facilitates separate expression of the individual polypeptides. Such sequence elements, may be referred to herein as bicistronic-facilitating sequences, where the presence of a bicistronic-facilitating sequence between two coding regions makes possible the expression of a separate polypeptide from each coding region present in a single nucleic acid sequence. In some instances, a nucleic acid may contain two coding regions encoding two polypeptides present in a single nucleic acid with a bicistronic-facilitating sequence between the coding regions. Any suitable method for separate expression of multiple individual polypeptides from a single nucleic acid sequence may be employed and, similarly, any suitable method of bicistronic expression may be employed.

In some instances, a bicistronic-facilitating sequence may allow for the expression of two polypeptides from a single nucleic acid sequence that are temporarily joined by a cleavable linking polypeptide. In such instances, a bicistronic-facilitating sequence may include one or more encoded peptide cleavage sites. Suitable peptide cleavage sites include those of self-cleaving peptides as well as those cleaved by a separate enzyme. In some instances, a peptide cleavage site of a bicistronic-facilitating sequence may include a furin cleavage site (i.e., the bicistronic-facilitating sequence may encode a furin cleavage site).

In some instances, the bicistronic-facilitating sequence may encode a self-cleaving peptide sequence. Useful self-cleaving peptide sequences include but are not limited to e.g., peptide 2A sequences, including but not limited to e.g., the T2A sequence.

In some instances, a bicistronic-facilitating sequence may include one or more spacer encoding sequences. Spacer encoding sequences generally encode an amino acid spacer, also referred to in some instances as a peptide tag. Useful spacer encoding sequences include but are not limited to e.g., V5 peptide encoding sequences, including those sequences encoding a V5 peptide tag.

Multi- or bicistronic expression of multiple coding sequences from a single nucleic acid sequence may make use of but is not limited to those methods employing furin cleavage, T2A, and V5 peptide tag sequences. For example, in some instances, an internal ribosome entry site (IRES) based system may be employed. Any suitable method of bicistronic expression may be employed including but not limited to e.g., those described in Yang et al. (2008) Gene Therapy. 15(21):1411-1423; Martin et al. (2006) BMC Biotechnology. 6:4; the disclosures of which are incorporated herein by reference in their entirety.

Cells

As summarized above, the present disclosure also provides immune cells. Immune cells of the present disclosure include those that contain one or more of the described nucleic acids, expression vectors, etc., encoding a described circuit. Immune cells of the present disclosure include mammalian immune cells including e.g., those that are genetically modified to produce the components of a circuit of the present disclosure or to which a nucleic acid, as described above, has been otherwise introduced. In some instances, the subject immune cells have been transduced with one or more nucleic acids and/or expression vectors to express one or more components of a circuit of the present disclosure.

Suitable mammalian immune cells include primary cells and immortalized cell lines. Suitable mammalian cell lines include human cell lines, non-human primate cell lines, rodent (e.g., mouse, rat) cell lines, and the like. In some instances, the cell is not an immortalized cell line, but is instead a cell (e.g., a primary cell) obtained from an individual. For example, in some cases, the cell is an immune cell, immune cell progenitor or immune stem cell obtained from an individual. As an example, the cell is a lymphoid cell, e.g., a lymphocyte, or progenitor thereof, obtained from an individual. As another example, the cell is a cytotoxic cell, or progenitor thereof, obtained from an individual. As another example, the cell is a stem cell or progenitor cell obtained from an individual.

As used herein, the term "immune cells" generally includes white blood cells (leukocytes) which are derived from hematopoietic stem cells (HSC) produced in the bone marrow. "Immune cells" includes, e.g., lymphoid cells, i.e., lymphocytes (T cells, B cells, natural killer (NK) cells), and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), T-regulatory cells (Treg) and gamma-delta T cells. A "cytotoxic cell" includes CD8+ T cells, natural-killer (NK) cells, and neutrophils, which cells are capable of mediating cytotoxicity responses. "B cell" includes mature and immature cells of the B cell lineage including e.g., cells that express CD19 such as Pre B cells, Immature B cells, Mature B cells, Memory B cells and plasmablasts. Immune cells also include B cell progenitors such as Pro B cells and B cell lineage derivatives such as plasma cells.

Immune cells encoding a circuit of the present disclosure may be generated by any convenient method. Nucleic acids encoding one or more components of a subject circuit may be stably or transiently introduced into the subject immune cell, including where the subject nucleic acids are present only temporarily, maintained extrachromosomally, or integrated into the host genome. Introduction of the subject nucleic acids and/or genetic modification of the subject immune cell can be carried out in vivo, in vitro, or ex vivo.

In some cases, the introduction of the subject nucleic acids and/or genetic modification is carried out ex vivo. For example, a T lymphocyte, a stem cell, or an NK cell is obtained from an individual; and the cell obtained from the individual is modified to express components of a circuit of the present disclosure. The modified cell can thus be redirected to one or more antigens of choice, as defined by the one or more antigen binding domains present on the introduced components of the circuit. In some cases, the modified cell is modulated ex vivo. In other cases, the cell is introduced into (e.g., the individual from whom the cell was obtained) and/or already present in an individual; and the cell is modulated in vivo, e.g., by administering a nucleic acid or vector to the individual in vivo.

Circuits

As summarized above, the present disclosure also provides circuits encoded by nucleic acid sequences, also referred to in some instances as molecular circuits. Such circuits may, in some instances, be present and/or configured in expression vectors and/or expression cassettes. The subject nucleic acids of the present circuits may, in some instances, be contained within a vector, including e.g., viral and non-viral vectors. Such circuits may, in some instances, be present in cells, such as immune cells, or may be introduced into cells by various means, including e.g., through the use of a viral vector. Cells may, in some instances, be genetically modified to encode a subject circuit, where such modification may be effectively permanent (e.g., integrated) or transient as desired.

Encoded components of the circuits of the present disclosure will generally include at a minimum at least one encoded BTTS and at least one encoded therapeutic protein. The expression of a component of a circuit of the present disclosure may be dependent upon the state (i.e., active/inactive state) of another component of the circuit. For example, the expression of the therapeutic may be dependent upon the activation of a BTTS, where the BTTS is activated by binding to an antigen for which the BTTS is specific. In some instances, dependency of one component of the circuit on another may be mediated by a regulatory sequence. For example, a sequence encoding a second component of a circuit may be operably linked to a regulatory sequence that is responsive to the activation of a first component of the circuit, thus linking the expression of the second component to the activation of the first.

The use of a BTTS in a circuit of the present disclosure facilitates the linking of expression and/or activity to molecular binding events. Systems involving binding-triggered transcriptional switches, and components thereof, have been described in PCT Publication No. WO 2016/138034, US Patent Application Pub. No. US 2016-0264665 A1 and issued U.S. Pat. Nos. 9,670,281 and 9,834,608; the disclosures of which are incorporated by reference herein in their entirety.

Circuits of the present disclosure may be configured in various ways. In some instances, the independent activities and/or induced expression of two or more polypeptides or domains of a single polypeptide may generate a logic gated circuit. Such logic gated circuits may include but are not limited to e.g., "AND gates", "OR gates", "NOT gates" and combinations thereof including e.g., higher order gates including e.g., higher order AND gates, higher order OR gates, higher order NOT gates, higher order combined gates (i.e., gates using some combination of AND, OR and/or NOT gates). In some instances, useful circuits may further include IF/THEN gates.

"AND" gates include where two or more inputs are required for propagation of a signal. For example, in some instances, an AND gate allows signaling through a first input of a first polypeptide or a first polypeptide domain and a second input dependent upon the output of the first input. In an AND gate two inputs, e.g., two antigens, are required for signaling through the circuit.

"OR" gates include where either of two or more inputs may allow for the propagation of a signal. For example, in some instances, an OR gate allows signaling through binding of either of two different antigens. In an OR gate any one input, e.g., either of two antigens, may induce the signaling output of the circuit. In one embodiment, an OR gate may be achieved through the use of two separate molecules or constructs. In another embodiment, an OR gate may be achieved through the use of a single construct that recognizes two antigens, including e.g., a BTTS or an antigen-specific therapeutic (e.g., a CAR or TCR) having two different antigen binding domains that each bind a different antigen and each binding event can independently propagate the signal (e.g., induce expression of a downstream component of the circuit, activate an immune cell, etc.).

"NOT" gates include where an input is capable of preventing the propagation of a signal. For example, in some instances, a NOT gate inhibits signaling through a circuit of the instant disclosure. In one embodiment, a NOT gate may prevent the expression of a component of a circuit, or activation of a particular component of the circuit, e.g., a CAR or a TCR.

"IF/THEN" gates include where the output of the gate depends upon a first input. For example, in some instances, IF a first input is present THEN signaling may proceed through a second input, and where the first input is absent signaling may not proceed. A non-limiting example of a circuit that includes an IF/THEN gate is a circuit having at least two receptors where the first receptor, in response to an input, induces expression of the second receptor, which has some output in response to a second input. As such, IF the first input of the first receptor is present, THEN the second receptor is expressed and signaling can proceed through the second receptor via the second input to produce the output. IF/THEN gates may or may not include an OR component (e.g., a receptor with OR functionality).

Figure 4:
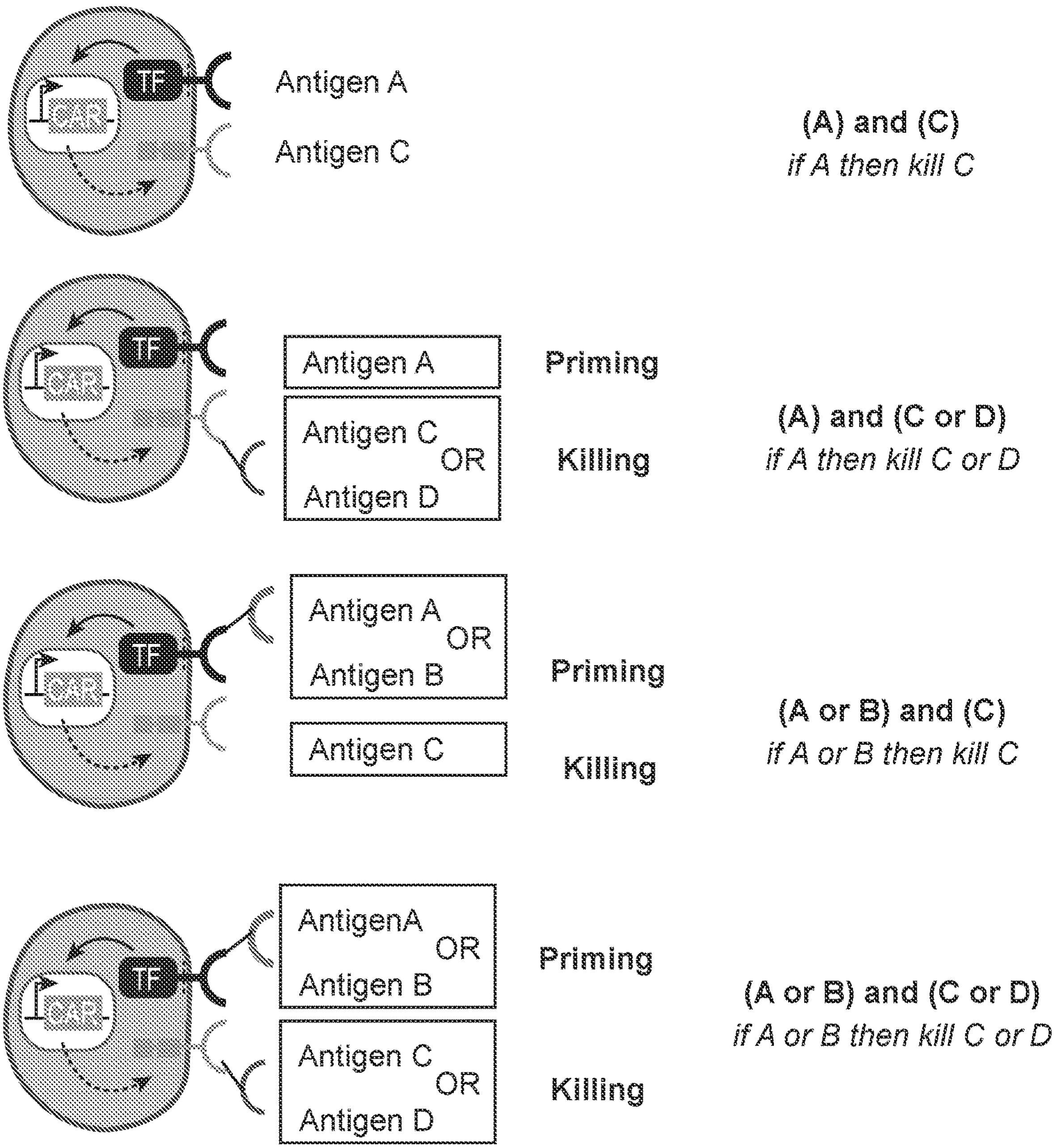
FIG. 4 depicts cells that contain IF/THEN circuits with and without OR gate functionality at the relevant binding triggered transcriptional switch, the antigen-specific therapeutic, or both.

Non-limiting examples of IF/THEN gates, including examples with OR functionality, are depicted in FIG. 4. The circuit depicted in the first (top) cell of FIG. 4 includes a BTTS responsive to antigen "A" and an antigen-specific therapeutic that binds antigen "C". Note that although the antigen-specific therapeutic is depicted as a CAR, the disclosure is not so limited and other antigen-specific therapeutics may be readily substituted. In the first (top) circuit, IF antigen A is present THEN cell killing is induced based on the presence of antigen C.

In various embodiments, OR functionality may be employed, including where one or more components of a subject circuit include an OR functionality. As shown in the second, third and fourth cells depicted in FIG. 4, OR functionality may be provided by a BTTS, an antigen-specific therapeutic, or both having specificity for, and being triggered or activated by, two or more antigens.

For example, in the second (from the top) cell depicted in FIG. 4, a circuit is employed that includes a BTTS responsive to antigen "A" and an antigen-specific therapeutic that binds to, and is activated by, antigen "C" or antigen "D". In such a circuit, IF antigen A is present THEN cell killing is induced based on the presence of antigen C OR antigen D. Note that killing of cells expressing antigen C and antigen D may also be induced, as well as killing of cells that express antigen C alone or antigen D alone.

In the third (from the top) cell depicted in FIG. 4, a circuit is employed that includes a BTTS responsive to antigen "A" or antigen "B" and an antigen-specific therapeutic that binds to, and is activated by, antigen "C". In such a circuit, IF antigen A OR antigen B is present THEN cell killing is induced based on the presence of antigen C. Note that the immune cells encoding the subject circuit may be primed to kill by a cell expressing only antigen A, only antigen B, or both antigens A and B.

In the fourth (bottom) cell depicted in FIG. 4, a circuit is employed that includes a BTTS responsive to antigen "A" or antigen "B" and an antigen-specific therapeutic that binds to, and is activated by, antigen "C" or antigen "D". In such a circuit, IF antigen A OR antigen B is present THEN cell killing is induced based on the presence of antigen C or antigen D. Note that the immune cells encoding the subject circuit may be primed to kill by a cell expressing only antigen A, only antigen B, or both antigens A and B. Also note that killing of cells expressing antigen C and antigen D may also be induced, as well as killing of cells that express antigen C alone or antigen D alone.

In some instances, the use of OR functionality may have certain advantages. For example, the above described circuits having OR gate functionality (i.e., the second, third and fourth cells of FIG. 4) and variations thereof provide resistance to escape and improved efficacy for heterogeneous cancers because, without being bound by theory, to escape a cancer (or tumor) would need to contain, or evolve/produce, a cell that does not express either of the two priming and/or killing antigens.

In some instances, multiple antigen binding domains present on a BTTS or antigen-specific therapeutic may provide an OR gate capability to the herein described molecular circuits. For example, in some instances, a BTTS having two different antigen binding domains may be responsive to a first antigen (e.g., a first priming antigen) OR a second antigen (e.g., a second priming antigen). In some instances, an antigen-specific therapeutic (e.g., a CAR, a TCR, etc.) having two different antigen binding domains may be responsive to a first antigen (e.g., a first targeting antigen) OR a second antigen (e.g., a second targeting antigen).

In some instances, such OR gates may be combined with other gates, including an AND gate. For example, a nucleic acid encoding an OR-gate antigen-specific therapeutic having two different antigen binding domains may be operably linked to a promoter that is responsive to a BTTS which is responsive to a priming antigen. As such, upon binding the priming antigen, the BTTS drives expression of the antigen-specific therapeutic which is responsive to two different antigens, resulting in an AND-OR gate.

In some instances, OR gates may find use in the circuits of the present disclosure to produce an OR gate for two or more targeting antigens (or two or more killing antigens). For example, in some instances, the circuit may be configured such that the cell genetically modified with the circuit contains a nucleic acid sequence encoding an antigen-specific therapeutic that binds to a first targeting/killing antigen or a second targeting/killing antigen expressed by a targeted cancer cell (or expressed by two different targeted cancer cells), thereby producing a cell that is activated, e.g., activated for cell killing, by either the first targeting/killing antigen or the second targeting/killing antigen. In some instances, a circuit of the present disclosure may include nucleic acid sequence encoding a first antigen-specific therapeutic and second antigen-specific therapeutic that each bind to a different targeting/killing antigen.

In some instances, an OR gate may be employed to allow for simultaneous targeting of cells both in trans and in cis. For example, in some instances, a second killing antigen to which an OR gate is directed may be expressed by the priming cell. In some instances, an OR gate for targeting may be employed to target two antigens that that are not mutually exclusively expressed within brain cells.

Kits

The present disclosure provides a kit for carrying out a method as described herein and/or constructing one or more circuits, components thereof, nucleic acids encoding a circuit or a component thereof, etc. In some cases, a subject kit comprises a vector, e.g., an expression vector or a delivery vector, comprising a nucleotide sequence encoding a circuit of the present disclosure or one or more portions thereof. Delivery vectors may be provided in a delivery device or may be provided separately, e.g., as a kit that includes the delivery vector and the delivery device as separate components of the kit.

In some cases, a subject kit comprises a cell, e.g., a host cell or host cell line, that is or is to be genetically modified with a nucleic acid comprising nucleotide sequence encoding a circuit of the present disclosure or a portion thereof. In some cases, a subject kit comprises a cell, e.g., a host cell, that is or is to be genetically modified with a recombinant expression vector comprising a nucleotide sequence encoding a circuit of the present disclosure. Kit components can be in the same container, or in separate containers.

Any of the above-described kits can further include one or more additional reagents, where such additional reagents can be selected from: a dilution buffer; a reconstitution solution; a wash buffer; a control reagent; a control expression vector; a nucleic acid encoding a negative control (e.g., a circuit that lacks the one or more critical elements); a nucleic acid encoding a positive control polypeptide; and the like.

In addition to above-mentioned components, a subject kit can further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

EMBODIMENTS

Alternative brain-selective extracellular antigens including brevican core protein (BCAN) or chondroitin sulfate proteoglycan (CSPG5) can be used instead of MOG, CDH10, PTPRZ1 or NRCAM in any embodiment described above or below.

Embodiment 1. A cell comprising a recombinant nucleic acid encoding a transmembrane protein that has an extracellular binding domain that specifically binds to a brain-selective extracellular antigen, wherein the cell does not comprise a nucleic acid encoding an antigen-specific therapeutic that binds to a killing antigen expressed by a glioblastoma.

Embodiment 2. The cell of embodiment 1, wherein the brain-selective extracellular antigen is MOG, CDH10, PTPRZ1 or NRCAM.

Embodiment 3. The cell of embodiment 1 or 2, wherein the extracellular binding domain is the variable domain of an antibody that specifically binds to the brain-selective extracellular antigen.

Embodiment 4. The cell of any of any prior embodiment, wherein the transmembrane protein is a binding-triggered transcriptional switch and the cell further comprises a nucleic acid comprising: (i) a coding sequence encoding a therapeutic protein and (ii) a regulatory sequence, wherein the regulatory sequence is operably linked to the coding sequence and is responsive to activation of the a binding-triggered transcriptional switch.

Embodiment 5. The system of any prior embodiment, wherein the binding-triggered transcriptional switch is one or more polypeptides that undergo proteolytic cleavage upon binding to the brain-selective extracellular antigen to release a gene expression regulator that activates transcription of the therapeutic protein.

Embodiment 6. The cell of embodiment 5, wherein the binding-triggered transcriptional switch is a SynNotch receptor, an A2 receptor, a MESA, or another receptor that undergoes binding induced proteolytic cleavage.

Embodiment 7. The cell of embodiment 6, wherein the binding-triggered transcriptional switch comprises:

(i) an extracellular domain that binds to the brain-selective extracellular antigen;

(ii) a proteolytically cleavable sequence comprising one or more proteolytic cleavage sites; and (iii) an intracellular domain, wherein binding of the extracellular domain of (i) to the brain-selective extracellular antigen induces cleavage of the proteolytically cleavable sequence at the one or more proteolytic cleavage sites to release the intracellular domain, and wherein the released intracellular domain induces expression of the therapeutic protein of (i) via the regulatory sequence of (ii).

Embodiment 8. The cell of any of embodiments 4-7, wherein the therapeutic protein of (i) is a protein that, when expressed, is secreted by the cell or on the surface of the cell.

Embodiment 9. The cell of any of embodiments 4-8, wherein the therapeutic protein is a protein that, when expressed on the surface of an immune cell, activates the immune cell or inhibits activation of the immune cell.

Embodiment 10. The cell of any of embodiments 4-9, wherein the therapeutic protein is an antigen-specific therapeutic.

Embodiment 11. The cell of embodiment 10, wherein the antigen-specific therapeutic is a chimeric antigen receptor (CAR) or a T cell receptor (TCR), and wherein binding of the transmembrane protein to the brain-selective extracellular antigen induces expression of the CAR or TCR.

Embodiment 12. The cell of embodiment 10, wherein the antigen-specific therapeutic is an inhibitory chimeric antigen receptor (iCAR), wherein binding of the transmembrane protein to the extracellular antigen induces expression of the iCAR.

Embodiment 13. The cell of embodiment 10, wherein the antigen-specific therapeutic is another binding-triggered transcriptional switch.

Embodiment 14. The cell of any of embodiments 4-7, wherein the therapeutic protein of (i) is a protein that, when expressed, is intracellular.

Embodiment 15. The cell of any of embodiments 1-8 or 10, wherein the antigen-specific therapeutic is an antibody.

Embodiment 16. The cell of any of embodiments 1-10, wherein therapeutic protein is an inhibitory immunoreceptor.

Embodiment 17. The cell of any of embodiments 1-10, wherein the therapeutic protein is a secreted peptide or enzyme.

Embodiment 18. The cell of any of embodiments 1-10, wherein the transmembrane protein is an inhibitory chimeric antigen receptor (iCAR), wherein binding of the brain-selective extracellular antigen inhibits activation of the immune cell on which the iCAR is expressed.

Embodiment 19. The cell of any of embodiments 1-18, wherein the cell is an immune cell.

Embodiment 20. The cell of any of embodiments 1-19, wherein the cell is a myeloid or lymphoid cell.

Embodiment 21. The cell of embodiment 20, wherein the lymphoid cell a T lymphocyte, a B lymphocyte or a Natural Killer cell.

Embodiment 22. The cell of any of embodiments 1-18, wherein the cell is not an immune cell.

Embodiment 23. A method of treating a subject for a disease, the method comprising: administering to the subject a cell of any of embodiments 1-22.

Embodiment 24. The method of embodiment 23, wherein the disease is a disease of the brain and/or central nervous tissue.

Embodiment 25. The method of embodiment 24, wherein the subject has medulloblastoma, diffuse midline glioma, ependymoma, craniopharyngiom, embryonal tumor, pineoblastoma, brainstem glioma, choroid plexus carcinoma, germ cell tumor, pituitary adenoma, acoustic neuroma, meningioma, oligodendroglioma, haemangioblastoma, CNS lymphoma, or non-GBM astrocytoma.

Embodiment 26. The method of embodiment 23, wherein the subject has Alzheimer's disease, stroke, brain and spinal cord injury, brain cancer, HIV infection in the brain, ataxia-producing disorders, amyotrophic lateral sclerosis (ALS), Huntington disease, childhood inborn genetic errors affecting the brain, Parkinson's disease, or multiple sclerosis.

Embodiment 27. The method of embodiment 23, wherein the disease is a cancer from a non-brain or CNS tissue that has metastasized to the brain.

Embodiment 28. Any prior embodiment, wherein the brain-selective extracellular is MOG.

Embodiment 29. Any prior embodiment, wherein the brain-selective extracellular is CDH10.

Embodiment 30. Any prior embodiment, wherein the brain-selective extracellular is PTPRZ1.

Embodiment 31. Any prior embodiment, wherein the brain-selective extracellular is NRCAM.

Embodiment 32. Any prior embodiment, wherein the brain-selective extracellular is antigen brevican core protein (BCAN).

Embodiment 33. Any prior embodiment, wherein the brain-selective extracellular is chondroitin sulfate proteoglycan 5 (CSPG5).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Treatment Using a Brain-Specific Circuit

As noted above, the present cell expresses a transmembrane protein that, in some embodiments, may be a binding triggered transcriptional switch (BTTS) that activates expression of a therapeutic protein. In some of these embodiments, the therapeutic protein may be an antigen-specific immune cell receptor (e.g., a CAR). These latter embodiments are described in greater detail below. However, the transmembrane protein does not need to be a BTTS and the therapeutic protein does not need to be an immune cell receptor. As such, the following description should not limit this disclosure in any way.

In this example, a brain-selective antigen (MOG, CDH10, PTPRZ1 or NRCAM) was used to target a disease-specific antigen (which may be a "killing antigen", depending on how the circuit is used) to the brain. This example employs a brain-specific priming antigen selected from MOG, CDH10, PTPRZ1 or NRCAM to prime the expression of a second, therapeutic molecule that that targets diseased cells based on a second antigen (or combination of antigens) that is expressed on the diseased cells. This approach is effective even if the second antigen(s) is not perfectly disease-specific and is expressed in non-brain tissues. Without being bound by theory, this approach is believed to harness two or more imperfect antigens (in this case a brain-specific antigen and a disease-specific antigen) to develop a combinatorial T cell that shows both high selectivity and insensitivity to antigen expression heterogeneity.

Figure 1A:
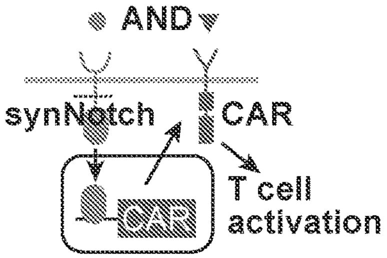
FIG. 1A-1D depict examples of brain-specific treatment circuits, with or without diffusible components, and employing antigen recognition and therapeutic targeting using a brain-specific antigen and a targeting antigen expressed diseased cells.
Figure 1B:
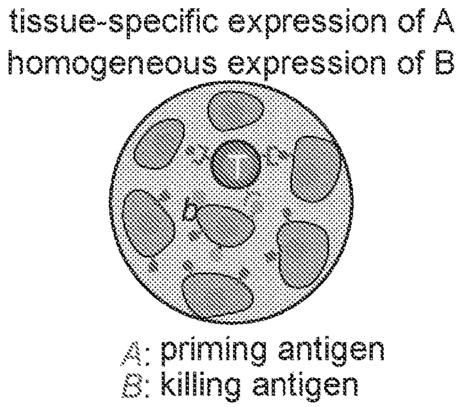

In this example, a circuit was designed in which a therapeutic cell is primed on a brain-specific antigen, thereby inducing expression of a therapeutic protein (e.g., a CAR, a BiTE, etc.) that is then delivered to nearby cells that express a targeting antigen (see FIG. 1A). In this example the circuit is primed using a brain-specific antigen and kills cells in a "killing zone" around the priming antigen cells by targeting an antigen on the diseased cells (see FIG. 1B). The killing zone size is tunable based on a variety of factors such as, but not limited to, killing receptor (e.g., CAR) stability or the use of extracellular diffusible agents as killing payload (e.g. bispecific adapters) (see FIG. 1C and FIG. 1D).

As depicted in FIG. 1A-1D, priming of therapeutic cells, such as a cell engineered with a circuit as depicted in FIG. 1A, creates a zone around the therapeutic cell such that cells expressing the target antigen are targeted even when such cells do not express the priming antigen. An example of this scenario is schematized in FIG. 1B, which shows a therapeutic cell, shown as a T cell, primed by a tissue-specific, i.e., brain-specific antigen. The primed therapeutic cell targets and has a biological effect on (e.g., kills) cells in its proximity, including cells that express the target antigen and brain-specific antigen as well as cells that express the target antigen but not the brain-specific antigen. In this way, the therapeutic cells have an effect on cells around the primed cell (i.e., only in the brain), leading to effective treatment or clearance of all diseased cells.

Figure 1C:
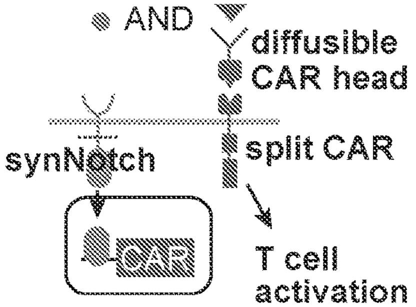

In this example, the size of the zone may be widened or tuned as desired, e.g., through the use of a diffusible payload, stability of the therapeutic employed (e.g., CAR stability). For example, FIG. 1C depicts a circuit that includes a synNotch binding-triggered transcriptional switch configured to bind a priming antigen (circle) which induces expression of a diffusible CAR head. The diffusible CAR head is specific for a disease-specific targeting antigen (triangle) and is bound by a portion of a CAR, referred to in FIG. 1C as a "split CAR", that includes the intracellular signaling components necessary for T cell activation upon antigen binding. Accordingly, by diffusing away from the primed cell, the diffusible CAR head serves to mediate antigen recognition and target cell treatment in more distant T cells that express the split CAR, but do not necessarily express the diffusible CAR head.

Figure 1D:
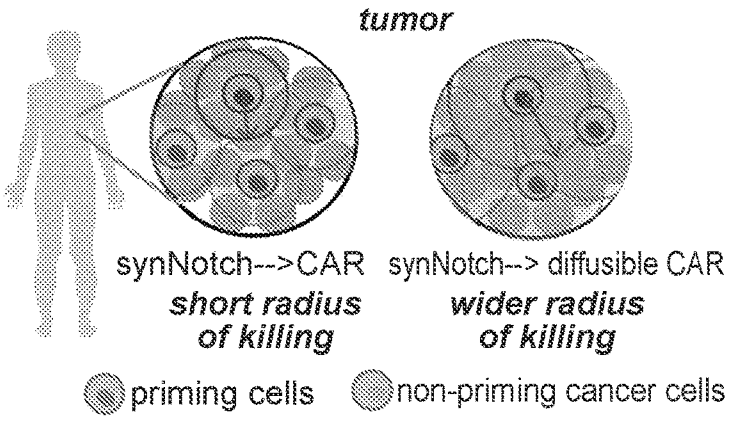

As depicted in the left panel of FIG. 1D, by using a circuit that includes a synNotch driving expression of a traditional CAR (i.e., a single continuous chain having an antigen recognition domain and the intracellular signaling components), the killing radius of non-priming cancer cells that express the killing antigen is kept relatively short. In comparison, as depicted in the right panel of FIG. 1D, by using a circuit that includes a diffusible orthogonal bispecific adapter, such as a diffusible CAR head, the killing radius of non-priming cancer cells that express the killing antigen is widened. Accordingly, the desired killing radius may be controlled as desired. In some instances, e.g., a short killing radius may be desired where a killing antigen is expressed in non-cancerous tissues (i.e., bystander tissues). In other instances, a wide killing radius may be desired where, e.g., relatively few cells expressing the priming antigen are present diffusely throughout a cancerous area of a subject.

The following examples describe a circuit for the treatment of glioblastoma. As would be recognized, the general concept can be applied to other diseases and conditions.

Example 2: Testing SynNotch Receptor Antigen Targets for Glioblastoma

Figure 2A:
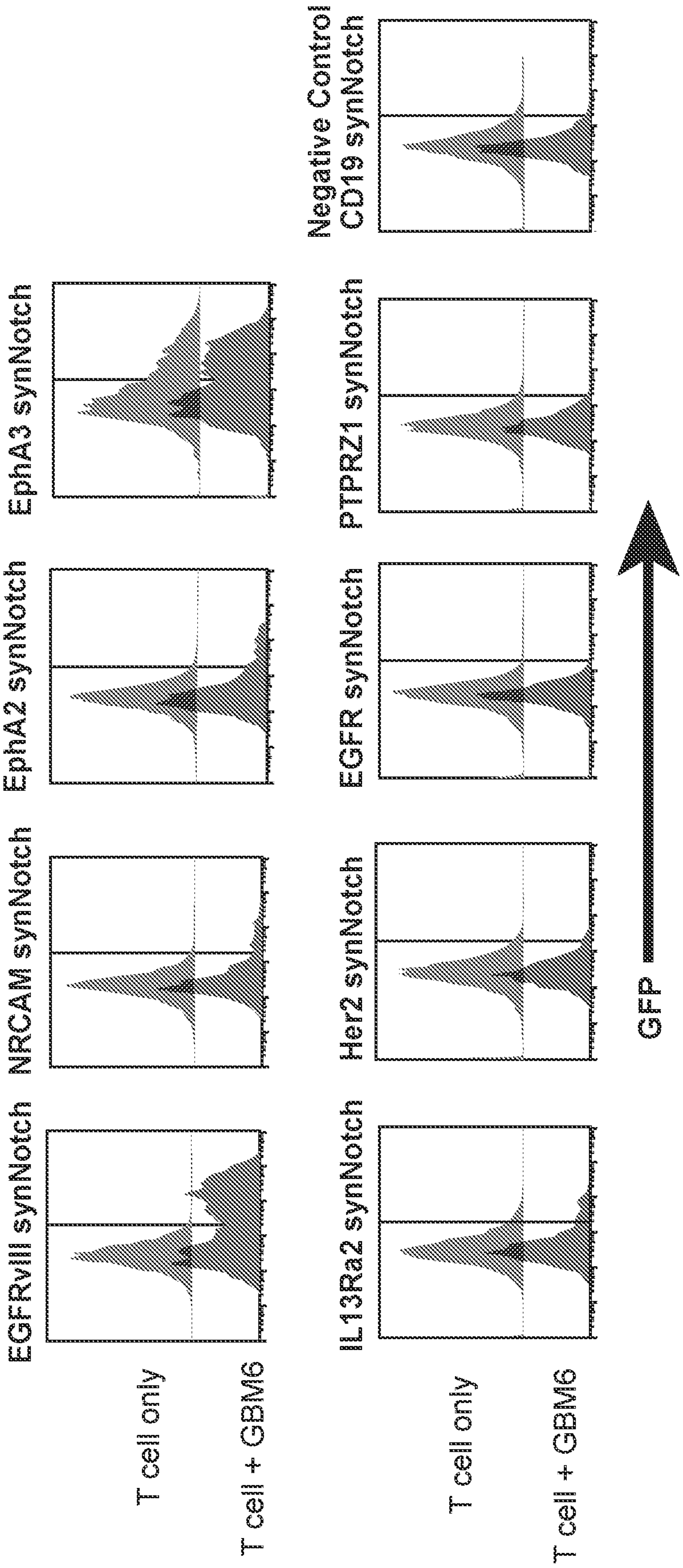
FIG. 2A-2B demonstrate the activation, selectively in the presence of targeted GBM cells, of synNotch receptors targeted to various antigens in synNotch→CAR T cell GBM circuits as described herein.

In this example, circuits employing synNotch receptors to various target antigens were tested in T cells for targeting of GBM. Specifically, human primary CD8+ T cells were engineered with a selection of synNotch receptor antigen targets for Glioblastoma, namely EGFRvIII, NRCAM, EphA2, EphA3, IL13Ra2, Her2, EGFR, and PTRZ1, and the corresponding response elements controlling expression of a reporter (eGFP). These CD8+ synNotch AND-gate T cells are configured to first sense the respective surface GBM antigen via the synNotch receptor, and then, if detected, express the eGFP reporter. Primary CD8+ synNotch AND-gate T cells were cultured alone ("T cell only") or co-cultured with GBM cells ("T cell+GBM6). The GMB cells employed were GBM6 cells, a human patient-derived xenograft (PDX) adult glioblastoma cell line. FIG. 2A provides histograms of reporter (eGFP) expression levels, showing synNotch receptor activation for the various antigens.

Figure 2B:
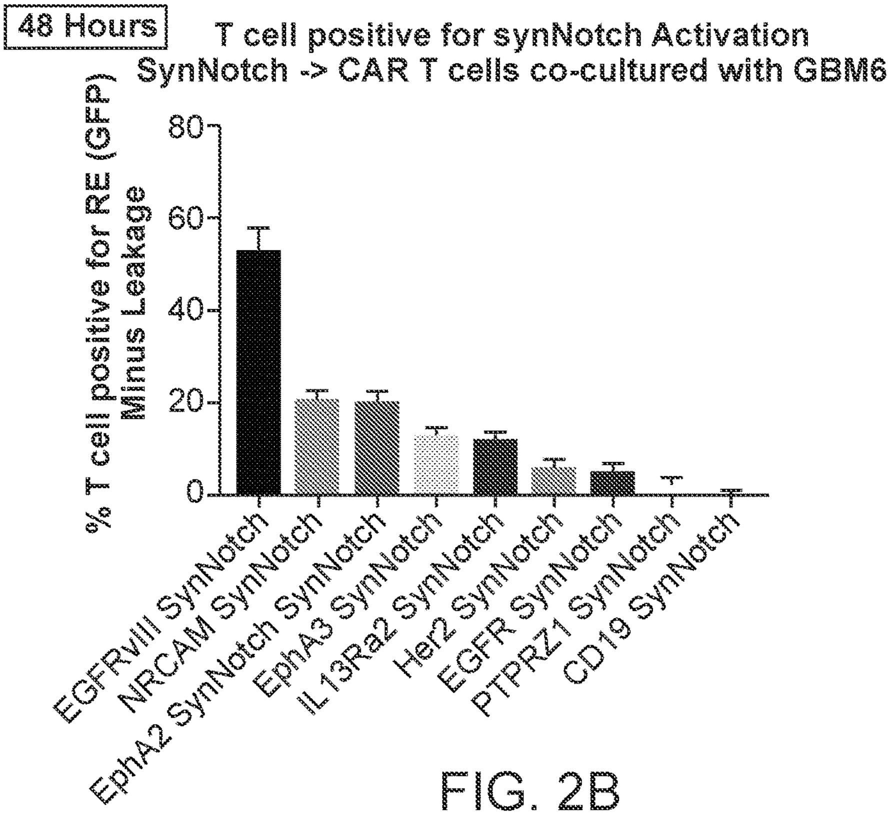

FIG. 2B provides quantification related to FIG. 2A. Specifically, quantification of CD8+ synNotch AND-gate primary T cell activation minus the basal leakage of GFP expression that is independent of synNotch receptor binding to its target antigen. These data show the various levels of activation of the construct tested with the particular GBM6 cell line, demonstrating that various antigens may be targeted, e.g., depending on the desired level of activation sensitivity and/or the presence and/or level of the particular antigen in target cell populations.

Figure 3A:
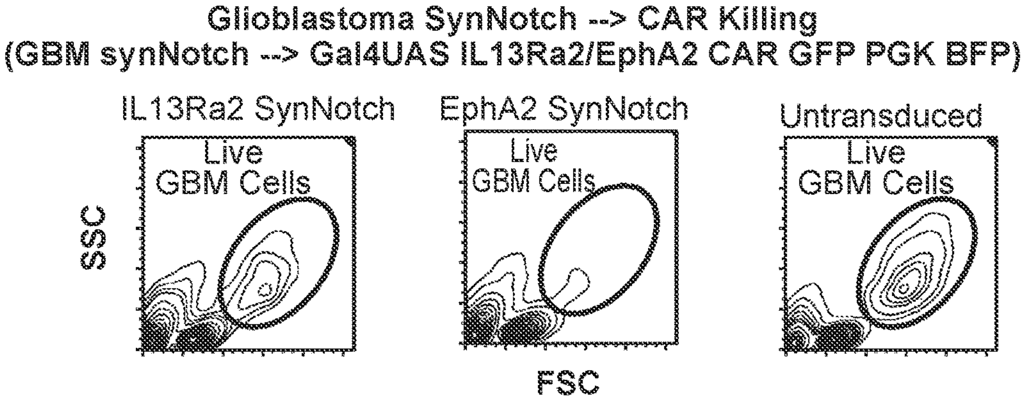
FIG. 3A-3D demonstrate selective synNotch activation and cell killing in the presence of targeted GBM cells with synNotch→CAR T circuits as described herein.

Circuits employing IL13Ra2 and EphA2 antigen targeting were further evaluated. Specifically, human primary CD8+ T cells were engineered with the anti-IL13Ra2 synNotch receptor or anti-EphA2 synNotch receptor with the corresponding response elements controlling expression of the anti-IL13Ra2/EphA2-4-1BBz CAR GFP receptor. These CD8+ synNotch AND-gate T cells first sense surface EphA2 or IL13Ra2, respectively, via the synNotch receptor, and then the cells express the anti-IL13Ra2/EphA2 CAR and are primed for activation in response to CAR antigen binding. FIG. 3A provides forward (FSC) and side scatter (SSC) flow cytometry plots after 24 hr co-culture of CD8+ synNotch AND-gate primary T cells with a primary GBM cell line (SF11411). The target SF11411 are indicated in the circular gates. As shown by a reduction of cells in the SF11411 gate in the IL13Ra2 synNotch and EphA2 synNotch panels as compared to the untransduced controls, the synNotch AND-gate T cells targeting either antigen resulted in killing of the targeted SF11411 GBM cells.

Figure 3B:
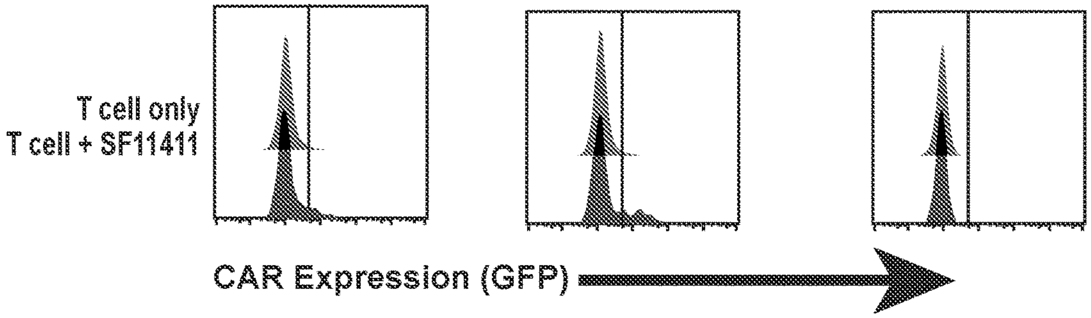

Expression of the CAR, as measured via the GFP reporter, was assessed in the presence ("T cell+SF11411") and absence ("T cell only") of target SF11411 GBM cells. FIG. 3B provides histograms of a-IL13Ra2/EphA2 CAR GFP receptor expression level in these contexts, showing that the CAR is expressed, and/or expression is increased, when the engineered T cells are co-cultured with SF11411 as compared to when the engineered T cells are cultured alone.

Figure 3C:
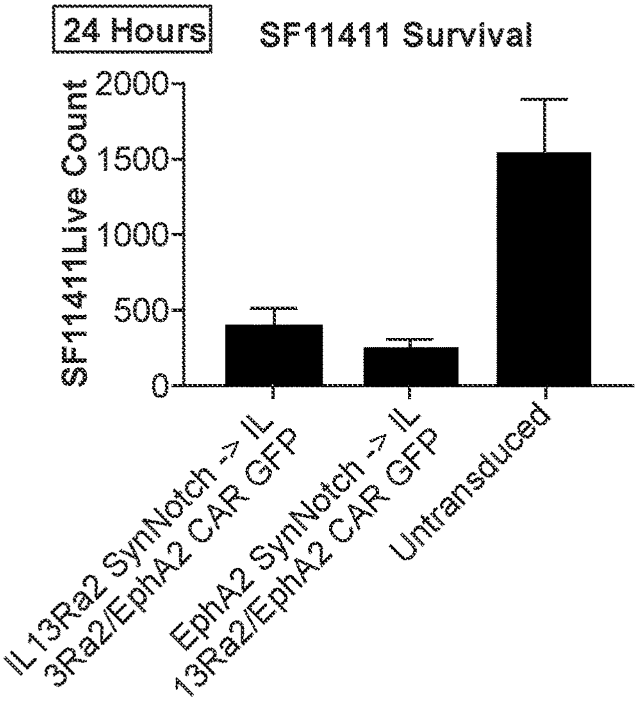
Figure 3D:
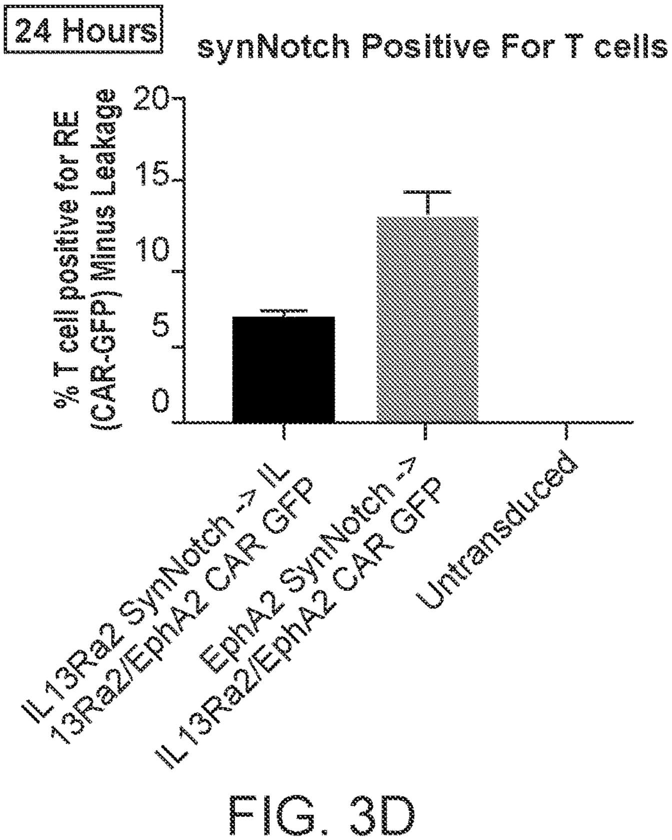

FIG. 3C provides quantification related to FIG. 3A, specifically showing quantification of replicate CD8+ synNotch AND-gate primary T cell cytotoxicity induced by the IL13Ra2 synNotch and EphA2 synNotch circuits. FIG. 3D provides quantification related to FIG. 3B, specifically showing quantification of CD8+ synNotch AND-gate primary T cell activation minus the basal leakage of GFP expression that is independent of synNotch receptor binding to its target antigen. As can be seen in the data, expression of the encoded CAR is induced in the presence of GBM target cells (SF11411).

Collectively, these data demonstrate that various antigens may be employed in the subject circuits to drive expression of an antigen-specific therapeutic, such as a CAR, in the presence of target GBM cells. In addition, the target therapeutic is essentially not expressed in the absence of the target GBM cells due to the absence of the antigen which induces expression of the therapeutic. Correspondingly, these data demonstrate targeted and effective killing of GBM cells the circuits described herein.

Example 3: Multi-Antigen CAR T Cells Precisely and Durably Treat Heterogeneous Glioblastoma The following example shows that multi-antigen CAR T cells can precisely and durably treat heterogeneous glioblastoma. This example can be extrapolated to other therapeutic proteins and the treatment of other disease since the concepts are generally the same. Treatment of solid cancers with chimeric antigen receptor T cells is challenging because of a lack of antigens that are both tumor-specific and homogenously expressed. In glioblastoma, the epidermal growth factor receptor variant III neoantigen is tumor-specific but expressed heterogeneously, which allows for tumor escape. In contrast, more homogenously expressed glioblastoma antigens are non-ideal because of expression in other normal organs, yielding potential cross-reactive toxicity. Here it is shows that multi-antigen recognition circuits have the flexibility and precision to overcome these twin challenges. Using synNotch receptors as a specificity pre-filter (recognizing neoantigens or tissue-specific antigens), the cytotoxic activity of CAR T cells can be restricted to a local site, enabling controlled killing via antigens that are not absolutely tumor-specific. By integrating multiple imperfect but complementary antigens, both the specificity and durability of T cells directed against glioblastoma can be improved and provide a general recognition strategy applicable to other solid tumors.

This approach involves "prime-and-kill" dual antigen-recognition T cell circuits: a synNotch receptor that recognizes a priming antigen either a tumor-specific but heterogeneous antigen (EGFRvIII) or a brain-specific antigen, such as myelin oligodendrocyte glycoprotein (MOG), is used to locally induce expression of a CAR that recognizes tumor-associated antigens (e.g. killing antigens: EphA2 or IL13Rα2) that are relatively homogeneous throughout the tumor but are not necessarily tumor-restricted. T cells bearing these types of circuits can be locally activated by the priming antigen to mediate specific cytotoxicity against neighboring cells expressing the killing antigen. Such cytotoxicity is thought to operate in a local "blast radius" around the priming cells, avoiding indiscriminate killing in distant normal tissues that express the killing antigen but that lack the priming antigen. This type of circuit spatially integrates recognition of two imperfect but complementary antigen targets across multiple neighboring cells. The priming antigen provides specificity, while the killing antigen ensures homogeneity of the therapeutic attack.

It has been shown that T cells expressing this type of prime-and-kill circuit show markedly improved effectiveness and durability in treating heterogeneous GBM PDX tumors in mice, while showing no cross-reactivity with tissues expressing the killing antigen only. This type of T cell circuit can integrate information across multiple neighboring cells in a tumor, and provides a powerful tool to overcome fundamental challenges in recognizing and eliminating solid tumors. With these circuits, antigens that are imperfect individually can be combined to yield more precisely and effectively recognized multi-antigen tumor signatures. This work clearly demonstrates how cell-based therapies are unique amongst therapeutic platforms in that they can be programmed to recognize and treat diseases based on nuanced, multi-parameter features.

Example 3 Results

Figure 5:
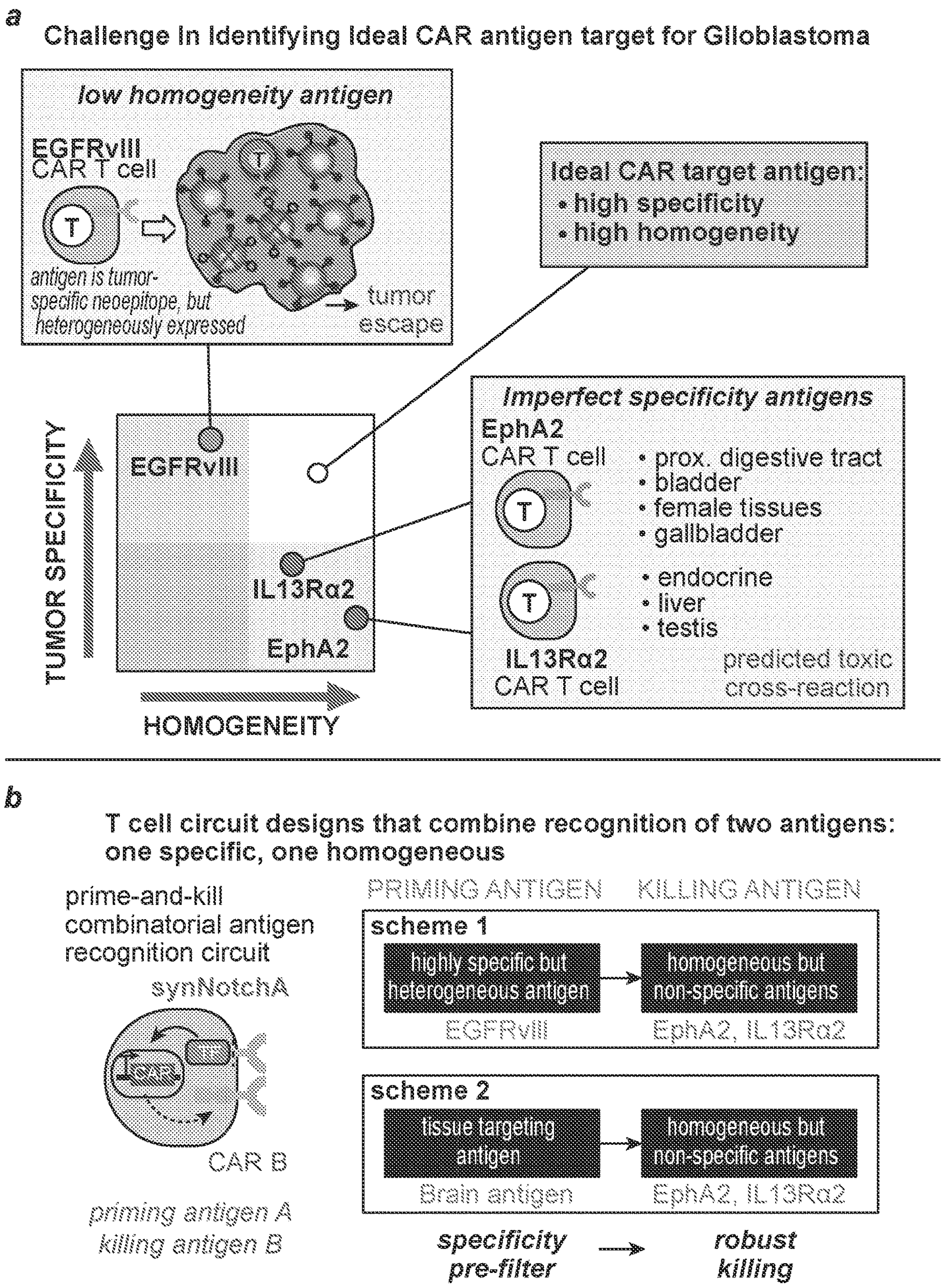
FIG. 5 shows the design of combinatorial antigen "prime-and-kill" circuits to overcome dual challenges of antigen heterogeneity and off-tumor toxicity, where antigen A is MOG, CDH10, PTPRZ1 or NRCAM and antigen B is a disease-specific antigen, for example. This figure shows examples shows "killing" circuits that use a chimeric antigen receptor. However, these circuits can be readily adapted to produce other molecules, e.g., antibodies, enzymes or cytokines, etc.).

Design of dual antigen prime-and-kill circuits that maintain high specificity but can overcome antigen heterogeneity Conventional single antigen targeted CAR T cells allow escape of tumor cells that do not express the target antigen and, thus, can in certain cases be ineffective against antigens with heterogeneous expression (FIG. 5*a*). Dual antigen prime-and-kill CAR T cell circuits (Morsut et al., 2016; Roybal et al., 2016b) are be able overcome the heterogeneous expression of tumor antigens (FIG. 5*b*). These circuits use a constitutively expressed synNotch receptor to recognizes a tumor-specific antigen A (referred to as the priming antigen). Recognition of antigen A leads to activation and subsequent proteolytic cleavage of the synNotch receptor, releasing an intracellular transcriptional activating domain that can drive the expression of a CAR that recognizes antigen B (referred to as the killing antigen). With this type of circuit, the T cell does not express the CAR against the killing antigen unless first primed by the synNotch receptor activation.

One flexible feature of this circuit is the choice of the priming vs killing antigens. Ideally, the priming antigen should be highly tumor-specific, but in principle would need not be homogenously expressed by the tumor. Conversely, the killing antigens would need not be absolutely tumor-specific (since the priming antigen would provide specificity) but should be homogenously expressed throughout the tumor cells. Thus, with this type of circuit, a T cell could become locally primed by a highly specific but heterogeneous antigen, then become activated to mediate killing of tumor cells expressing the killing antigen, within a local radius around the priming signal. In short, two imperfect antigens with different shortcomings could be combinatorially recognized in a complementary manner by such a dual antigen circuit. Below describes two ways to design such a circuit—one primed by a tumor specific neoantigen, and another primed by a tissue specific antigen (FIG. 5*b*).

Design of a Circuit to Recognize Heterogeneous GBM: Priming by EGFRvIII and Killing by EphA2 or IL13Rα2

The T cell circuit as shown in FIG. 6*a* was designed to recognize and kill EGFRvIII-positive GBM. GBM specific neoantigen EGFRvIII was targeted as the priming antigen. Although potential cross-reactivity is not a problem, the EGFRvIII neoepitope is heterogeneously expressed in GBM (between 10-95% of the cells in a tumor express EGFRvIII; O'Rourke et al., 2017). In a recent clinical trial evaluating a CAR T cell targeting EGFRvIII, tumors recurred despite the reduction of EGFRvIII-positive GBM cells, most likely due to the survival and regrowth of EGFRvIII-negative cells (O'Rourke et al., 2017). In summary, EGFRvIII is an excellent target from the perspective of specificity, but its heterogeneous expression throughout the tumor makes it non-ideal as a killing antigen.

For killing targets, we focused on Ephrin type A receptor 2 (EphA2) and IL13 receptor α2 (IL13Rα2). Both antigens are expressed by the vast majority of GBM cells and absent in the normal brain, but are also expressed at low levels in some non-tumor tissues (i.e. these are GBM-associated antigens rather than GBM-specific antigens) (Bielamowicz et al., 2018; Hegde et al., 2013b; Wykosky et al., 2005). The lack of perfect tumor-specificity makes these GBM-associated antigens non-ideal targets for conventional single-target CAR T cell therapy approaches. These could, however, serve as effective killing antigens, if tumor selectivity was provided by the priming antigen.

Thus, the prime-and-kill circuit we engineered recognized EGFRvIII with a synNotch receptor, which then induced the expression of a CAR that recognized both EphA2 or IL13Rα2 (α-EGFRvIII synNotch α-EphA2/IL13α2 CAR). A tandem CAR was used (see FIG. 11*a* for details of circuit design) with an extracellular region containing an EphA2 single chain antibody fused to the IL13 mutein (a variant of the IL13 ligand with higher affinity to IL13α2 over IL13Rα1) (Kahlon et al., 2004). It was reasoned that targeting of multiple killing antigens (EphA2 OR IL13Rα2) rather than a single antigen would further reduce the risk for tumor escape via loss of killing antigen.

For target cells, the U87 GBM tumor cell line was used, which is positive for both EphA2 and IL13Rα2 but negative for EGFRvIII (Chow et al., 2013; Krenciute et al., 2016). We constructed an EGFRvIII-positive version of the U87 cell line by stably transfecting with EGFRvIII (U87-EGFRvIII) (Johnson et al., 2015; Ohno et al., 2013). The U87-EGFRvIII-positive and U87-EGFRvIII-negative cells could be mixed in varying ratios to recapitulate different levels of heterogeneity observed in GBM patients (10-100% priming cells) (FIG. 6*b*). In vitro cytotoxicity assays were preformed with primary human CD8+ T cells that were engineered with the α-EGFRvIII synNotch→α-EphA2/IL13Rα2 CAR circuit. In this model, T cells were primed by the EGFRvIII-positive cells in the tumor, inducing them to express the CAR that could kill neighboring tumor cells, including those lacking EGFRvIII expression (FIG. 6*c*).

It was found that CD8+ T cells engineered with the α-EGFRvIII synNotch→α-EphA2/IL13Rα2 CAR prime-and-kill circuit can eradicate heterogeneous U87 GBM cell populations in vitro, even with as low as 10% EGFRvIII-positive priming cells (FIG. 6*d,e*). In contrast, no killing was observed in the absence of priming cells. In these assays, the induction of CAR expression and the kinetics of killing of the two different tumor cell populations (EGFRvIII-positive and EGFRvIII-negative) was tracked over 72 hours (see FIG. 11*d* for CAR induction). Effective clearance (p=0.0149; t test), was observed with as low as 10% priming cells, although killing was somewhat slower compared to 50% priming cells (FIG. 2*d* and S1e). Taken together, these in vitro killing studies suggest that the prime-and-kill circuit represents a promising strategy that could significantly reduce the chances of tumor escape due to heterogeneity.

T Cells with the α-EGFRvIII synNotch→α-EphA2/IL13Rα2 CAR Circuit Effectively Inhibit the Growth of Heterogeneous EGFRvIII Positive GBM Tumors in the Brain without Affecting Co-Transplanted Flank Tumors Lacking the Priming Antigen Based on these in vitro data, anti-tumor activities of these prime-and-kill CAR T cells were evaluated in a GBM xenograft mouse model. First, to systematically explore different degrees of EGFRvIII heterogeneity, U87-EGFRvIII-negative cells were mixed with with U87-EGFRvIII-positive cells at different ratios (0:100; 50:50; and 100:0) and injected the mixed population into the brains of immunodeficient NCG mice (FIG. 7*a*). U87-EGFRvIII-negative were transfected cells with the wild-type EGFR to generate an EGFRvIII-negative partner cell line that grew at the same rates as the EGFRvIII-positive cells (see FIG. 12) (Bonavia et al., 2012). It was confirmed that the mixed ratio of EGFRvIII-negative vs. EGFRvIII-positive cells was maintained in vivo by histological examination on day 6 (FIG. 12). Mice bearing these tumors were then treated with human primary T cells that were either not transduced (negative control) or transduced with the prime-and-kill circuit. It was found that neither prime-and-kill CAR T cells or control T cells showed any clearance of the 0% EGFRvIII-positive tumors, but the prime-and-kill CAR T cells showed equally effective tumor clearance of both the 50% and 100% EGFRvIII-positive tumors (controls did not show clearance) (FIG. 7*b*). Thus, in this context, prime-and-kill CAR T cells can recognize and effectively overcome tumors with heterogeneous EGFRvIII expression.

To evaluate whether the function of prime-and-kill CAR T cells is localized to the GBM site (thus avoiding cross-reactivity with other distant normal tissues expressing the killing antigens), it may be important to determine whether the T cells that have been primed by EGFRvIII within the GBM tumor site can mediate any anti-EphA2 or IL13Rα2 activity systemically. To this end, as a specificity control, parallel experiments were performed with mice inoculated with two tumors: a 50% EGFRvIII-positive U87 tumor in the brain and a U87-EGFRvIII-negative tumor in the flank (FIG. 7*c*). Here, the flank tumor represents a potentially cross-reactive normal tissue that expresses the killing antigens but not the priming antigen.

On day 6 following the tumor inoculation, the mice received i.v. administration of prime-and-kill CAR T cells or control non-transduced T cells (n=6/group). All the mice treated with control T cells showed tumor growth at both sites, and reached the euthanasia endpoint rapidly with a median survival of 25.5 days. The mice treated with prime-and-kill CAR T cells, in contrast, demonstrated significant suppression of the intracranial tumor growth compared with that in control mice ($p<0.001$; t test). Importantly, however, the mice treated with the prime-and-kill CAR T cells did not show statistically significant suppression of the flank tumor compared with the control group ($p=0.4$; t test, FIGS. 3*d* and *e*). The selective lack of killing in the non-priming flank tumor indicates that the cytotoxic activity of the prime-and-kill CAR T cells is spatially confined to the intracranial tumors expressing both priming and killing antigens.

Prime-and-Kill CAR T Cells Show Locally Induced Expression of the CAR

To further confirm that the EGFRvIII-induced expression of the α-EphA2/IL13Rα2 CAR was limited to the intracranial GBM tumor (EGFRvIII-positive), a CAR-GFP construct was engineered such that the T cells will express GFP upon priming of synNotch receptor. From the dual tumor mice (bearing EGFRvIII-positive intracranial tumor and EGFRvIII-negative flank tumor), we isolated human T cells from the intracranial and flank tumors as well as spleens at 2 days following i.v. administration of prime-and-kill CAR T cells. T cells recovered from the intracranial tumor, but not ones from the spleen or flank tumor, expressed GFP (FIG. 70. These findings indicate that expression of the killing CAR is localized to the local environment around the priming antigen. These data support development of synNotch priming system-based CAR T therapy as a safe strategy mitigating systemic on-target, off-tumor toxicities associated with targeting of tumor-associated antigens with imperfect specificity.

Prime-and-Kill CAR T Cells Lead to Complete Remission of GBM6 PDX Tumors that Heterogeneously Express EGFRvIII The efficacy of prime-and-kill CAR T cells in a tumor model which exhibits naturally occurring heterogeneity of EGFRvIII expression was evaluated (FIG. 8*a*). The GBM6 patient-derived xenograft (PDX) tumor was identified as a model that shows intrinsic EGFRvIII heterogeneity (FIG. 8*a*), and most importantly, a highly reproducible ability to evade treatment by the EGFRvIII single antigen CAR. When implanted intracranially, GBM6 tumors rapidly grow and kill mice within 40 days (FIG. 8*c*). When the mice are treated with the EGFRvIII CAR, the tumors shrink dramatically, but slowly and steadily recur with high reproducibility (FIG. 8*c*, purple dotted line, and FIG. 13*e*). These recurrent tumors show loss of EGFRvIII expression (FIG. 8*g*). Further in vitro studies show that GBM6 cultures have individual cells within the population with undetectable levels of EGFRvIII antigen, and that these cells are resistant to killing by the conventional EGFRvIII CAR T cells (FIG. 13*c,d*). In summary, GBM6 mimics the heterogeneity-based escape observed in EGFRvIII CAR clinical trials, and therefore represents an ideal model in which to evaluate alternative T cell circuits that could overcome these problems.

CD8+ T cells engineered with the α-EGFRvIII synNotch→α-EphA2/IL13Rα2 CAR circuit could eradicate the heterogeneous GBM6 populations in vitro (FIG. 13*a*). When NCG mice bearing GBM6 tumors in the brain received i.v. infusion of control, non-transduced T cells, all of the mice (n=5) died of tumor progression by Day 42 post-tumor inoculation (FIGS. 8*b* and *c*). Treatment with α-EGFRvIII CAR T cells consistently (n=6) resulted in recurrence of EGFRvIII-negative tumors following initial regression (3 of 6 mice died of tumor progression by Day 125), indicating clinical relevance of the GBM6 model (FIG. 8 *c* and *g*) (O'Rourke et al., 2017). Moreover, we did not detect iv. infused EGFRvIII CAR T cells in the recurred tumors, indicating lack of T cell persistence (FIG. 8*g*). In striking contrast, all of the mice (n=6) treated with the prime-and-kill CAR T cells showed long-term complete remission of the GBM6 tumors (FIG. 8*b, c*). This more durable and complete tumor clearance was highly reproducible (FIG. 13*e*). Post-mortem immunofluorescence analysis showed absence of tumor cells but persistence of CAR T cells in the brain parenchyma and meninges (FIG. 8*f*). To visualize brain-restricted priming and induction of CAR expression, the EphA2/I113Ra2CAR-GFP fusion construct was utilized. Notably, 6 days post T cell infusion, we detected GFP positive prime-and-kill CAR T cells (also stained for human CD45) in the tumor bed but none in the spleen (FIG. 8*h*).

Taken together, the prime-and-kill CAR T cells are superior to the conventional α-EGFRvIII CAR T cells in terms of their ability to induce a durable and more complete remission of the heterogeneous GBM6 model. Thus, these prime-and-kill CAR T cells can both maintain EGFRvIII-directed tumor specificity (shown in prior section) and overcome EGFRvIII heterogeneity (shown here).

Prime-and-Kill GBM Circuits Using Brain-Specific Antigens

These results clearly demonstrate that prime-and-kill CAR T cells can be efficiently primed by antigens that are not uniformly expressed on all of the tumor cells. Furthermore, it has been demonstrated that prime-and-kill CAR T cells can achieve trans-priming/killing-priming off of one cell inducing killing of a different but neighboring cell. Hence, it was hypothesized that it might also be possible to design T cells that are locally primed by recognizing tissue-specific antigens expressed solely on non-malignant cells (FIG. 9*a*). For example, in the case of GBM, it might be possible to design T cell circuits that are primed by recognizing a brain-specific antigen, which then triggers local killing based on the GBM antigens EphA2 and IL-13Rα2. An anti-brain synNotch→EphA2/IL-13Rα2 CAR prime-and-kill CAR T cell would thereby provide a potential solution for treating EGFRvIII-negative GBM patients.

Two brain-restricted surface proteins, Cadherin 10 (CDH10)—a brain-specific cadherin, and myelin oligodendrocyte glycoprotein (MOG)—a surface protein on the myelin sheath of neurons (which is also an autoantigen involved in multiple sclerosis) were identified bioinformatically. The predicted tissue expression of these antigens is shown in FIG. 9*b*. Antibodies that bind these antigens were identified and used them to construct cognate synNotch receptors. Several of these synNotch receptors were screened to identify versions that could be activated by cells expressing mouse isoforms of CDH10 or MOG (FIG. 9*c*), and thus these receptors can be used to mediate priming from endogenous mouse brain tissue. Circuits in which the brain-specific synNotch receptors induced expression of the α-EphA2/IL-13Rα2 tandem CAR were then constructed (FIG. 9*d*). It was found that CD8+ T cells engineered with the α-CDH10 or α-MOG synNotch→α-EphA2/IL-13Rα2 CAR circuit can only eradicate U87 GBM cell population or GBM6 cell population in the presence of trans-priming cell (MOG+ or CDH10+ cells) in vitro (FIG. 14*a, b*).

To test the efficacy of these brain antigen-primed circuits in vivo, GBM6 PDX tumors were implanted into the brains of NCG mice and treated them with T cells that could be primed based on recognition of MOG or CDH10. In both cases, the majority of mice treated with the prime-and-kill circuit T cells showed effective GBM6 tumor clearance (FIG. 9*e, f*). These observations suggest that the brain prime-and-kill T cells can indeed be effectively primed by recognition of tissue-specific antigens in the mouse brain, thereby locally inducing the expression of the killing CAR receptor. The mice treated with either circuit show significantly improved survival over those treated with control T cells (FIG. 9*e, f*).

To evaluate whether the effects of MOG- or CDH10-primed CAR T cells are restricted to tumors in the brain, these experiments were repeated by simultaneously implanting GBM6 tumors in the brain and the flank, and intravenously infusing the brain prime-and-kill CAR T cells (FIG. 9*g*). Consistent with the last experiments, both the MOG- and CDH10-primed CAR T cells demonstrated effective anti-brain tumor response (FIG. 9*h*). In the flank, MOG-prime-and-kill CAR T cells showed no effects on the tumor growth compared with control untransduced T cells, suggesting that the MOG-prime-and-kill CAR T cells functions in a brain-specific manner. On the other hand, CDH10-primed CAR T cells showed significant reduction of the tumor size in the flank, suggesting possibilities that the anti-CDH10 scFV may be cross-reactive to epitopes on other antigens that are present outside of the brain, or that CDH10 expression may not be sufficiently restricted to the brain as suggested by RNA-seq data indicating CDH10 mRNA expression in non-CNS organs (FIG. 9*b*).

Overall, these data indicate versatility of the prime-and-kill CAR T cells, including integrate priming from normal tissue-specific antigens.

Example 3 Methods

SynNotch Receptor and Response Element Construct Design

SynNotch receptors were built by fusing the EGFRvIII 139 scFv (Johnson et al., 2015), MOG M26 scFv (von Büdingen et al., 2002), and CDH10 (gift from Sidhu lab) to the mouse Notch1 (NM 008714) minimal regulatory region (Ile1427 to Arg1752) and Gal4 DBD VP64. All synNotch receptors contain an n-terminal CD8a signal peptide for membrane targeting and a myc-tag or flag-tag for easy determination of surface expression with a-myc A647 (cell-signaling #2233) or a-flag A647 (RND systems #IC8529R); see Morsut et al. (Morsut et al., 2016) for receptor synNotch receptor peptide sequences). The receptors were cloned into a modified pHR' SIN:CSW vector containing a PGK or SFFV promoter for all primary T cell experiments. The pHR' SIN:CSW vector was also modified to make the response element plasmids. Five copies of the Gal4 DNA binding domain target sequence were cloned to a minimal CMV promoter. Also included in the response element plasmids is a PGK promoter that constitutively drives mCherry or BFP expression to easily identify transduced T cells. Inducible CARs were built by fusing EphA2 scFv (Goldgur et al., 2014), IL13 Mutein [E13K,K105R] (Krebs et al., 2014), or IL13 Mutein [E13K,K105R]-G4Sx4-EphA2 scFv (Goldgur et al., 2014) to the hinge region of the human CD8a chain and transmembrane and cytoplasmic regions of the human 4-1BB, and CD3z signaling endodomains. The inducible CAR constructs were cloned via a BamHI site in the multiple cloning site 3' to the Gal4 response elements. For some inducible CAR vectors, the CARs were tagged c-terminally with GFP/BFP or contain myc/flag tag to verify surface expression. All constructs were cloned via in-fusion cloning (Clontech #ST0345).

Primary Human T Cell Isolation and Culture

Primary CD4+ and CD8+ T cells were isolated from anonymous donor blood after apheresis by negative selection (STEMCELL Technologies #15062 and #15063). Blood was obtained from Blood Centers of the Pacific, as approved by the University Institutional Review Board. T cells were cryopreserved in RPMI-1640 (UCSF cell culture core) with 20% human AB serum (Valley Biomedical, #HP1022) and 10% DMSO. After thawing, T cells were cultured in human T cell medium consisting of X-VIVO 15 (Lonza #04-418Q), 5% Human AB serum, and 10 mM neutralized N-acetyl L-Cysteine (Sigma-Aldrich #A9165) supplemented with 30 units/mL IL-2 (NCI BRB Preclinical Repository) for all experiments except for the IncuCyte experiments. IncuCyte experiments were cultured in RPMI-1640 (UCSF cell culture core) with 5% human AB serum (Valley Biomedical, #HP1022) supplemented with 30 units/mL IL-2 (NCI BRB Preclinical Repository).

Lentiviral Transduction of Human T Cells

Pantropic VSV-G pseudotyped lentivirus was produced via transfection of Lenti-X 293T cells (Clontech #11131D) with a pHR' SIN:CSW transgene expression vector and the viral packaging plasmids pCMVdR8.91 and pMD2.G using Fugene HD (Promega #E2312). Primary T cells were thawed the same day and, after 24 hr in culture, were stimulated with Human T-Activator CD3/CD28 Dynabeads (Life Technologies #11131D) at a 1:3 cell:bead ratio. At 48 hr, viral supernatant was harvested and in some assays concentrated using Lenti-X concentrator (Clonetech #631231). The primary T cells were exposed to the virus for 24 hr. At day 4 after T cell stimulation, the Dynabeads were removed, and the T cells were expanded until day 9 when they were rested and could be used in assays. T cells were sorted for assays with a Beckton Dickinson (BD) FACs ARIA Fusion. AND-gate T cells exhibiting basal CAR expression were gated out during sorting.

Cancer Cell Lines

The cancer cell lines used were K562 myelogenous leukemia cells (ATCC #CCL-243), L929 mouse fibroblast cells (ATCC #CCL-1), U87 MG GBM cells (ATCC #HTB-14), and GBM6 PDX cells (generous gifts from Dr. Frank Furnari at Ludwig Institute and UCSD). U87-EGFRvIII-negativeluciferase (Ohno et al., 2013) and U87 MG were lentivirally transduced to stably express GFP or mCherry, respectively, under control of the spleen focus-forming virus (SFFV) promoter. At 72 hours after transductions, cells were sorted on an Aria Fusion cell sorter (BD Biosciences) on the basis of GFP expression to be 100% GFP or mCherry positive and subsequently expanded. All cell lines were sorted for expression of the transgenes. U87-luciferase and U87-luciferase-mCherry cells were stably transduced with non-mutated EGFR using a retroviral construct (a gift from Matthew Meyerson; Addgene plasmid #11011) to generate EGFRvIII-negative cell lines which grow at a similar rate as the EGFRvIII-positive U87 cell line (see Fig. S2). Overexpression of wild-type EGFR is relevant to human GBM with EGFR amplification (Bonavia et al., 2012). Both GBM6 were lentivirally transduced to stably express both mCherry and firefly luciferase. These cells were cultured in DMEM F12 media, with supplements of EGF (20 μg/mL), FGF (20 μg/mL), and heparin (5 μg/mL). K562s were lentivirally transduced to stably express surface CDH10 (CDH10 extracellular membrane was fused to the PDGF transmembrane domain). K562s and L929 were lentivirally transduced to stably express full length MOG.

In Vitro Stimulation of SynNotch T cells

For all in vitro synNotch T cell stimulations co-cultured with U87, 1×104 U87s were cultured overnight in a flat bottom 96-well tissue culture plate. Next morning, 1×104-5×104 T cells were added to the flat bottom 96-well tissue culture plate and the co-cultures were analyzed at 24-96 hr for activation and specific lysis of target tumor cells. For all in vitro synNotch T cell stimulations co-cultured with GBM6 and T cells, 1×104 GBM6s were cultured overnight in a flat bottom 96-well tissue culture plate. Next morning, 1×104 T cells were added to the flat bottom 96-well tissue culture plate and the co-cultures were analyzed at 24-96 hr for activation and specific lysis of target tumor cells. For all in vitro synNotch T cell stimulations co-cultured with three different cell populations, the target cells (GBM6) were cultured at 1×104 cells and priming cells (either K562 or L929) were cultured at 1×104 cells overnight in a flat bottom 96-well tissue culture plate. Next morning, 1×104 T cells were added to the flat bottom 96-well tissue culture plate and the co-cultures were analyzed at 24-96 hr for activation and specific lysis of target tumor cells. All flow cytometry was performed using BD LSR II or Attune NxT Flow Cytometer and the analysis was performed in FlowJo software (TreeStar).

Assessment of SynNotch AND-Gate T Cell Cytotoxicity

CD8+ synNotch AND-Gate T cells were stimulated for 24-96 hr as described above with target cells expressing the indicated antigens. The level of specific lysis of target cancer cells was determined by comparing the fraction of target cells alive in the culture compared to treatment with non-transduced T cell controls. Cell death was monitored by shifting of the target cells out of the side scatter and forward scatter region normally populated by the target cells. Alternatively, cell viability was analyzed using the IncuCyte Zoom system (Essen Bioscience). Tumor cells were plated into a 96-well plate at a density of 1.0×104 cells per well in triplicate overnight. T cells were added into each well next day at a final volume of 200 μl per well. The target cells and T cells were co-cultured as described above. 2 fields of view were taken per well every 15 minutes. The mean florescence intensity (MFI) was calculated using IncuCyte Zoom software (Essen BioScience) in order to determine the target cell survival. The data were summarized as mean±SEM.

Statistical Analysis and Curve Fitting

Statistical significance was determined by specific tests and presented as means±standard error mean (SEM) or means±standard deviations (SD) as indicated in the figure legends. The Kaplan-Meier estimator was used to generate survival curves, and differences in survival distributions were assessed using Log-Rank test. All p values are provided in the figures or their legends. All statistical analyses were performed with Prism software version 7.0 (GraphPad).

Mouse Models

All mouse experiments were conducted according to Institutional Animal Care and Use Committee (IACUC)—approved protocols. For orthotopic heterogeneous model with U87, a mixture of $1.5\times10^4$ U87-luc-mCherry and $1.5\times10^4$ U87-luc-EGFRvIII-negativeGFP cells was implanted intracranially into 6- to 8-week-old female NCG mice (Charles River), with 6-10 mice per group. For homogeneous U87-luc-GFP-EGFRvIII-positive model, 3×104 cells were injected into the brains of NCG mice. For orthotopic heterogeneous model with GBM6, 1.0×105 GBM6-luc-mcherry cells were implanted intracranially into 6- to 8-week-old female NCG mice with 6-10 mice per group. A stereotactic surgery for tumor cell inoculation was performed with the coordination of the injection site at 2 mm right and 1 mm anterior to the bregma and 3 mm into the brain. Before surgery and for 3 days after surgery, mice were treated with an analgesic and monitored for adverse symptoms in accordance with the IACUC. In subcutaneous model, NCG mice were injected with either 1.0×106 U87-Luc-mcherry+ or 1.2×105 GBM6-luc-mcherry cells subcutaneously in 100 μl of HBSS on day 0. Tumor progression was evaluated by luminescence emission on a Xenogen IVIS Spectrum after intraperitoneal D-luciferin injection according to the manufacturer's directions (GoldBio). Prior to the treatment, mice were randomized such that initial tumor burden in the control and treatment groups were equivalent. Mice were treated with 6.0×106 engineered or the matched number of non-transduced T cells intravenously via tail vein in 100 μl of PBS. Survival was evaluated over time until predetermined IACUC-approved endpoint (hunching, neurological impairments such as circling, ataxia, paralysis, limping, head tilt, balance problems, seizures) was reached (n=6 to 10 mice per group).

Immunofluorescence

Mice were euthanized before being perfused transcardially with cold PBS. Brains were then removed and fixed overnight in 4% PFA-PBS before being transferred to 30% sucrose and were allowed to sink (1-2 d). Subsequently, the brains were embedded in O.C.T. Compound (Tissue-Tek; 4583; Sakura Finetek). Serial 10 μm coronal sections were then cut on freezing microtome and stored at −20° C. Sections were later thawed and stained overnight at 4° C. Primary antibodies used were: CD45 (D9M8I) XP® Rabbit mAb (Cell Signaling Technologies, 1:100), Anti-EGFRvIII, clone DH8.3 (Millipore Sigma, 1:100), Human EphA2 Alexa Fluor 700-conjugated Antibody (R&D Systems, 1:100), and Anti-IL13 receptor alpha 2 antibody (Abcam, 1:100). Secondary antibodies raised in donkey and conjugated with AlexFluor 647 were used at 4° C. for two hours to detect primary labeling. Sections were stained with nuclear dye DRAQ7 (Abcam) or DAPI5 (Thermofisher). Images were acquired using either a Zeiss Axio Imager 2 microscope (×20 magnification) with TissueFAXS scanning software (TissueGnostics) or a Zeiss LSM 780 microscope (×20 magnification) with Zeiss Zen imaging software. Exposure times and thresholds were kept consistent across samples within imaging sessions.

STAR Methods

| REAGENT or RESOURCE | SOURCE | IDENTIFIER |
|---|---|---|
| Antibodies | | |
| CD3 (OKT3) Mouse mAb (Alexa Fluor 647 Conjugate) | Biolegend | 317312 |
| CD45(H130) Mouse mAb(Brilliant Violet 711 Conjugate) | Biolegend | 304050 |
| CD45 (D9M8I) XP ® Rabbit mAb | Cell Signaling Technologies | 13917T |
| Life Technologies Prolong Diamond Antifade DAPI5 | Thermofisher Scientific | P36962 |
| DRAQ7 | Abcam | ab109202 |
| Anti-EGFRvIII, clone DH8.3 | Millipore Sigma | MABS1915 |
| Anti-EGFRvIII, clone DH8.3 [PE/Cy7] | Novus Biologicals | NBP2-50599PECY7 |
| Human EphA2 Alexa Fluor« 700-conjugated Antibody | R&D Systems | FAB3035N |
| Anti-IL13 receptor alpha 2 antibody | Abcam | ab55275 |
| Prolong Glass Antifade Mountant | Thermofisher Scientific | P36980 |
| Myc-Tag (9B11) Mouse mAb (Alexa Fluor ® 647 Conjugate) | Cell Signaling Technology | Cat #2233S; RRID: AB_823474 |
| Myc-Tag (9B11) Mouse mAb (Alexa Fluor ® 488 Conjugate) | Cell Signaling Technology | 2279S |
| Alexa488 rabbit anti-DYKDDDDK (Flag tag) tag clone 1042E | R&D Systems | Cat #IC8529G |
| Dynabead Human T cell Activator anti-CD3/CD28 | Thermo Scientific | Cat#11131D |
| Chemicals, Peptides, and Recombinant Proteins | | |
| Phosphate buffered saline (PBS) | Corning | 21-040-CV |
| Dulbecco's phosphate buffer saline without Ca 2+, Mg 2+ | UCSF-CCF | CCFAL005 |
| Dulbecco's phosphate buffer saline with Ca 2+, Mg 2+ | Fisher Scientific | 21-030-CV |
| Dulbecco's Modified Eagle Medium (DMEM) with glutamax | Thermo Fisher Scientific | 10569-044 |
| DMEM F12 | | |
| Eagle's Minimum Essential Medium (EMEM) w/o L-glutamine | Sigma-Aldrich | 51412C |
| Animal-Free Recombinant Human EGF | PeproTech | AF-100-15-100 ug |
| Recombinant Human FGF-basic | PeproTech | AF-18B-100 UG |
| Heat Inactivated Fetal Bovine Serum (FBS) | UCSF-CCF | ccfaq009 |
| Stemcell Technologies Inc 0.2% Heparin Sodium Salt PBS | STEMCELL Technologies | 07980 |
| Human AB Serum | Valley Biomdical | HP1022HI |
| N-acetyl L-Cysteine | Sigma Aldrich | Cat#A9165 |
| Recombinant human IL-2 protein | NCI BRB Preclinical Repository | https://ncifrederick.cancer.gov/research/brb/ |
| Gentamicin | UCSF Cell Culture Core | N/A |
| Penicillin-streptomycin | UCSF Cell Culture Core | N/A |
| Human Ab Serum | Valley Medical | Cat#HP1022 |
| X-VIVO15 | Lonza | Cat#04-418Q |
| GlutaMAX | Thermo Scientific | Cat#35050061 |
| Cell Trace Far Red | Life Technology | C34564 |
| Cell Trace Violet | Thermo Fisher Scientific | C34564 |
| Penicillin/Streptomycin | thermo fisher scientific | 15140122 |
| FuGENE HD | Promega | E2312 |
| Optimem | Life Technologies | 31985070 |
| TrypLE | Life Technologies | 12605028 |
| Lenti-X Concentrator | Clontech | 631231 |
| In Fusion | Takara Bio | 639650 |
| NEB 5-alpha Competent Cells | New England Bio | C299H |
| BamHI-HF | New England Bio | R3136S |
| Phusion High Fidelity PCR Master Mix | New England Bio | M0531S |
| Q5 High-Fidelity 2X Master Mix | New England Bio | M0492S |
| Zombie Aqua ™ Fixable Viability Kit | Biolegend | 423101 |

-continued

| REAGENT or RESOURCE | SOURCE | IDENTIFIER |
|---|---|---|
| Sytox Blue Dead Cell Stain | Thermo Fisher | S34857 |
| Sytox Green Dead Cell Stain | Thermo Fisher | S34860 |
| Critical Commercial Assays | | |
| RosetteSep Human CD4+ T cell Enrichment Cocktail | STEMCELL Technologies | Cat#15022 |
| RosetteSep Human CD8+ T cell Enrichment Cocktail | STEMCELL Technologies | Cat#15023 |
| Experimental Models: Cell Lines | | |
| GBM6 | Dr. Frank Furnari (UCSD) | |
| Lenti-X 293T Cell Line | Clontech | 631231 |
| K562 CD19 (CD19 extracellular domain_human PDGFR transmembrane domain) | Roybal et al., 2016a | N/A |
| K562 surface GFP ligand + CD19 | Roybal et al., 2016a | N/A |
| U87 EGFRvIII-negativeGFP-luciferase | This paper | NA |
| U87 EGFRWT-mCherry-luciferase | This paper | NA |
| Experimental Models: Organisms/Strains | | |
| NCG (572) | Charles River | |
| Recombinant DNA | | |
| pBABE EGFR WT | Addgene | ID#11011 |
| pHR_SFFV | Addgene | ID#79121 |
| pHR_PGK | Addgene | ID#79120 |
| pHR_Gal4UAS_PGK_mCherry | Addgene | ID#79124 |
| pHR_Gal4UAS_tBFP_PGK_mCherry | Addgene | ID#79130 |
| pHR_PGK_LaG17_synNotch_Gal4VP64 | Addgene | ID#79127 |
| pHR_Gal4UAS_PGK_BFP | This paper | Based on pHR_PGK |
| pHR_PGK_aEGFRvIII_synNotch_Gal4VP64 | This Paper | anti-EGFRvIII scFv 139 sequence from Johnson et al., 2015 |
| pHR_PGK_aMOG_synNotch_Gal4VP64 | This Paper | Anti-MOG scFv M26 sequence from von Büdingen et al., 2002 |
| pHR_PGK_aCDH10_synNotch_Gal4VP64 | This Paper | Anti-CDH10 scFV sequence from Sidhu lab |
| pHR_Gal4UAS_aEphA2_BBZ_GFP_PGK_BFPpHR_Gal4UAS_aCD19_BBz_BFP_PGK_mCherry | This PaperThis Paper | anti-EphA2 scFv sequence from Goldgur et al., 2014anti-CD19 scFv sequence from Porter et al., 2011 |
| pHR_Gal4UAS_IL13_Mutein_BBZ_GFP_PGK_BFPpHR_Gal4UAS_aEphA2_BBZ_GFP_PGK_BFP | This PaperThis Paper | IL13 Mutein [E13K, K105R] derived from Krebs et al., 2014anti-EphA2 scFv sequence from Goldgur et al., 2014 |
| pHR_Gal4UAS_IL13_Mutein_GSLinker_aEphA2_BBZ_GFP_PGK_BFPpHR_Gal4UAS_IL13_Mutein_BBZ_GFP_PGK_BFP | This PaperThis Paper | anti-EphA2 scFv sequence from Goldgur et al., 2014 and IL13 Mutein [E13K, K105R] derived from Krebs et al., 2014IL13 Mutein [E13K, K105R] derived from Krebs et al., 2014 |
| pHR_Gal4UAS_IL13_Mutein_GSLinker_aEphA2_BBZ_GFP_PGK_BFP | This Paper | anti-EphA2 scFv sequence from Goldgur et al., 2014 and IL13 Mutein [E13K, K105R] derived from Krebs et al., 2014 |
| Software and Algorithms | | |
| Prism version 8 | GraphPad | |
| Living Image 4.5 | Perkin Elmer | |

Here it has been shown that more sophisticated T cell recognition circuits that integrate recognition of multiple antigens can be used to overcome these problems in the case of GBM (FIG. 10). In order to demonstrate this, a series of prime-and-kill circuits were constructed. A GBM-specific but heterogeneously expressed neoantigen, EGFRvIII, was targeted as a priming antigen (FIG. 10*a*), and then extended our strategies to target brain-specific antigens that are expressed on non-tumor cells in the brain (FIG. 10*b*).

In the circuits described herein, the synNotch receptor induces gene expression of a tandem CAR that targets two GBM-associated antigens, EphA2 and IL13Rα2. As conventional therapeutic targets, these two antigens can be imperfect, because they are expressed in a few other normal non-brain tissues. However, in these prime-and-kill circuits, because the expression of the cognate CAR is only induced in the proximity of cells expressing EGFRvIII or MOG, this cross-reactivity is mitigated. The prime-and-kill circuit combines these imperfect antigens, and integrates them in a way that optimizes how they each contribute to overall recognition. As EGFRvIII and MOG are very specific in the GBM tumor or the brain, respectively, they represent excellent priming antigens. EphA2 and IL13Rα2 are less specific, but because they are more homogenously expressed, throughout the tumor, targeting of these antigens will likely enhance the killing of a wider population of the GBM cells. As such, as long as their killing is controlled by a localized priming signal, these antigens become more suitable as killing antigen targets. Moreover, even if these killing antigens are not fully homogeneous individually, use of the tandem CAR in killing provides a higher likelihood of tumor clearance (tandem CAR functions as an OR gate) (Hegde et al., 2016). Thus, these circuits can integrate signals from the three antigens, even if presented on different cells within the tumor, inducing a killing response that is highly localized but sufficiently broad to be effective. The circuit is hypothesized to essentially create a killing "blast radius" around the priming cells (FIG. 10*c*). Other recent studies have also explored how EGFRvIII recognition could be harnessed to locally enhance otherwise imperfectly specific therapeutic responses, such as secretion of an EGFR bispecific engager (Choi, 2019).

The in vivo data demonstrate that EGFRvIII or MOG-induced expression of the α-EphA2/IL-13Rα2 CAR and their cytotoxic activity is confined to the intracranial tumors expressing both priming and killing antigens, thereby not affecting tissues expressing the killing antigens at distant sites. In prior in vivo mouse studies (Roybal et al., 2016a), it was found that T cells expressing a similar prime-and-kill circuit can show highly selective killing of implanted tumor cells that homogenously express priming and killing circuits (i.e. "AND-gate"), but did not show any killing of a contralaterally implanted tumor cells that only express the killing antigen. The fact that no killing occurred in the contralateral control tumor shows that priming of the T cells in one organ, does not yield primed T cells that can then kill at a long distance within the body (once priming stimuli are removed, CAR expression decays within hours, precluding mounting of a sustained immune response; Roybal 2016). These observations are consistent with the current model in which synNotch-mediated T cell priming can induce short-range killing of target cells, but not long-range killing.

Regarding EGFRvIII as the priming antigen, approximately 20% of GBM patients are positive for EGFRvIII (Heimberger et al., 2005; Moscatello et al., 1995; Thorne et al., 2016; Wikstrand et al., 1997). Moreover, patients can show heterogeneity of EGFRvIII expression of between 10-95% O'Rourke (O'Rourke et al., 2017). It remains unclear what percent of EGFRvIII-positive cells are necessary in vivo to achieve sufficient priming to eliminate tumors, since the induced killing also results in the parallel reduction of both the non-priming and priming tumor cells; i.e., it may be possible in some cases to eliminate the priming cells too quickly. Nevertheless, based on our data with the GBM6 model (FIG. 8), the EGFRvIII priming strategy appears promising as all mice showed long-term tumor clearance. This compares favorably with other similar treatments (Johnson et al., 2015). The elimination of the priming signal is less of a concern with brain antigen-priming circuits, such as one against MOG, because the prime-and-kill CAR T cells will not kill normal brain cells expressing MOG, as they lack the required killing antigens (EphA2 or IL-13Rα2).

Example 3 References

Bielamowicz et al. (2018). Trivalent CAR T cells overcome interpatient antigenic variability in glioblastoma. Neuro Oncol 20, 506-518.

Bonavia et al. (2012). EGFRvIII promotes glioma angiogenesis and growth through the NF-kappaB, interleukin-8 pathway. Oncogene 31, 4054-4066.

Brown et al. (2016). Regression of Glioblastoma after Chimeric Antigen Receptor T-Cell Therapy. N Engl J Med 375, 2561-2569.

Cameron et al. (2013). Identification of a Titin-derived HLA-A1-presented peptide as a cross-reactive target for engineered MAGE A3-directed T cells. Sci Transl Med 5, 197ra103.

Choi et al. (2019). CAR-T cells secreting BiTEs circumvent antigen escape without detectable toxicity. Nat. Biotechnol. 37:1049-1058

Drumm et al. (2019). Extensive brainstem infiltration, not mass effect, is a common feature of end-stage cerebral glioblastomas. Neuro Oncol.

Goldgur et al. (2014). Generation and characterization of a single-chain anti-EphA2 antibody. Growth Factors 32, 214-222.

Hegde et al. (2013a) Combinational targeting offsets antigen escape and enhances effector functions of adoptively transferred t cells in glioblastoma Mol Ther. 2013 21: 2087-101.

Hegde et al. (2013b). Combinational targeting offsets antigen escape and enhances effector functions of adoptively transferred T cells in glioblastoma. Mol Ther 21, 2087-2101.

Heimberger et al. (2005). Prognostic effect of epidermal growth factor receptor and EGFRvIII in glioblastoma multiforme patients. Clin Cancer Res 11, 1462-1466.

Johnson et al. (2009). Gene therapy with human and mouse T-cell receptors mediates cancer regression and targets normal tissues expressing cognate antigen. Blood 114, 535-546.

Johnson et al. (2015). Rational development and characterization of humanized anti-EGFR variant III chimeric antigen receptor T cells for glioblastoma. Sci Transl Med 7, 275ra222.

June et al. (2018). Chimeric Antigen Receptor Therapy. N Engl J Med 379, 64-73.

Kahlon et al. (2004). Specific recognition and killing of glioblastoma multiforme by interleukin 13-zetakine redirected cytolytic T cells. Cancer Res 64, 9160-9166.

Krebs et al. (2014). T cells redirected to interleukin-13Ralpha2 with interleukin-13 mutein—chimeric antigen receptors have anti-glioma activity but also recognize interleukin-13Ralpha1. Cytotherapy 16, 1121-1131.

Morgan et al. (2013). Cancer regression and neurological toxicity following anti-MAGE-A3 TCR gene therapy. J Immunother 36, 133-151.

Morgan et al. (2010). Case Report of a Serious Adverse Event Following the Administration of T Cells Transduced With a Chimeric Antigen Receptor Recognizing ERBB2. Mol Ther 18, 843-851.

Morsut et al. (2016). Engineering Customized Cell Sensing and Response Behaviors Using Synthetic Notch Receptors. Cell 164, 780-791.

Moscatello et al. (1995). Frequent expression of a mutant epidermal growth factor receptor in multiple human tumors. Cancer Res 55, 5536-5539.

O'Rourke et al. (2017). A single dose of peripherally infused EGFRvIII-directed CAR T cells mediates antigen loss and induces adaptive resistance in patients with recurrent glioblastoma. Sci Transl Med 9.

Ohno et al. (2013). Expression of miR-17-92 enhances anti-tumor activity of T-cells transduced with the anti-EGFRvIII chimeric antigen receptor in mice bearing human GBM xenografts. Journal for immunotherapy of cancer 1, 21.

Parkhurst et al. (2011). T cells targeting carcinoembryonic antigen can mediate regression of metastatic colorectal cancer but induce severe transient colitis. Mol Ther 19, 620-626.

Roybal et al. (2016a). Precision Tumor Recognition by T Cells With Combinatorial Antigen-Sensing Circuits. Cell 164, 770-779.

Roybal et al. (2016b). Engineering T Cells with Customized Therapeutic Response Programs Using Synthetic Notch Receptors. Cell 167, 419-432 e416.

Sampson et al. (2010). Immunologic Escape After Prolonged Progression-Free Survival With Epidermal Growth Factor Receptor Variant III Peptide Vaccination in Patients With Newly Diagnosed Glioblastoma. Journal of Clinical Oncology 28, 4722-4729.

Shahideh et al. (2012). Systematic review of primary intracranial glioblastoma multiforme with symptomatic spinal metastases, with two illustrative patients. J Clin Neurosci 19, 1080-1086.

Thorne et al (2016). Epidermal growth factor receptor targeting and challenges in glioblastoma. Neuro Oncol 18, 914-918.

Watanabe et al. (2018). Expanding the Therapeutic Window for CAR T Cell Therapy in Solid Tumors: The Knowns and Unknowns of CAR T Cell Biology. Front Immunol 9, 2486.

Wikstrand et al. (1997). Cell surface localization and density of the tumor-associated variant of the epidermal growth factor receptor, EGFRvIII. Cancer Res 57, 4130-4140.

Wykosky et al. (2005). EphA2 as a novel molecular marker and target in glioblastoma multiforme. Mol Cancer Res 3, 541-551.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a subject for a brain cancer that is not glioblastoma multiforme comprising:

administering to the subject an immune cell genetically modified with:

(a) a nucleic acid sequence encoding a binding triggered transcriptional switch (BTTS) that binds to brevican core protein (BCAN);

(b) a nucleic acid sequence encoding a chimeric antigen receptor (CAR) that recognizes one or more tumor-associated antigens that are expressed by tumor cells in the subject's brain; and (c) a regulatory sequence operably linked to (b) that is responsive to the BTTS;

wherein binding of the BTTS to BCAN activates expression of the CAR, which binds to and induces killing of the tumor cells.

2. The method of claim 1, wherein the BTTS comprises:

an extracellular domain that comprises a binding domain that recognizes BCAN;

a transmembrane domain;

one or more protease cleavage domains; and a transcriptional activator, wherein binding of the extracellular domain to BCAN results in cleavage of the BTTS at the one or more protease cleavage domains to release the transcriptional activator, and wherein the released transcriptional activator binds to the regulatory sequence of (c) and activates expression of the CAR.

3. The method of claim 1, wherein the subject has a brain cancer selected from diffuse midline glioma (formally known as diffuse intrinsic pontine glioma (DIPG)), medulloblastoma, ependymoma, craniopharyngiom, embryonal tumor, pineoblastoma, brainstem glioma, choroid plexus carcinoma, germ cell tumor, pituitary adenoma, acoustic neuroma, meningioma, oligodendroglioma, haemangioblastoma, central nervous system (CNS) lymphoma, or non-glioblastoma multiforme (GBM) astrocytoma.

4. The method of claim 1, wherein the subject is a human subject.

5. The method of claim 1, wherein the immune cell is a cytotoxic T cell.

6. The method of claim 1, wherein the BTTS comprises a Notch regulatory region.

7. The method of claim 1, wherein the CAR recognizes EphA2, EphA3, IL13RA1, IL13RA2, EGFR, or ERBB2, or any combination thereof.

8. The method of claim 1, wherein the CAR is a tandem CAR.

9. The method of claim 8, wherein the tandem CAR has a first binding domain that recognizes Ephrin type-A receptor 2 (EphA2) and a second binding domain that recognizes Interleukin-13 receptor subunit alpha-2 (IL13RA2).

* * * * *